(12) United States Patent
Harrison

(10) Patent No.: US 6,476,042 B1
(45) Date of Patent: Nov. 5, 2002

(54) COMBINATION THERAPY FOR THE TREATMENT OF MIGRAINE

(75) Inventor: Wilma M. Harrison, Harrison, NY (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/603,630

(22) Filed: Jun. 26, 2000

Related U.S. Application Data

(60) Provisional application No. 60/141,715, filed on Jun. 30, 1999.

(51) Int. Cl.$^7$ ............................................. A61K 31/52
(52) U.S. Cl. ...................................................... 514/264
(58) Field of Search .................................. 514/264, 415

(56) References Cited

U.S. PATENT DOCUMENTS

| | | | | |
|---|---|---|---|---|
| 5,451,588 A | * | 9/1995 | Baker et al. ................. | 514/323 |
| 5,466,823 A | | 11/1995 | Talley et al. ............. | 548/477.1 |
| 5,536,752 A | * | 7/1996 | Ducharme et al. .......... | 514/602 |
| 5,563,165 A | | 10/1996 | Talley et al. ................ | 514/406 |
| 5,691,374 A | | 11/1997 | Black et al. ................. | 514/473 |
| 5,760,068 A | | 6/1998 | Talley et al. ................ | 514/403 |
| 5,861,419 A | | 1/1999 | Deube et al. ................ | 514/334 |
| 5,872,145 A | | 2/1999 | Plachetka ................... | 514/415 |
| 5,994,379 A | | 11/1999 | Bayly et al. ................. | 514/367 |
| 6,034,256 A | | 3/2000 | Carter et al. ................ | 549/458 |
| 6,063,811 A | | 5/2000 | Hancock et al. ............. | 514/473 |
| 6,077,850 A | | 6/2000 | Carter et al. ................. | 514/311 |

FOREIGN PATENT DOCUMENTS

| | | | |
|---|---|---|---|
| DE | 4342568 A1 | * | 6/1994 |
| EP | 0980866 A2 | | 6/1994 |
| EP | 0863134 A1 | | 4/1997 |
| EP | 0743938 B1 | | 4/1999 |
| GB | 2255279 A | | 4/1992 |
| WO | WO 9817292 A1 | | 4/1998 |
| WO | WO 0025779 A1 | | 5/2000 |
| WO | WO 0026216 A1 | | 5/2000 |

OTHER PUBLICATIONS

Abstract to DE 4,342,568 A1, Jun. 1994.*
Abstract to CN 1,086,692, May 18, 1994.
Abstract to DE 4,342,568, Jun. 1, 1994.
Abstract to CN 1129, 105, Aug. 21, 1996.

* cited by examiner

*Primary Examiner*—Dwayne C. Jones
(74) *Attorney, Agent, or Firm*—P. C. Richardson; P. H. Ginsburg; A. D. Joran

(57) ABSTRACT

The present invention relates to a method of treating migraine in a mammal, including a human, by administering to the mammal a $5HT_1$ receptor agonist in combination with caffeine and a cyclooxygenase-2 (COX-2) inhibitor. It also relates to pharmaceutical compositions containing a pharmaceutically acceptable carrier, a $5HT_1$ receptor agonist with caffeine and a cyclooxygenase-2 (COX-2) inhibitor.

12 Claims, No Drawings

COMBINATION THERAPY FOR THE TREATMENT OF MIGRAINE

This application claims benefit of Provisional Application Ser. No. 60/141,715 filed Jun. 30, 1999.

The present invention relates to a method of treating migraine in a mammal, including a human, by administering to the mammal a $5HT_1$ receptor agonist and caffeine in combination with a cyclooxygenase-2 (COX-2) inhibitor. It also relates to pharmaceutical compositions containing a pharmaceutically acceptable carrier, a $5HT_1$ receptor agonist and a COX-2 inhibitor. Examples of agonists of $5HT_1$ receptors are agonists of one or more of the $5HT_{1A}$, $5HT_{1B}$, $5HT_{1C}$, $5HT_{1D}$, $5HT_{1E}$, and $5HT_{1F}$ receptors.

The combined use of $5HT_1$ agonists (e.g. eletriptan, rizatriptan, naratriptan, sumatriptan, zolmitriptan), caffeine and a COX-2 inhibitor for the acute treatment of migraine offers enhanced efficacy than currently used therapies.

Symptomatic treatment helps relieve the pain associated with migraine.

Abortive treatment targets the pathophysiology of migraine and decreases many of the symptoms of migraine, including pain, nausea, photophobia and phonophobia.

NSAIDS have been shown to help in the symptomatic treatment of migraine headache. Its combination with the abortive treatment of the $5HT_1$ agonists is expected to provide an additional effect than the use of either treatment alone.

COX-2 inhibitors have evolved from the NSAIDS and are expected to have similar efficacy with additional safety and tolerability. By selectively inhibiting the COX-2 isoenzyme associated with inflammation and pain, COX-2 inhibitors would be expected to decrease migraine pain with less or no effect on the COX-1 isoenzyme. This isoenzyme maintains gastrointestinal and renal environments. The effect of the NSAIDS on the COX-1 isoenzyme is thought to be responsible for the large incidence of gastrointestinal and renal adverse experiences associated with NSAIDS treatment. Therefore, the use of the COX-2 inhibitors is advantageous with its additional safety and tolerability.

Caffeine has been found to be an analgesic adjuvant for numerous conditions including headache and pain (see Laska et al., JAMA, Vol. 252, 1711–1718 (1984), which is incorporated by reference in its entirety).

SUMMARY OF THE INVENTION

The present invention relates to pharmaceutical compositions for the treatment of migraine in a mammal, including a human, comprising a $5HT_1$ receptor agonist or a pharmaceutically acceptable salt thereof, and caffeine with (a) a compound of the formula:

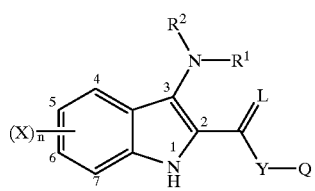

(I)

or the pharmaceutically acceptable salts thereof wherein $R^1$ is hydrogen or $C_{1-4}$ alkyl; $R^2$ is $C(=L')R^3$ or $SO_2R^4$; Y is a direct bond or $C_{1-4}$ alkylene; L and L' are independently oxygen or sulfur;

Q is selected from the following:

(Q-a) $C_{1-6}$ alkyl, (Q-b) halo-substituted $C_{1-4}$ alkyl, (Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo, (Q-d) phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy, nitro, halo-substituted $C_{1-4}$ alkoxy, $S(O)_mR^5$, $SO_2NH_2$, $SO_2N(C_{1-4}$ alkyl$)_2$, amino, $C_{1-4}$ alkylamino, di-($C_{1-4}$ alkyl)amino, $NR^1C(O)R^5$, CN, $C_{1-4}$ alkyl-OH and $C_{1-4}$ alkyl-$OR^5$, (Q-e) a 5-membered monocyclic aromatic group containing one heteroatom selected from O, S and N and optionally containing one, two or three nitrogen atom(s) in addition to said heteroatom, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$, and (Q-f) a 6-membered monocyclic aromatic group containing one nitrogen atom and optionally containing one, two or three additional nitrogen atom(s), and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$;

$R^3$ is —$OR^6$, —$NR^7R^8$, $N(OR^1)R^7$ or a group of formula:

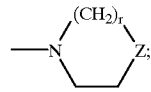

Z is a direct bond, oxygen, sulfur or $NR^5$;

$R^4$ is $C_{1-6}$ alkyl, halo-substituted $C_{1-4}$ alkyl, $C_{1-4}$ alkyl-OH, —$NR^7R^8$, phenyl or naphthyl, the phenyl and naphthyl being optionally substituted with one, two or three substituents independently selected from halo, $C_{1-4}$ alkyl, halo-substitutued $C_{1-4}$ alkyl, hydroxy, $C_{1-4}$ alkoxy and halo-substitutued $C_{1-4}$ alkoxy;

$R^5$ is $C_{1-4}$ alkyl or halo-substituted $C_{1-4}$ alkyl;

$R^6$ is $C_{1-4}$ alkyl, $C_{3-7}$ cycloalkyl, $C_{1-4}$ alkyl-$C_{3-7}$ cycloalkyl, halo-substitutued $C_{1-4}$ alkyl, $C_{1-4}$ alkyl-phenyl or phenyl, the phenyl moiety being optionally substituted with one, or two substituents independently selected from halo, $C_{1-4}$ alkyl, halo-substituted $C_{1-4}$ alkyl, hydroxy, $C_{1-4}$ alkoxy, $C_{1-4}$ alkylthio, amino, di-($C_{1-4}$ alkyl)amino and nitro;

$R^7$ and $R^8$ are independently selected from the following:

(a) hydrogen, (b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl) amino, (c) $C_{3-7}$ cycloalkyl optionally substituted with a substituent independently selected from hydroxy, $C_{1-4}$ alkyl and $C_{1-4}$ alkoxy, (d) $C_{1-4}$ alkyl-$C_{3-7}$ cycloalkyl optionally substituted with a substituent independently selected from hydroxy, $C_{1-4}$ alkyl and $C_{1-4}$ alkoxy, and (f) $C_{1-4}$ alkyl-phenyl or phenyl, the phenyl moiety being optionally substituted with one or two substituents independently selected from halo, $C_{1-4}$ alkyl, halo-substitutued $C_{1-4}$ alkyl, hydroxy, $C_{1-4}$ alkoxy, $C_{1-4}$ alkylthio, nitro, amino, di-($C_{1-4}$ alkyl)amino and CN;

X is independently selected from halo, $C_{1-4}$ alkyl, halo-substitutued $C_{1-4}$ alkyl, hydroxy, $C_{1-4}$ alkoxy, halo-substitutued $C_{1-4}$ alkoxy, $C_{1-4}$ alkylthio, nitro, amino, di-($C_{1-4}$ alkyl)amino and CN;

m is 0, 1 or 2; n is 0, 1, 2 or 3; and r is 1, 2 or 3; or (b) a compound of the formula:

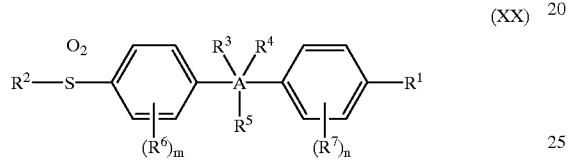

(XX)

or its pharmaceutically acceptable salt thereof, wherein the variables of formula XX are defined as follows;

A is partially unsaturated or unsaturated five membered heterocyclic, or partially unsaturated or unsaturated five membered carbocyclic, wherein the 4-(sulfonyl) phenyl and the 4-substituted phenyl in the formula (I) are attached to ring atoms of Ring A adjacent to each other;

$R^1$ is aryl or heteroaryl, and the aryl or heteroaryl being optionally substituted by one to four substituents selected from halo, $C_{1-4}$ alkyl, halo-substituted $C_{1-4}$ alkyl, $C_{1-4}$ alkoxy, $C_{1-4}$ alkyl carbonyl, hydroxy, nitro, cyano and amino, with the proviso that when A is pyrazole, $R^1$ is heteroaryl;

$R^2$ is $C_{1-4}$ alkyl, halo-substituted $C_{1-4}$ alkyl, $C_{1-4}$ alkylamino, $C_{1-4}$ dialkylamino or amino;

$R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxy, $C_{1-4}$ alkoxycarbonyl, aminocarbonyl, N—$C_{1-4}$ alkylaminocarbonyl, N,N-di-$C_{1-4}$ alkylaminocarbonyl, N-arylaminocarbonyl, N,N-diarylaminocarbonyl, N—$C_{1-4}$ alkyl-N-arylamiocarbonyl, aryl, aryloxy, aryloxy-$C_{1-4}$ alkyl, heteroaryl, heteroaryloxy, heteroaryloxy-$C_{1-4}$ alkyl, morpholino-carbonyl, $C_{1-4}$ alkoxyaminocarbonyl or $C_{1-4}$ alkyl-carbonylamino; or two of $R^3$, $R^4$ and $R^5$ are taken together with atoms to which they are attached and form a 4–7 membered ring;

$R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamino, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl, hydroxy, amino-$C_{1-4}$ alkyl and N,N-di $C_{1-4}$ alkylamino-$C_{1-4}$ alkyl; and m and n are independently 1, 2, 3 or 4, with the proviso that when A contains an oxygen or sulfur heteroatom, one of $R^3$, $R^4$ or $R^5$ is absent; or (c) a compound of the formula:

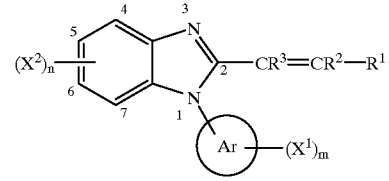

(XXX)

or a pharmaceutically acceptable salt thereof, wherein variables of formula XXX are defined as follows;

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$X^2$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N-[($C_1$–$C_4$ alkyl)sulfonyl] amino, N-[(halo-substituted $C_1$–$C_4$ alkyl)sulfonyl] amino, $C_1$–$C_4$ alkanoyl, carboxy, ($C_1$–$C_4$ alkoxy) carbonyl, carbamoyl, [N—($C_1$–$C_4$ alkyl)amino] carbonyl, [N,N-di($C_1$–$C_4$ alkyl)amino]carbonyl, N-carbamoylamino, cyano, nitro, mercapto, ($C_1$–$C_4$ alkyl)thio, ($C_1$–$C_4$ alkyl)sulfinyl, ($C_1$–$C_4$ alkyl) sulfonyl, aminosulfonyl, [N—($C_1$–$C_4$ alkyl)amino] sulfonyl and [N,N-di($C_1$–$C_4$ alkyl)amino]sulfonyl;

$R^1$ is selected from hydrogen;

straight or branched $C_1$–$C_4$ alkyl optionally substituted with one to three substituent(s) wherein said substituents are independently selected from halo, hydroxy, $C_1$–$C_4$ alkoxy, amino, N—($C_1$–$C_4$ alkyl) amino and N,N-di($C_1$–$C_4$ alkyl)amino;

$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl) amino and N,N-di($C_1$–$C_4$ alkyl)amino;

$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

phenyl optionally substituted with one to three substituent(s) wherein said substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N-[($C_1$–$C_4$ alkyl)($C_1$–$C_4$ alkanoyl)]amino, N-[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl) amino]sulfonyl; and heteroaryl selected from a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl being optionally substituted with one to three substituent(s) selected from $X^1$;

$R^2$ and $R^3$ are independently selected from:

hydrogen;

halo;

$C_1$–$C_4$ alkyl;

phenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

or $R^1$ and $R^2$ can form, together with the carbon atom to which they are attached, a $C_3$–$C_7$ cycloalkyl ring;

m is 0, 1, 2, 3, 4 or 5; and n is 0, 1, 2, 3 or 4; or (d) a compound of the formula:

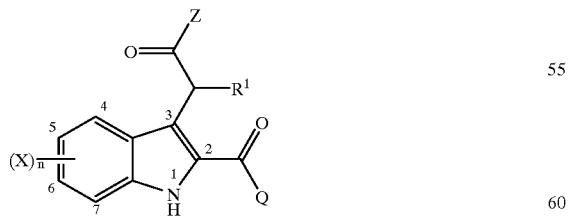

(XL)

or the pharmaceutically acceptable salts thereof wherein the variables of formula XL are as defined as follows;

Z is OH, C1-6 alkoxy, —$NR^2R^3$ or a group of the formula (II) or (III):

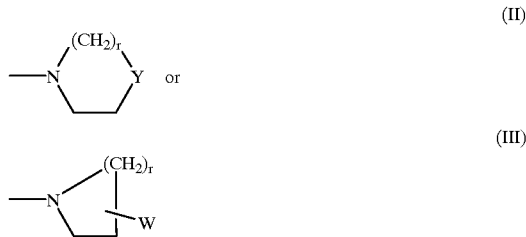

wherein r is 1, 2, 3 or 4, Y is a direct bond, O, S or NR4, and W is OH or —$NR^2R^3$;

Q is selected from the following:

(a) phenyl optionally substituted with one, two or three subsbituents independently selected from (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—(CH2)n-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

R1 is hydrogen, $C_{1-4}$ alkyl or halo;

R2 and R3 are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

R4 is hydrogen or $C_{1-4}$ alkyl;

X is independently selected from halo, $C_{1-4}$ alkyl, halo-substituted $C_{1-4}$ alkyl, H, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4; or (e) a compound of the formula:

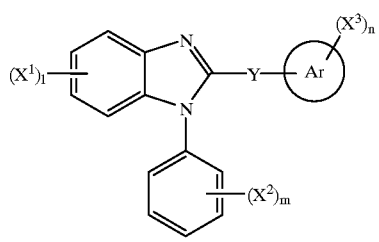

(L)

and the pharmaceutically acceptable salts thereof wherein the compounds of formula L are defined as follows;

Ar is phenyl, $C_{3-8}$ cycloalkyl, $C_{4-8}$ cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

X1 is H, halo, $C_{1-4}$ alkyl, hydroxy, $C_{1-4}$ alkoxy, halo-substituted $C_{1-4}$ alkyl, hydroxy-substituted $C_{1-4}$ alkyl, ($C_{1-4}$)alkoxy($C_{1-4}$)alkyl, amino, $C_{1-4}$ alkylamino, di($C_{1-4}$)alkylamino, amino $C_{1-4}$ alkyl, ($C_{1-4}$)alkylamino($C_{1-4}$)alkyl, di($_{1-4}$)alkylamino($C_{1-4}$)alkyl, $C_{1-4}$ alkanoylamino, di($C_{1-4}$)alkanoylamino, ($C_{1-4}$)alkyl($C_{1-4}$ alkanoyl)amino, $C_{1-4}$ alkylsulfonylamino, $C_{1-4}$ alkanoyl, carboxyl, ($C_{1-4}$) alkoxycarbonyl, aminocarbonyl, ($C_{1-4}$) alkylaminocarbonyl, di($C_{1-4}$)alkylaminocarbonyl, cyano, nitro, mercapto, $C_{1-4}$ alkylthio, $C_{1-4}$ alkylsulfinyl, $C_{1-4}$ alkylsulfonyl, aminosulfonyl, $C_{1-4}$ alkylaminosulfonyl or di($C_{1-4}$) alkylaminosulfonyl;

X2 and X3 are independently $C_{1-4}$ alkyl, halo, halo-substituted $C_{1-4}$ alkyl, hydroxy, $C_{1-4}$ alkoxy, mercapto, $C_{1-4}$ alkylthio, $C_{1-4}$ alkylsulfinyl, $C_{1-4}$ alkylsulfonyl, $C_{1-4}$ alkanoyl, carboxyl, ($C_{1-4}$) alkoxycarbonyl, aminocarbonyl, $C_{1-4}$ alkylaminocarbonyl, di($C_{1-4}$)alkylaminocarbonyl, cyano, nitro, amino, $C_{1-4}$ alkylamino, di($C_{1-4}$) alkylamino or $C_{1-4}$ alkylsulfonylamino;

Y is —CR1=CR2- or —C≡C—, wherein $R^1$ and $R^2$ are independently H, methyl, ethyl or halo;

l is 0, 1, 2, 3 or 4; and m and n are independently 0, 1, 2 or 3, with the proviso that when Ar is phenyl; and l, m and n are 0, Y is not —CH=CH—; and when Ar is phenyl; l and m are 0; n is 1; and Y is —CH=CH—, X3 is not $C_{1-4}$ alkoxy attached to the 2-position of Ar, nor amino, $C_{1-4}$ alkylamino or di($C_{1-4}$) alkylamino attached at the 4-position of Ar; or (f) a compound of the formula

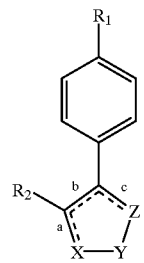

(LX)

or pharmaceutically acceptable salts thereof wherein:

X—Y—Z— is selected from the group consisting of —C(O)—O—$CR^5(R^5)$— when side b is a double bond, and sides a and c are single bonds; and $R^1$ is selected from the group consisting of
(a) $S(O)_2CH_3$,
(b) $S(O)_2NH_2$, $R^2$ is selected from the group consisting of
(a) $C_{1-6}$alkyl,
(b) $C_3$, $C_4$, $C_5$, $C_6$ and $C_7$, cycloalkyl,
(c) Heteroaryl
(d) Benzoheteroaryl
(e) Mono- or di-substituted phenyl wherein the substituent is selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-6}$alkyl-$CO_2R^5$;

$R^5$, $R^5$ and $R^6$ are each independently selected from the group consisting of
(a) hydrogen,
(b) $C_{1-6}$)alkyl,
or $R^5$ and $R^6$ together with the carbon to which they are attached from a saturated monocyclic carbon ring is 3, 4, 5, 6 or 7 atoms;

and a pharmaceutically acceptable carrier.

As used herein, "halo" is fluoro, chloro, bromo or iodo.

As used herein, the term "C1–4 alkyl" means straight or branched chain saturated radicals of 1 to 4 carbon atoms, including, but not limited to methyl, ethyl, n-propyl, isopropyl, n-butyl, isobutyl, sec-butyl, tert-butyl, and the like.

As used herein, an example of "propyl" is n-propyl and isopropyl.

As used herein, an example of "butyl" is n-butyl, isobutyl, sec-butyl and tert-butyl.

As used herein, an example of "alkoxy" is methoxy, ethoxy, n-propoxy, isopropoxy, n-butoxy, isobutoxy, sec-butoxy, tert-butoxy, and the like.

As used herein, an example of "alkylthio" is methylthio, ethylthio, n-propylthio, isopropylthio, n-butylthio, isobutylthio, sec-butylthio, tert-butylthio, and the like.

As used herein, an example of "di-(C1–4 alkyl)amino" is dimethylamino, diethylamino, dipropylamino, N-methyl-N- ethylamino, N-methyl-N-propylamino, N-methyl-N-butylamino, N-ethyl-N-propylamino, and the like.

As used herein, an example of "$C_{1-4}$ alkylamino" is methylamino, ethylamino, n-propylamino, isopropylamino, n-butylamino, isobutylamino, sec-butylamino, tert-butylamino, and the like.

As used herein, an example of "HO—(C1–4)alkyl" is hydroxymethyl, hydroxyethyl (e.g., 1-hydroxyethyl and 2-hydroxyethyl), hydroxypropyl (e.g., 1-hydroxypropyl, 2-hydroxypropyl and 3-hydroxypropyl).

As used herein, an example of "C1–4 alkoxy-C1–4 alkyl" is methoxymethyl, methoxyethyl, methoxypropyl, methoxybutyl, ethoxymethyl, ethoxyethyl, ethoxypropyl, and the like.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like.

As used herein, an example of "halo-substituted alkoxy" is chloromethoxy, dichloromethoxy, fluoromethoxy, difluoromethoxy, trifluoromethoxy, 2,2,2-trichloroethoxy, and the like.

As used herein, the term "C3–7 cycloalkyl" means carbocyclic radicals, of 3 to 7 carbon atoms, including, but not limited to cyclopropyl, cyclobutyl, cyclopentyl, cyclohexyl, cycloheptyl, and the like.

As used herein, an example of "aryl" is phenyl and naphthyl.

As used herein, a 5-membered monocyclic aromatic group usually has one heteroatom selected from O, S and N in the ring. In addition to said heteroatom, the monocyclic aromatic group may optionally have up to three N atoms in the ring. For example, the 5-membered monocyclic aromatic group includes thienyl, furyl, thiazolyl (e.g., 1,3-thiazolyl, 1,2-thiazolyl), imidazolyl, pyrrolyl, oxazolyl (e.g., 1,3-oxazolyl, 1,2-oxazolyl, isoxazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl, 1,2,3-thiadiazolyl) and the like.

As used herein, an example of a 6-membered monocyclic aromatic group includes pyridyl, pyrazinyl, pyrimidinyl, pyridazinyl, triazinyl (e.g., 1,3,5-triazinyl), tetrazinyl and the like.

As used herein, an example of a benzo-fuzed heterocycle includes quinolyl, isoquinolyl, cinnolinyl, quinoxalinyl, benzoimidazolyl, benzothiazolyl, benzoxazolyl, benzofuranyl, benzothiophenyl, indolyl, isoindolyl, 1H-indazolyl, quinazolinyl, phthalazinyl and the like.

As used herein, an example of (ethyl)(ethoxy)pyridyl includes 3-ethoxy-4-ethyl-2-pyridyl, 4-ethoxy-3-ethyl-2-pyridyl and the like.

As used herein, an example of (chloro)(ethyl)pyridyl includes 3-cloro-4-ethyl-2-pyridyl, 4-cloro-3-ethyl-2-pyridyl and the like.

As used herein, an example of (fluoro)(ethyl)phenyl includes 3-fluoro-4-ethyl-2-pyridyl, 4-fluoro-3-ethyl-2-pyridyl and the like.

This invention also relates to a method of treating migraine in a mammal, including a human, comprising administering to said mammal an amount of a pharmaceutical composition comprising a $5HT_1$ receptor agonist or a pharmaceutically acceptable salt thereof and caffeine; with (a) a compound of the formula:

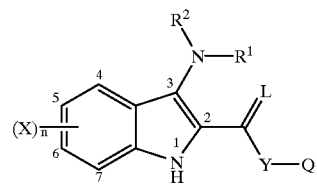

(I)

or the pharmaceutically acceptable salts thereof wherein
$R^1$ is hydrogen or $C_{1-4}$ alkyl; $R^2$ is $C(=L')R^3$ or $SO_2R^4$; Y is a direct bond or $C_{1-4}$ alkylene; L and L' are independently oxygen or sulfur;
Q is selected from the following:
(Q-a) $C_{1-6}$ alkyl,
(Q-b) halo-substituted $C_{1-4}$ alkyl,
(Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo,
(Q-d) phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy, nitro, halo-substituted $C_{1-4}$ alkoxy, $S(O)_m R^5$, $SO_2NH_2$, $SO_2N(C_{1-4}$ alkyl$)_2$, amino, $C_{1-4}$ alkylamino, di-($C_{1-4}$ alkyl)amino, $NR^1C(O)R^5$, CN, $C_{1-4}$ alkyl-OH and $C_{1-4}$ alkyl-$OR^5$,
(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$, and p2 (Q-f) a 6-membered monocyclic aromatic group containing one nitrogen atom and optionally containing one, two or three additional nitrogen atom(s), and said monocyclic aromatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$;
$R^3$ is —$OR^6$, —$NR^7R^8$, $N(OR^1)R^7$ or a group of formula:

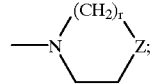

Z is a direct bond, oxygen, sulfur or $NR^5$;
$R^4$ is $C_{1-6}$ alkyl, halo-substituted $C_{1-4}$ alkyl, $C_{1-4}$ alkyl-OH, —$NR^7R^3$, phenyl or naphthyl, the phenyl and naphthyl being optionally substituted with one, two or three substituents independently selected from halo, $C_{1-4}$ alkyl, halo-substitutued $C_{1-4}$ alkyl, hydroxy, $C_{1-4}$ alkoxy and halo-substitutued $C_{1-4}$ alkoxy;

$R^5$ is $C_{1-4}$ alkyl or halo-substituted $C_{1-4}$ alkyl;

$R^6$ is $C_{1-4}$ alkyl, $C_{3-7}$ cycloalkyl, $C_{1-4}$ alkyl-$C_{3-7}$ cycloalkyl, halo-substitutued $C_{1-4}$ alkyl, $C_{1-4}$ alkyl-phenyl or phenyl, the phenyl moiety being optionally substituted with one, or two substituents independently selected from halo, $C_{1-4}$ alkyl, halo-substitutued $C_{1-4}$ alkyl, hydroxy, $C_{1-4}$ alkoxy, $C_{1-4}$ alkylthio, amino, di-($C_{1-4}$ alkyl)amino and nitro;

$R^7$ and $R^8$ are independently selected from the following:
(a) hydrogen,
(b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl)amino,
(c) $C_{3-7}$ cycloalkyl optionally substituted with a substituent independently selected from hydroxy, $C_{1-4}$ alkyl and $C_{1-4}$ alkoxy,
(d) $C_{1-4}$ alkyl-$C_{3-7}$ cycloalkyl optionally substituted with a substituent independently selected from hydroxy, $C_{1-4}$ alkyl and $C_{1-4}$ alkoxy, and
(f) $C_{1-4}$ alkyl-phenyl or phenyl, the phenyl moiety being optionally substituted with one or two substituents independently selected from halo, $C_{1-4}$ alkyl, halo-substitutued $C_{1-4}$ alkyl, hydroxy, $C_{1-4}$ alkoxy, $C_{1-4}$ alkylthio, nitro, amino, di-($C_{1-4}$ alkyl) amino and CN;

X is independently selected from halo, $C_{1-4}$ alkyl, halo-substitutued $C_{1-4}$ alkyl, hydroxy, $C_{1-4}$ alkoxy, halo-substitutued $C_{1-4}$ alkoxy, $C_{1-4}$ alkylthio, nitro, amino, di-($C_{1-4}$ alkyl)amino and CN;

m is 0, 1 or 2; n is 0, 1, 2 or 3; and r is 1,2 or 3; or
(b) a compound of the formula:

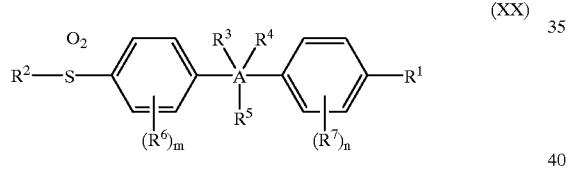

(XX)

or its pharmaceutically acceptable salt thereof, wherein the variables of formula XX are defined as follows;

A is partially unsaturated or unsaturated five membered heterocyclic, or partially unsaturated or unsaturated five membered carbocyclic, wherein the 4-(sulfonyl) phenyl and the 4-substituted phenyl in the formula (I) are attached to ring atoms of Ring A adjacent to each other;

$R^1$ is aryl or heteroaryl, and the aryl or heteroaryl being optionally substituted by one to four substituents selected from halo, $C_{1-4}$ alkyl, halo-substituted $C_{1-4}$ alkyl, $C_{1-4}$ alkoxy, $C_{1-4}$ alkyl carbonyl, hydroxy, nitro, cyano and amino, with the proviso that when A is pyrazole, $R^1$ is heteroaryl;

$R^2$ is $C_{1-4}$ alkyl, halo-substituted $C_{1-4}$ alkyl, $C_{1-4}$ alkylamino, $C_{1-4}$ dialkylamino or amino;

$R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy-$C_{1-4}$ alkyl, $C_{1-4}$ alkanoyl, cyano, nitro, cyano $C_{1-4}$ alkyl, carboxy, $C_{1-4}$ alkoxycarbonyl, aminocarbonyl, N—$C_{1-4}$ alkylaminocarbonyl, N,N-di-$C_{1-4}$ alkylaminocarbonyl, N-arylaminocarbonyl, N,N-diarylaminocarbonyl, N-$C_{1-4}$ alkyl-N-arylamiocarbonyl, aryl, aryloxy, aryloxy-$C_{1-4}$ alkyl, heteroaryl, heteroaryloxy, heteroaryloxy-$C_{1-4}$ alkyl, morpholino-carbonyl, $C_{1-4}$ alkoxyaminocarbonyl or $C_{1-4}$ alkyl-carbonylamino; or two of $R^3$, $R^4$ and $R^5$ are taken together with atoms to which they are attached and form a 4–7 membered ring;

$R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamino, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl, hydroxy, amino-$C_{1-4}$ alkyl and N,N-di $C_{1-4}$ alkylamino-$C_{1-4}$ alkyl; and m and n are independently 1, 2, 3 or 4, with the proviso that when A contains an oxygen or sulfur heteroatom, one of $R^3$, $R^4$ or $R^5$ is absent; or (c) a compound of the formula:

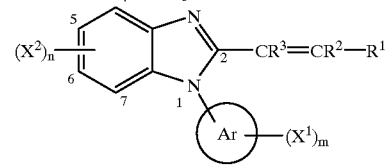

(XXX)

or a pharmaceutically acceptable salt thereof, wherein variables of formula XXX are defined as follows;

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $C_1$-$C_4$ alkyl, hydroxy, $C_1$-$C_4$ alkoxy, halo-substituted $C_1$-$C_4$ alkyl, hydroxy-substituted $C_1$-$C_4$ alkyl, ($C_1$-$C_4$ alkoxy)$C_1$-$C_4$ alkyl, halo-substituted $C_1$-$C_4$ alkoxy, amino, N—($C_1$-$C_4$ alkyl)amino, N,N-di($C_1$-$C_4$ alkyl)amino, [N—($C_1$-$C_4$ alkyl)amino]$C_1$-$C_4$ alkyl, [N,N-di($C_1$-$C_4$ alkyl)amino]$C_1$-$C_4$ alkyl, N—($C_1$-$C_4$ alkanoyl)amino, N—($C_1$-$C_4$ alkyl)-N—($C_1$-$C_4$ alkanoyl)amino, N-[($C_1$-$C_4$ alkyl)sulfonyl]amino, N—[(halo-substituted $C_1$-$C_4$ alkyl)sulfonyl]amino, $C_1$-$C_4$ alkanoyl, carboxy, ($C_1$-$C_4$ alkoxy)carbonyl, carbamoyl, [N—($C_1$-$C_4$ alkyl)amino]carbonyl, [N,N-di($C_1$-$C_4$ alkyl)amino]carbonyl, cyano, nitro, mercapto, $C_1$-$C_4$ alkyl)thio, ($C_1$-$C_4$ alkyl)sulfinyl, ($C_1$-$C_4$ alkyl)sulfonyl, aminosulfonyl, [N—($C_1$-$C_4$ alkyl)amino]sulfonyl and [N,N-di($C_1$-$C_4$ alkyl)amino]sulfonyl;

$X^2$ is independently selected from halo, $C_1$-$C_4$ alkyl, hydroxy, $C_1$-$C_4$ alkoxy, halo-substituted $C_1$-$C_4$ alkyl, hydroxy-substituted $C_1$-$C_4$ alkyl, ($C_1$-$C_4$ alkoxy)$C_1$-$C_4$ alkyl, halo-substituted $C_1$-$C_4$ alkoxy, amino, N—($C_1$-$C_4$ alkyl)amino, N,N-di($C_1$-$C_4$ alkyl)amino, [N—($C_1$-$C_4$ alkyl)amino]$C_1$-$C_4$ alkyl, [N,N-di($C_1$-$C_4$ alkyl)amino]$C_1$-$C_4$ alkyl, N—($C_1$-$C_4$ alkanoyl)amino, N—($C_1$-$C_4$ alkyl)-N—($C_1$-$C_4$ alkanoyl)amino, N-[($C_1$-$C_4$ alkyl)sulfonyl]amino, N-[(halo-substituted $C_1$-$C_4$ alkyl)sulfonyl]amino, $C_1$-$C_4$ alkanoyl, carboxy, ($C_1$-$C_4$ alkoxy)carbonyl, carbamoyl, [N—($C_1$-$C_4$ alkyl)amino]carbonyl, [N,N-di($C_1$-$C_4$ alkyl)amino]carbonyl, N-carbamoylamino, cyano, nitro, mercapto, ($C_1$-$C_4$ alkyl)thio, (C₁–C₄ alkyl)sulfinyl, (C₁–C₄ alkyl)sulfonyl, aminosulfonyl, [N—(C₁–C₄ alkyl)amino]sulfonyl and [N,N-di(C₁–C₄ alkyl)amino]sulfonyl;

R¹ is selected from hydrogen;

straight or branched C₁–C₄ alkyl optionally substituted with one to three substituent(s) wherein said substituents are independently selected from halo, hydroxy, C₁–C₄ alkoxy, amino, N—(C₁–C₄ alkyl)amino and N,N-di(C₁–C₄ alkyl)amino;

C₃–C₈ cycloalkyl optionally substituted with one to three substituent(s) wherein said substituents are independently selected from halo, C₁–C₄ alkyl, hydroxy, C₁–C₄ alkoxy, amino, N—(C₁–C₄ alkyl)amino and N,N-di(C₁–C₄ alkyl)amino;

C₄–C₈ cycloalkenyl optionally substituted with one to three substituent(s) wherein said substituents are independently selected from halo, C₁–C₄ alkyl, hydroxy, C₁–C₄ alkoxy, amino, N—(C₁–C₄ alkyl)amino and N,N-di(C₁–C₄ alkyl)amino;

phenyl optionally substituted with one to three substituent(s) wherein said substituents are independently selected from halo, C₁–C₄ alkyl, hydroxy, C₁–C₄ alkoxy, halo-substituted C₁–C₄ alkyl, hydroxy-substituted C₁–C₄ alkyl, (C₁–C₄ alkoxy)C₁–C₄ alkyl, halo-substituted C₁–C₄ alkoxy, amino, N—(C₁–C₄ alkyl)amino, N, N-di(C₁–C₄ alkyl)amino, [N—(C₁–C₄ alkyl)amino]C₁–C₄ alkyl, [N,N-di(C₁–C₄ alkyl)amino]C₁–C₄ alkyl, N—(C₁–C₄ alkanoyl)amino, N—[(C₁–C₄ alkyl)(C₁–C₄ alkanoyl)]amino, N—[(C₁–C₄ alkyl)sulfonyl]amino, N-[(halo-substituted C₁–C₄ alkyl)sulfonyl]amino, C₁–C₄ alkanoyl, carboxy, (C₁–C₄ alkoxy)carbonyl, carbamoyl, [N—(C₁–C₄ alkyl)amino]carbonyl, [N,N-di(C₁–C₄ alkyl)amino]carbonyl, cyano, nitro, mercapto, (C₁–C₄ alkyl)thio, (C₁–C₄ alkyl)sulfinyl, (C₁–C₄ alkyl)sulfonyl, aminosulfonyl, [N—(C₁–C₄ alkyl)amino]sulfonyl and [N,N-di(C₁–C₄ alkyl)amino]sulfonyl; and heteroaryl selected from a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl being optionally substituted with one to three substituent(s) selected from X¹;

R² and R³ are independently selected from:

hydrogen;

halo;

C₁–C₄ alkyl;

phenyl optionally substituted with one to three substituent(s) wherein said substituents are independently selected from halo, C₁–C₄ alkyl, hydroxy, C₁–C₄ alkoxy, amino, N—(C₁–C₄ alkyl)amino and N,N-di(C₁–C₄ alkyl)amino;

or R¹ and R² can form, together with the carbon atom to which they are attached, a C₃–C₇ cycloalkyl ring;

m is 0, 1, 2, 3, 4 or 5; and n is 0, 1, 2, 3 or 4; or (d) a compound of the formula:

(XL)

or the pharmaceutically acceptable salts thereof wherein the variables of formula XL are as defined as follows;

Z is OH, C1–6 alkoxy, —NR²R³ or a group of the formula (II) or (III):

(II)

or (III)

wherein r is 1, 2, 3 or 4, Y is a direct bond, O, S or NR4, and W is OH or —NR²R³;

Q is selected from the following:

(a) phenyl optionally substituted with one, two or three substituents independently selected from (a-1) halo, C₁₋₄ alkyl, halo-substituted C₁₋₄ alkyl, OH, C₁₋₄ alkoxy, halo-substituted C₁₋₄ alkoxy, C₁₋₄ alkylthio, NO₂, NH₂, di-(C₁₋₄ alkyl)amino, C₁₋₄ alkylamino, CN, HO—(C₁₋₄) alkyl, C₁₋₄ alkoxy-C₁₋₄ alkyl, C₁₋₄ alkylsulfonyl, aminosulfonyl, —NH₂S(O)₂NR²R³, acetyl, —COOH, —C(O)O—C₁₋₄ alkyl, C₁₋₄ alkylsulfonylamino and C₃₋₇ cycloalkyl, (a-2) aryl or —O—(CH2)n-aryl, and the aryl or aryl moiety being optionally substituted with one, two or three substituents independently selected from halo, C₁₋₄ alkyl, halo-substituted C₁₋₄ alkyl, OH, C₁₋₄ alkoxy, halo-substituted C₁₋₄ alkoxy, C₁₋₄ alkylthio, NO₂, NH₂, di-(C₁₋₄ alkyl)amino, C₁₋₄ alkylamino and CN, (a-3) 5-membered monocyclic aromatic group optionally substitued with one, two or three substituents independently selected from halo, C₁₋₄ alkyl, halo-substituted C₁₋₄ alkyl, OH, C₁₋₄ alkoxy, halo-substituted C₁₋₄ alkoxy, C₁₋₄ alkylthio, NO₂, NH₂, di-(C₁₋₄ alkyl)amino, C₁₋₄ alkylamino and CN, (a-4) 6-membered monocyclic aromatic group optionally substitued with one, two or three substituents independently selected from halo, C₁₋₄ alkyl, halo-substituted C₁₋₄ alkyl, OH, C₁₋₄ alkoxy, halo-substituted C₁₋₄ alkoxy, C₁₋₄ alkylthio, NO₂, NH₂, di-(C₁₋₄ alkyl)amino, C₁₋₄ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4), (d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

R1 is hydrogen, $C_{1-4}$ alkyl or halo;

R2 and R3 are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

R4 is hydrogen or $C_{1-4}$ alkyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4; or (e) a compound of the formula:

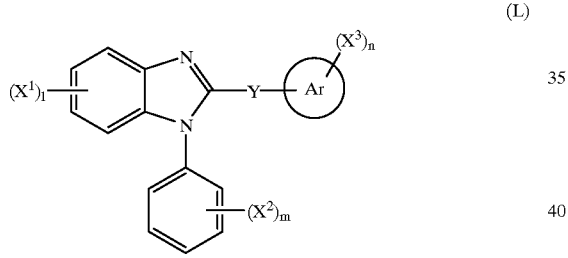

(L)

and the pharmaceutically acceptable salts thereof wherein the compounds of formula L are defined as follows;

Ar is phenyl, $C_{3-8}$ cycloalkyl, $C_{4-8}$ cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

X1 is H, halo, $C_{1-4}$ alkyl, hydroxy, $C_{1-4}$ alkoxy, halo-substituted $C_{1-4}$ alkyl, hydroxy-substituted $C_{1-4}$ alkyl, ($C_{1-4}$)alkoxy($C_{1-4}$)alkyl, amino, $C_{1-4}$ alkylamino, di($C_{1-4}$)alkylamino, amino $C_{1-4}$ alkyl, ($C_{1-4}$)alkylamino($C_{1-4}$)alkyl, di($C_{1-4}$)alkylamino($C_{1-4}$)alkyl, $C_{1-4}$ alkanoylamino, di($C_{1-4}$)alkanoylamino, ($C_{1-4}$)alkyl($C_{1-4}$ alkanoyl)amino, $C_{1-4}$ alkylsulfonylamino, $C_{1-4}$ alkanoyl, carboxyl, ($C_{1-4}$) alkoxycarbonyl, aminocarbonyl, ($C_{1-4}$) alkylaminocarbonyl, di($C_{1-4}$)alkylaminocarbonyl, cyano, nitro, mercapto, $C_{1-4}$ alkylthio, $C_{1-4}$ alkylsulfinyl, $C_{1-4}$ alkylsulfonyl, aminosulfonyl, $C_{1-4}$ alkylaminosulfonyl or di($C_{1-4}$) alkylaminosulfonyl;

X2 and X3 are independently $C_{1-4}$ alkyl, halo, halo-substituted $C_{1-4}$ alkyl, hydroxy, $C_{1-4}$ alkoxy, mercapto, $C_{1-4}$ alkylthio, $C_{1-4}$ alkylsulfinyl, $C_{1-4}$ alkylsulfonyl, $C_{1-4}$ alkanoyl, carboxyl, ($C_{1-4}$) alkoxycarbonyl, aminocarbonyl, $C_{1-4}$ alkylaminocarbonyl, di($C_{1-4}$)alkylaminocarbonyl, cyano, nitro, amino, $C_{1-4}$ alkylamino, di($C_{1-4}$) alkylamino or $C_{1-4}$ alkylsulfonylamino;

Y is —CR1=CR2— or —C≡C—, wherein $R^1$ and $R^2$ are independently H, methyl, ethyl or halo;

l is 0, 1, 2, 3 or 4; and m and n are independently 0, 1, 2 or 3, with the proviso that when Ar is phenyl; and l, m and n are 0, Y is not —CH=CH—; and when Ar is phenyl; l and m are 0; n is 1; and Y is —CH=CH—, X3 is not $C_{1-4}$ alkoxy attached to the 2- position of Ar, nor amino, $C_{1-4}$ alkylamino or di($C_{1-4}$) alkylamino attached at the 4-position of Ar; or (f) a compound of the formula

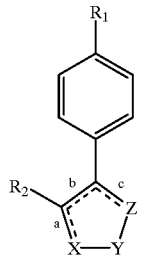

(LX)

or pharmaceutically acceptable salts thereof wherein:

X—Y—Z— is selected from the group consisting of —C(O)—O—$CR^5(R^5)$— when side b is a double bond, and sides a and c are single bonds; and $R^1$ is selected from the group consisting of (c) $S(O)_2CH_3$, (d) $S(O)_2NH_2$, $R^2$ is selected from the group consisting of (e) $C_{1-6}$alkyl, (f) $C_3$, $C_4$, $C_5$, $C_6$ and $C_7$, cycloalkyl, (g) Heteroaryl (h) Benzoheteroaryl (e) Mono- or di-substituted phenyl wherein the substituent is selected from the group consisting of

(14) hydrogen,

(15) halo,

(16) $C_{1-6}$alkoxy,

(17) $C_{1-6}$alkylthio,

(18) CN,

(19) $CF_3$,

(20) $C_{1-6}$alkyl,

(21) $N_3$,

(22) —$CO_2H$,

(23) —$CO_2$—$C_{1-4}$alkyl,

(24) —$C(R^5)(R^6)$—OH,

(25) —$C(R^5)(R^6)$—O—$C_{1-4}$alkyl, and

(26) —$C_{1-6}$alkyl-$CO_2R^5$;

$R^5$, $R^5$ and $R^6$ are each independently selected from the group consisting of (c) hydrogen, (d) $C_{1-6}$)alkyl, or $R^5$ and $R^6$ together with the carbon to which they are attached from a saturated monocyclic carbon ring is 3, 4, 5, 6 or 7 atoms;

and a pharmaceutically acceptable carrier, that is effective in treating migraine.

This invention also relates to a method of treating migraine in a mammal, including a human, comprising administering to said mammal a $5HT_1$ receptor agonist, or a pharmaceutically acceptable salt thereof, caffeine and a cyclooxygenase-2 (COX-2) inhibitor in amounts that render the combination of such three active agents effective in the treatment or prevention of migraine.

Preferred embodiments of this invention relate to pharmaceutical compositions for the treatment of migraine and methods of treating migraine, as described above, wherein the $5HT_1$ receptor agonist is selected from eletriptan, naratriptan, rizatriptan, sumatriptan almotriptan, avitriptan, frovatriptan, alniditan, zolmitriptan, LY 334370, LY 306258, BMS-180048 and BMS-181885.

Other embodiments of this invention relate to pharmaceutical compositions for the treatment of migraine and methods of treating migraine, as described above, wherein the $5HT_1$ receptor agonist is a compound of the formula

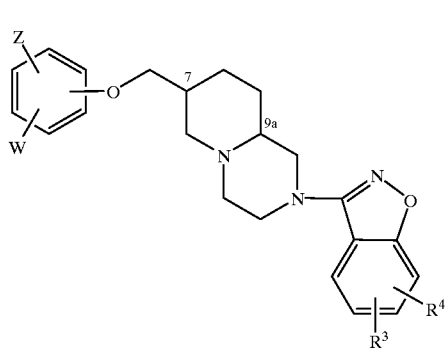

(I)

wherein $R^3$, $R^4$, and Z are selected, independently, from hydrogen, halo (e.g., chloro, fluoro, bromo or iodo), $(C_1-C_4)$alkyl optionally substituted with from one to three fluorine atoms, $(C_1-C_4)$alkoxy optionally substituted with from one to three fluorine atoms, and $(C_1-C_4)$alkoxy-$(C_1-C_4)$alkyl wherein each of the alkyl moieties may optionally be substituted with from one to three fluorine atoms;

W is —$CH_2$—O—$(C_1-C_6)$alkyl wherein the alkyl moiety can be straight or branched;

or W is —$CH_2NR^1R^2$ wherein $R^1$ and $R^2$ are independently selected from hydrogen and straight or branched $(C_1-C_6)$alkyl;

or $R^1$ and $R^2$, together with the nitrogen to which they are attached, form a saturated four membered monocyclic ring or a saturated or unsaturated nonaromatic five to seven membered monocyclic ring or a saturated or unsaturated nonaromatic seven to ten membered bicyclic ring which may optionally contain one or two heteroatoms in addition to the nitrogen of $NR^1R^2$, wherein said heteroatoms are independently selected from oxygen, nitrogen and sulfur, and wherein from one to three of the ring carbon atoms, or one of the ring nitrogen atoms, may optionally and independently be substituted with straight or branched $(C_1-C_4)$alkyl, straight or branched $(C_1-C_6)$ alkoxy, straight or branched $(C_1-C_3)$alkyl-$(C_3-C_7)$ cycloalkyl, hydroxy, amino, cyano, halo, aryl-(straight or branched $(C_1-C_3)$alkyl) or heteroaryl-(straight or branched $(C_1-C_3)$alkyl), wherein said aryl is selected from phenyl and naphthyl and said heteroaryl is selected from oxazolyl, isoxazoyl, thiazolyl, isothiazolyl, furanyl, pyrazolyl, pyrrolyl, tetrazolyl, triazolyl, thienyl, imidazolyl, pyrazinyl, pyrazolyl, indolyl, isoindolyl, pyrazinyl, cinnolinyl, pyridinyl and pyrimidinyl;

with the proviso that in any ring formed by $NR^1R^2$: (a) there can be no more than one ring oxygen atom; (b) there can be no hydroxy, alkoxy, alkoxyalkyl, cyano, amino or alkylamino moiety bonded directly to any ring nitrogen atom; and (c) no ring carbon that is double bonded to another ring carbon and not part of an aromatic ring system can be bonded to a ring oxygen atom or ring nitrogen atom;

or a pharmaceutically acceptable salt thereof.

DETAILED DESCRIPTION OF THE INVENTION

The following patents and patent applications exemplify $5HT_1$ agonists that can be used, in combination with caffeine and a cyclooxygenase-2 (COX-2) inhibitor in the pharmaceutical compositions and methods of this invention, and refer to methods of preparing the same: U.S. Pat. No. 5,545,644, issued Aug. 13, 1996; European Patent 776,323, granted Feb. 11, 1998; U.S. Pat. No. 5,618,834, issued Apr. 8, 1997; World Patent Application PCT/EP98/04176, which designates the U.S. and was filed on Jul. 1, 1998; European Patent 503,440, granted Jun. 18, 1998; U.S. Pat. No. 4,816, 470, issued Mar. 28, 1989; Japanese Patent 9,423,197, granted Mar. 30, 1994; Canadian Patent 1,241,004, granted Aug. 23, 1988; European Patent 497,512, granted Sep. 24, 1997; U.S. Pat. No. 5,300,506, issued Apr. 15, 1 994; European Patent Application 711,769, published May 15, 1996; World Patent Application WO 94/2460, published Feb. 3, 1994; U.S. Pat. No. 5,541,180, issued Jul. 30, 1996; European Patent Application 591,280, published Apr. 13, 1994; European Patent 639,192, granted May 15, 1996; European Patent Application 674,621, published Oct. 4, 1995 and European Patent 486,666, granted Aug. 13, 1997. The foregoing patents and patent applications are incorporated herein by reference in their entireties.

The following references relate to the pharmacological properties of certain of the $5HT_1$ agonists mentioned above as being employed in preferred embodiments of this invention: Robert et al., *Cephalagia* 18(6): 406, July/August 1998; Marathe et al., *Biopharm. Drug Dispos.* 19(6): 381–94, September 1998; Saxena et al., *Eur. J. Pharmacol.* 351(3): 329–39, Jun. 26, 1998; Goldstein et al., *Cephalagia* 18(6): 410, July/August 1998; Buchan et al., *Cephalagia* 18(6): 410, July/August 1998; Block et al., *Cephalagia* 18(6): 409–10, July/August 1998; and Sheftell et al., *Cephalagia* 18(6): 403–4, July/August 1998; Perry et al., *Drugs* (New Zealand) 55(6):889–922, June 1998; Bomhof et al., *Cephalagia* (Norway) 18(1): 33–7, January 1998; Klasson et al., *Headaches* (United States) 37(10): 640–5, November/ December 1997; Goldstein et al., *Cephalagia* (Norway) 16(7): 497–502, November 1996; Parsons et al., *J. Cardiovasc. Pharmacol.* (United States) 32(2): 220–4, August 1998; and Schoenen J., *Curr. Opin. Neurol.* 10(3): 237–43, June 1997. These references are incorporated herein by reference in their entireties.

The following patents and patent applications exemplify cyclooxygenase-2 (COX-2) inhibitors that can be used, in combination with a $5HT_1$ agonists and caffeine, in the pharmaceutical compositions and methods of this invention, and refer to methods of preparing the same: U.S. Pat. No. 5,817,700, issued Oct. 6, 1998; World Patent Application WO97/28121, published Aug. 7, 1997; U.S. Pat. No. 5,767, 291, issued Jun. 16, 1998; U.S. Pat. No. 5,436,265, issued Jul. 25 1995; U.S. Pat. No. 5,474,995, issued Dec. 12, 1995; U.S. Pat. No. 5,536,752, issued Jul. 16, 1996; U.S. Pat. No. 5,550,142, issued Aug. 27, 1996; U.S. Pat. No. 5,604,260, issued Feb. 18, 1997; U.S. Pat. No. 5,698,584, issued Dec. 16, 1997; U.S. Pat. No. 5,710,140, issued Jan. 20, 1998; U.S. Pat. No. 5,840,746, issued Nov. 24, 1998; Great Britain Patent Application 986430, filed Mar. 25, 1998; World Patent Application WO97/28120, published Aug. 7, 1997; Great Britain Patent Application 9800689, filed Jan. 14, 1998; Great Britain Patent Application 9800688, filed Jan. 14, 1998; World Patent Application WO94/14977, published Jul. 7, 1994; World Patent Application WO98/43966, published Oct. 8, 1998; World Patent Application WO98/03484, published Jan. 29, 1998; World Patent Application WO98/41516, published Sep. 24, 1998; World Patent Application WO98/41511, published Sep. 24, 1998; Great Britain Patent Application 2,319,032, issued May 13, 1998; World Patent Application WO96/37467, published Nov. 28, 1996; World Patent Application WO96/37469, published Nov. 28, 1996; World Patent Application WO96/36623, published Nov. 21, 1996; World Patent Application WO98/00416, published Jan. 8, 1998; World Patent Application WO97/44027, published Nov. 27, 1997; World Patent Application WO97/44028, published Nov. 27, 1997; World Patent Application WO96/23786, published Aug. 8, 1996; World Patent Application WO97/40012, published Oct. 30, 1997; World Patent Application WO96/19469, published Jun. 27, 1996; World Patent Application WO97/36863, published Oct. 9, 1997; World Patent Application WO97/14691, published Apr. 24, 1997; World Patent Application WO97/11701, published Apr. 3, 1997; World Patent Application WO96/13483, published May 9, 1996; World Patent Application WO96/37468, published Nov. 28, 1996; World Patent Application WO96/06840, published Mar. 7, 1996; World Patent Application WO94/26731, published Nov. 24, 1994; World Patent Application WO94/20480, published Sep. 15, 1994; U.S. Pat. No. 5,006,549, issued Apr. 9, 1991; U.S. Pat. No. 4,800,211, issued Jan. 24, 1989; U.S. Pat. No. 4,782,080, issued Nov. 1, 1988; U.S. Pat. No. 4,720,503, issued Jan. 19, 1988; U.S. Pat. No. 4,760,086, issued Jul. 26, 1988; U.S. Pat. No. 5,068,248, issued Nov. 26, 1991; U.S. Pat. No. 5,859,257, issued Jan. 12, 1999; World Patent Application WO98/47509, published Oct. 29, 1998; World Patent Application WO98/47890, published Oct. 29, 1998; World Patent Application WO98/43648, published Oct. 8,1998; World Patent Application WO98/25896, published Jun. 18, 1998; World Patent Application WO98/22101, published May 28, 1998; World Patent Application WO98/16227, published Apr. 23, 1998; World Patent Application WO98/06708, published Feb. 19, 1998; World Patent Application WO97/38986, published Oct. 23, 1997; U.S. Pat. No. 5,663,180, issued Sep. 2, 1997; World Patent Application WO97/29776, published Aug. 21, 1997; World Patent Application WO97/29775, published Aug. 21, 1997; World Patent Application WO97/29774, published Aug. 21, 1997; World Patent Application WO97/27181, published Jul. 31, 1997; World Patent Application WO95/11883, published May 4, 1995; World Patent Application WO97/14679, published Apr. 24, 1997; World Patent Application WO97/11704, published Apr. 3, 1997; World Patent Application WO96/41645, published Dec. 27, 1996; World Patent Application WO96/41626, published Dec. 27, 1996; World Patent Application WO96/41625, published Dec. 27, 1996; World Patent Application WO96/38442, published Dec. 5, 1996; World Patent Application WO96/38418, published Dec. 5, 1996; World Patent Application WO96/36617, published Nov. 21, 1996; World Patent Application WO96/24585, published Aug. 15, 1996; World Patent Application WO96/24584, published Aug. 15, 1996; World Patent Application WO96/16934, published Jun. 6, 1996; World Patent Application WO96/03385, published Feb. 8, 1996; World Patent Application WO96/12703, published May 2, 1996; World Patent Application WO96/09304, published Mar. 28, 1996; World Patent Application WO96/09293, published Mar. 28,1996; World Patent Application WO96/03392, published Feb. 8, 1996; World Patent Application WO96/03388, published Feb. 8, 1996; World Patent Application Application WO96/03387, published Feb. 8, 1996; World Patent Application WO96/02515, published Feb. 1, 1996; World Patent Application WO96/02486, published Feb. 1, 1996; U.S. Pat. No. 5,476,944, issued Dec. 19, 1995; World Patent Application WO95/30652, published Nov. 16, 1995; U.S. Pat. No. 5,451,604, published Sep. 19, 1995; World Patent Application WO95/21817, published Aug. 17, 1995; World Patent Application WO95/21197, published Aug. 10, 1995; World Patent Application WO95/15315, published Jun. 8, 1995; U.S. Pat. No. 5,504,215, issued Apr. 2, 1996; U.S. Pat. No. 5,508,426, issued Apr. 16, 1996; U.S. Pat. No. 5,516,907, issued May 14, 1996; U.S. Pat. No. 5,521,207, issued May 28, 1998; U.S. Pat. No. 5,753,688, issued May 19, 1998; U.S. Pat. No. 5,760,068, issued Jun. 2, 1998; U.S. Pat. No. 5,420,343, issued May 30, 1995; World Patent Application WO95/30656, published Nov. 16, 1995; U.S. Pat. No. 5,393,790, issued Feb. 28, 1995; and World Patent Application WO94/27980, published Feb. 8, 1994. The foregoing patents and patent applications are incorporated herein by reference in their entireties.

A compound of general formula (I) may be prepared by any synthetic procedure applicable to structure-related compounds known to those skilled in the art. The following representative examples as described hereinafter are illustrative of the invention in which, unless otherwise stated, L, Q, X, Y, $R^1$, $R^2$ and n are as defined herein before.

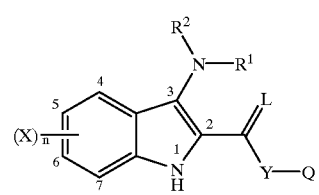

(I)

In one embodiment, a compound of the formula (IV) is prepared according to the reaction steps outlined in Scheme 1.

SCHEME 1

METHOD A

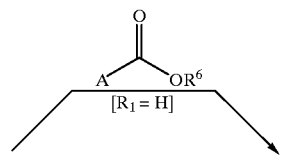

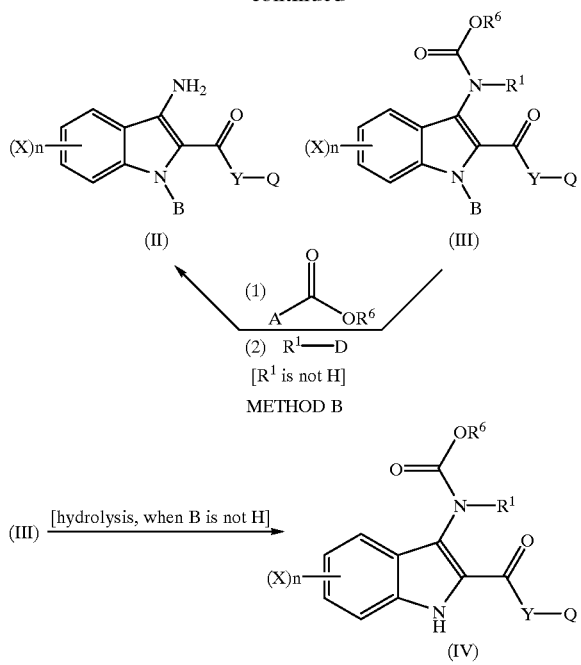

(2) R¹—D
[R¹ is not H]
METHOD B

In Scheme 1, B is hydrogen or a suitable protecting group, for example, methoxycarbonyl, ethoxycarbonyl, tert-butoxycarbonyl (Boc), benzyloxycarbonyl, phenylsulfonyl or p-toluenesulfonyl, or the like. The group $R^1$, $R^6$, X, Y, Q and n are as defined as herein before.

For example, Method A or in step 1 of Method B, a compound of formula (II) is reacted with a compound of formula $R^6OC(O)$—A wherein A is defined such that the compound of $R^6OC(O)$—A is, for example, a carboxylic acid chloride, a carboxylic acid, a carboxylic acid ester, a carboxylic acid anhydride, or the like. In the instant example, when a compound of formula $R^6OC(O)$—A is, for example, a carboxylic acid chloride or carboxylic acid anhydride the reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, or the like. Preferably, the reaction conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

Alternatively, when a compound of formula $R^6C(O)$—A is, for example, a carboxylic acid, the intermediate amide obtained from either Method A or step 1 in Method B can be readily prepared by treating the requisite carboxylic acid with a compound of formula (II) in the presence of a coupling reagent such as, but not limited to, 1-(dimethylaminopropyl)-3-ethylcarbodiimide (WSC), N,N'-dicyclohexylcarbodiimidazole (DCC), carbonyldiimidazole, cyanophosphonic acid diethyl ester, or the like. Preferred reaction inert solvents include, but are not limited to, acetone, acetonitrile, dichloromethane, 1,2-dichloroethane, N,N-dimethylformamide, N,N-dimethylacetamide, dimethylsulfoxide, dioxane, tetrahydrofuran or pyridine. Or, for example, under Mitsunobu-type reaction conditions. A suitable condensing reagent in the Mitsunobu reaction is a di-($C_{1-4}$)alkyl azodicarboxylate in the presence of a triarylphosphine, for example, diethyl azodicarboxylate in the presence of triphenylphosphine. Reaction inert solvents of choice include tetrahydrofuran, dichloromethane, dimethylformamide, benzene, toluene, or the like. The reaction temperature is preferably in the range of 0° C. to reflux temperature of the solvent, e.g. 0 to 100° C., but if necessary, temperatures lower or higher can be adopted. Reaction times are, in general, from several minutes to a day, preferably from 20 minutes to 5 hours, however shorter or longer reaction times, if necessary, can be employed.

In step 2 of Method B, the intermediate amide (the group B is a suitable protecting group as defined herein above) is reacted with a compound of formula $R^1$—D wherein D is a selected from a suitable displaceable group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of −100 to 250° C., usually in the range of 0° C to reflux temperature of solvent, but if necessary, lower or higher temperature can be employed. Reaction time is in general from several minutes to a day, preferably from 30 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

A compound of formula (IV) may also be prepared according to the reaction step outlined in Scheme 2.

SCHEME 2

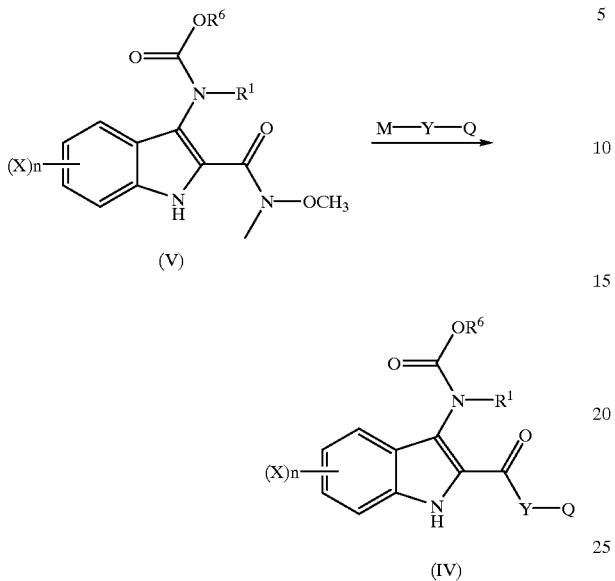

SCHEME 3

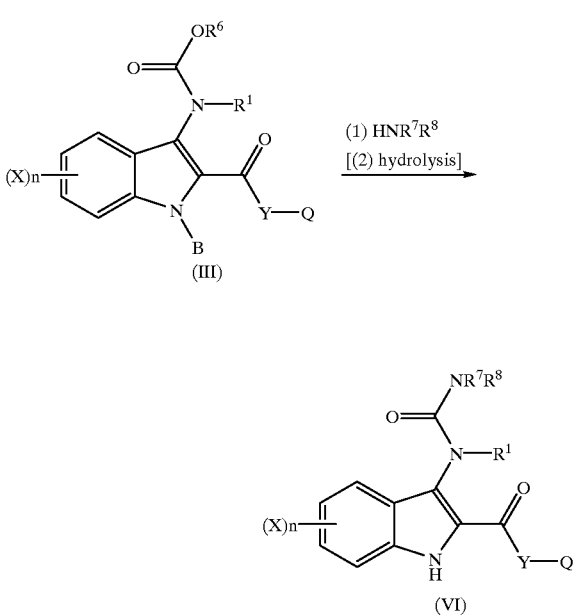

In Scheme 2, X, Y, Q, $R^1$, $R^6$ and n are as defined herein before. The compound of formula (V) (amide) is used for illustrative purposes only and is not meant to limit the scope of the present invention. Thus, for example, a compound of formula (V) is treated with a compound of formula M—Y—Q in a reaction inert solvent. In a compound of formula M—Y—Q, M is defined such that compound of formula M—Y—Q is, for example, the corresponding Grignard or alkali metal reagent, for example, M may be magnesium chloride (Q—Y—MgCl), magnesium bromide (Q—Y—MgBr), or magnesium iodide (Q—Y—MgI), lithium (Q—Y—Li), potassium (Q—Y—K) or sodium (Q—Y—Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof. Reaction temperatures are preferably in the range of −100 to 150° C., usually in the range of −70° C. to reflux temperature of solvent, preferably, −40 ° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula (V) is readily accessible by conventional synthetic methods known to those skilled in the art and, of which, are adequately described within the accompanying non-limiting examples.

In another embodiment, compounds of the formula (VI), compounds of formula (VII) and compounds of formula (IX), wherein $R^1$, $R^6$, $R^7$, $R^8$, X, Y, Q, n and r are as defined as herein before, B is a suitable protecting group as herein before, are prepared according to the reaction steps outlined in Scheme 3.

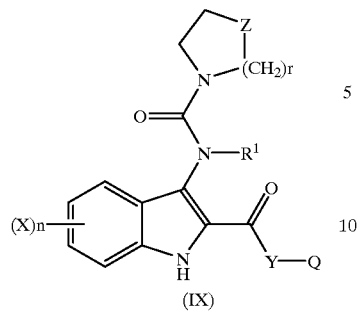

(IX)

For example, a compound of formula (III) is reacted with a compound of formula $HNR^7R^8$, a compound of formura $HN(OR^1)R^7$, or a compound of formura (VIII). The reactants may be heated together in the absence or presence of a reaction inert solvent. Preferred reaction inert solvents include, but are not limited to, benzene, toluene, xylene, o-dichlorobenzene, nitrobenzene, pyridine, 1,2-dichloroethane, dichloromethane, acetonitrile, dioxane, N,N-dimethylformamide, or the like. If necessary, the reaction conducted in the presence of base. A preferred base is selected from, for example, but not limited to, an alkali or alkaline earth metal hydroxide or carbonate such as sodium hydroxide, potassium hydroxide, sodium carbonate, potassium carbonate, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof. Reaction temperatures are generally in the range of –100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

When the group B is a suitable protecting group as defined herein above, if necessary, the group B may be removed by a number of standard procedures known to those skilled in the art (for example, see "Protection of the Amino Group", in Protective Groups in Organic Synthesis, 2nd Edition, T. W. Greene and P. G. M. Wuts, Ed., John Wiley and Sons, Inc. 1991, pp. 309–405).

In another embodiment, compounds of the formula (X) and compounds of formura (XI), wherein $R^8$, X, Y, Q and n are as defined as herein before, B is a suitable protecting group as herein before, are prepared according to the reaction steps outlined in Scheme 4.

SCHEME 4

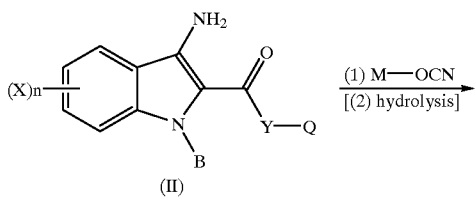

(II)

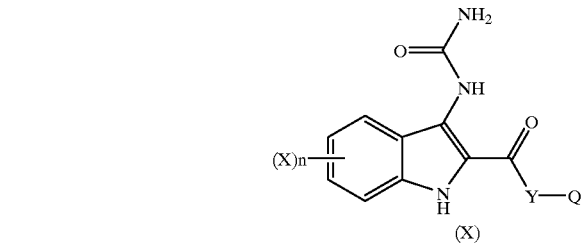

For example, a compound of formula (II) is reacted with a compound of formula M—OCN, or a compound of formula $R^8NCO$. In a compound of formula M-OCN, M is defined such that compound of formula M—OCN is, for example, the corresponding alkali or alkaline earth metal reagent, for example, M may be sodium, pottasium.

The reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, dichloromethane, or the like. Reaction temperatures are generally in the range of –100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

In another embodiment, a compound of the formula (XIII) is prepared according to the reaction steps outlined in Scheme 5.

SCHEME 5

METHOD A

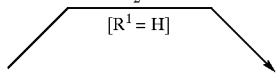

$[R^1 = H]$

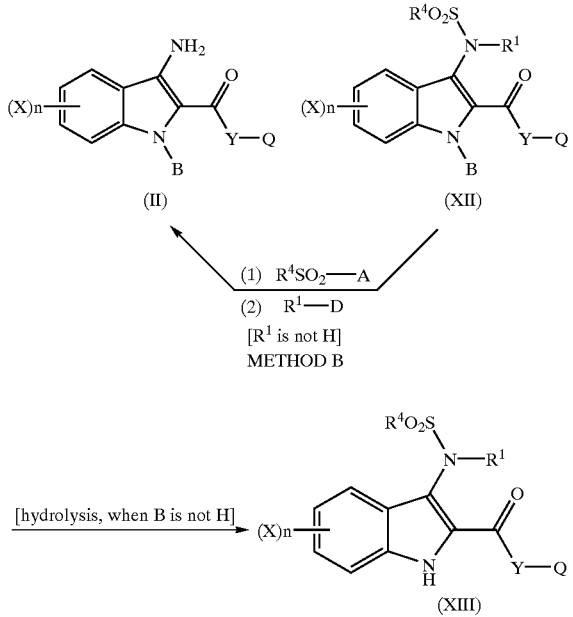

[R¹ is not H]
METHOD B

[hydrolysis, when B is not H]

(XIII)

In Scheme 5, B is hydrogen or a suitable protecting group, for example, methoxycarbonyl, ethoxycarbonyl, tert-butoxycarbonyl (Boc), or benzyloxycarbonyl, or the like. The group Q, X, R¹ and n are defined as herein before.

For example, Method A or in step 1 of Method B, a compound of formula (II) is reacted with a compound of formula $R^4SO_2$—A wherein A is defined such that the compound of $R^4SO_2$—A is, for example, a sufonic acid chloride, a sulfonic acid anhydride, or the like. In the instant example, when a compound of formula $R^4SO_2$—A is, for example, a sulfonic acid chloride the reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, or the like. Preferably, the reaction is conducted in the presence of a base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof. Reaction temperatures are generally in the range of –100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed. Under the reaction conditions described herein above, the intermediate indole may be isolated as either the mono-substituted sulfonylamino- or di-substituted sulfonylamino-intermediate, or mixtures thereof, and as such, is preferably used in the next step without isloation.

In step 2 of Method B, the intermediate amide (the group B is a suitable protecting group as defined herein above) is reacted with a compound of formula R¹—D wherein D is a selected from a suitable displaceable group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of –100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405). Under these reaction conditions, facile cleavage of one of the sulfonyl groups of the di-substituted sulfonylamino- intermediate occurs concomitantly.

A compound of formula (XIII) may also be prepared according to the reaction step outlined in Scheme 6.

SCHEME 6

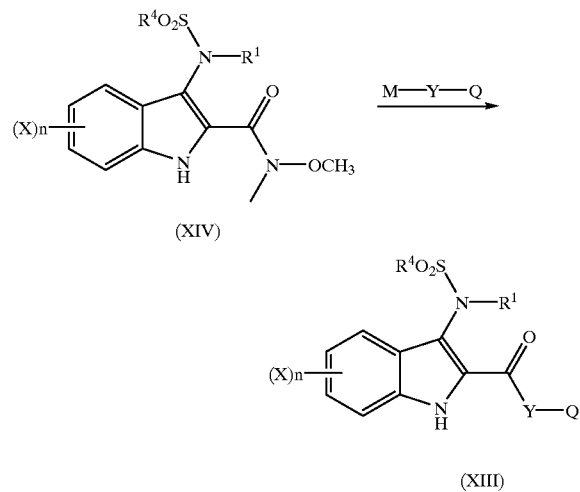

In Scheme 6, X, Q, R¹, R⁴ and n are as defined herein before. The compound of formula (XIV) (amide) is used for illustrative purposes only and is not meant to limit the scope of the present invention. Thus, for example, a compound of formula (XIV) is treated with a compound of formula M—Y—Q in a reaction inert solvent. In a compound of formula M—Y—Q, M is defined such that compound of formula M—Y—Q is, for example, the corresponding Grignard or alkali metal reagent, for example, M may be magnesium chloride (Q—Y—MgCl), magnesium bromide (Q—Y—MgBr), or magnesium iodide (Q—Y—MgI), lithium (Q—Y—Li), potassium (Q—Y—K) or sodium (Q—Y—Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof. Reaction temperatures are preferably in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula (XIV) is readily accessible by conventional synthetic methods known to those skilled in the art and, of which, are adequately described within the accompanying non-limiting examples.

A compound of formula (II) may be prepared by a number of synthetic procedures known to those skilled in the art. The following representative examples as described hereinafter are illustrative and are not meant to limit the scope of the invention in anyway.

For example, a compound of formula (II), wherein B, X, Y, Q and n are as defined as herein before, is readily accessible from the appropriate 2-aminobenzonitrile (XV) as illustrated in Scheme 7 (For example, see E. E. Garcia, L. E. Benjamin and R. Ian Fryer, *J. Heterocycl. Chem.*, 10, 51 (1973)).

SCHEME 7

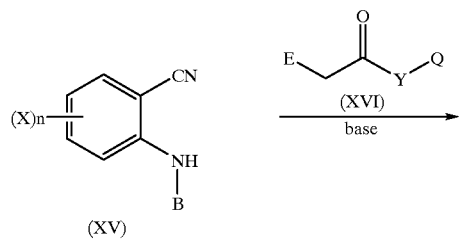

(XV)

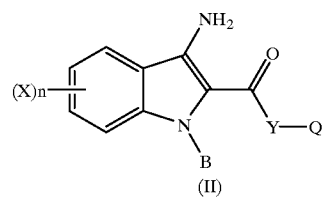

(II)

Thus, the requisite 2-aminobenzonitrile (XV) is reacted with a compound of formula (XVI), wherein Y and Q are as defined as herein before and E is halo, preferably, iodo, bromo or chloro, in the presence of a suitable base. A suitable base is, for example, an alkali or alkaline earth metal alkoxide, carbonate, or hydride, such as, but not limited to, sodium tert-butoxide, potassium tert-butoxide, sodium carbonate, potassium carbonate, sodium hydride or potassium hydride. Preferred reaction inert solvents include, but are not limited to, acetonitrile, N,N-dimethylformamide, N,N-dimethylacetamide, dimethylsulfoxide, dioxane or tetrahydrofuran. Reaction temperatures are preferably in the range of −40 to 250° C., usually in the range of 0° C. to reflux temperature of solvent, but it necessary, lower or higher temperature can be employed. Reaction time is in general from several minutes to a day, preferably from 30 minutes to 5 hours, however shorter or longer reaction times, if necessary, can be employed.

Alternatively, a compound of formula (II), wherein X, Y, Q and n are as defined as herein before and B is hydrogen, may be prepared according to the reaction steps depicted in Scheme 8.

SCHEME 8

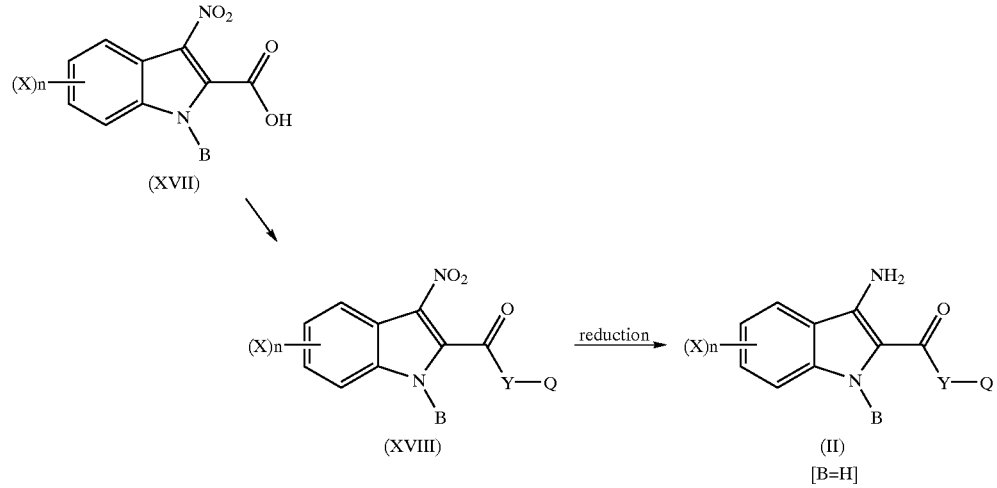

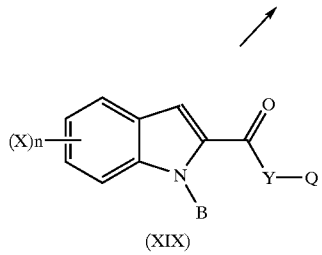

(XIX)

For example, the compound of formula (II) may be prepared from the requisite nitro compound of formula (XVIII) by reduction in the presence of suitable reducing agent by conventional methods known to those skilled in the art. For example, tin(II) chloride in ethanol (F. D. Bellamy and K. Ou, *Tetrahedron Lett.*, 25, 839 (1984)), iron-ammonium chloride in aqueous ethanol (K. Ramadas and N. Srinivasan, *Synth. Commun.*, 22, 3189 (1992)), or zinc dust or iron in acetic acid (E. Wertheim, *Org. Synth. Coll. Vol. 2.*, 160 (1943)), or by catalytic hydrogenolysis. Preferred catalysts are, for example, palladium-on-charcoal or Raney-Nickel (C. F. H. Allen and J. Vanallan, *Org. Synth. Coll. Vol.* 3., 63 (1955)). The nitro compound of formula (XVIII) is readily accessible by conventional synthetic methods known to those skilled in the art and, of which, are adequately described within the accompanying non-limiting examples.

The starting material of the formulae in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds described herein contain one or more asymmetric centers and are capable of existing in various stereoisomeric forms. The present invention contemplates all such possible stereomers as well as their racemic and resolved, enantiomerically pure forms and pharmaceutically acceptable salts thereof.

Certain compounds of the present invention are capable of forming addition salts with inorganic or organic acids. The pharmaceutically acceptable acid salts of the compounds of formula (I) are those which form non-toxic addition salts, such as, but not limited to, the hydrochloride, hydrobromide, sulfate or bisulfate, acetate, benzoate, besylate, citrate, fumarate, glucuronate, hippurate, lactate, tartrate, saccharate, succinate, maleate, methanesulfonate, p-toluenesulfonate, phosphate and pamoate (i.e., 4,4'-methylene-bis-(3-hydroxy-2-naphthoate)) salts. The pharmaceutically acceptable acid salts may be prepared by conventional techniques.

Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkaline or alkaline earth metal (sodium, potassium, calcium and magnesium) hydroxide or alkoxide in water or an appropriate organic solvent such as ethanol, isopropanol, mixtures thereof, or the like.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. When the compounds of the formula (I) of this invention may form solvates such as hydrates, such solvates are included within the scope of this invention.

An example of prodrug of the compound of formula (I) is a compound of the formula (I), wherein the 1st position of indole ring is substituted with a group selected from hydroxymethyl, —C(O)—$C_{1-4}$ alkyl, —C(O)—(NH$_2$)CH—($C_{1-4}$ alkyl), —C(O)-phenyl, —CH$_2$NHC(O)-aryl, —CH$_2$—$C_{1-4}$alkyl-O—C(O)—$C_{1-4}$alkyl, —$C_{1-4}$ alkyl-pyridyl, —C(O)CH$_2$NR$_2$ and —CH$_2$N($C_{1-4}$ alkyl)$_2$.

Another example of prodrug of the compound of formula (I) is a compound of the formula (I), wherein the carboxyl group is substituted with a group selected from $C_{1-4}$ alkyl, —CH$_2$—$C_{1-4}$alkyl-O—C(O)—$C_{1-4}$alkyl, —CH$_2$—$C_{1-4}$alkyl-O—C(O)—N($C_{1-4}$alkyl)$_2$, —CH$_2$C(O)—N($C_{1-4}$ alkyl)$_2$, —CH$_2$—$C_{1-4}$alkyl-O—C(O)—O—$C_{1-4}$alkyl, ethyl-OH and —CH$_2$CO$_2$H.

The compounds of general formula (XX) can be prepared by a variety of synthetic routes. The following representative examples as described hereinafter are illustrative and are not meant to limit the scope of the invention in anyway. Unless otherwise stated, A, R$^1$, R$^2$, R$^3$, R$^4$, R$^5$, R$^6$ and R$^7$ are as defined herein before.

1) Synthesis of Compound (XX) by A Ring Formation

Compound (I) can be synthesized by a variety of A ring formation methods.

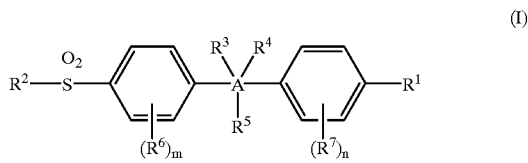

(I)

Pyrazole

When A is a pyrazole ring, the pyrazole (Ia) can be prepared from an appropriate 1,3-diketone or its equivalents (2 or 3) and phenylhydrazine (4), as shown in scheme 9.

SCHEME 9

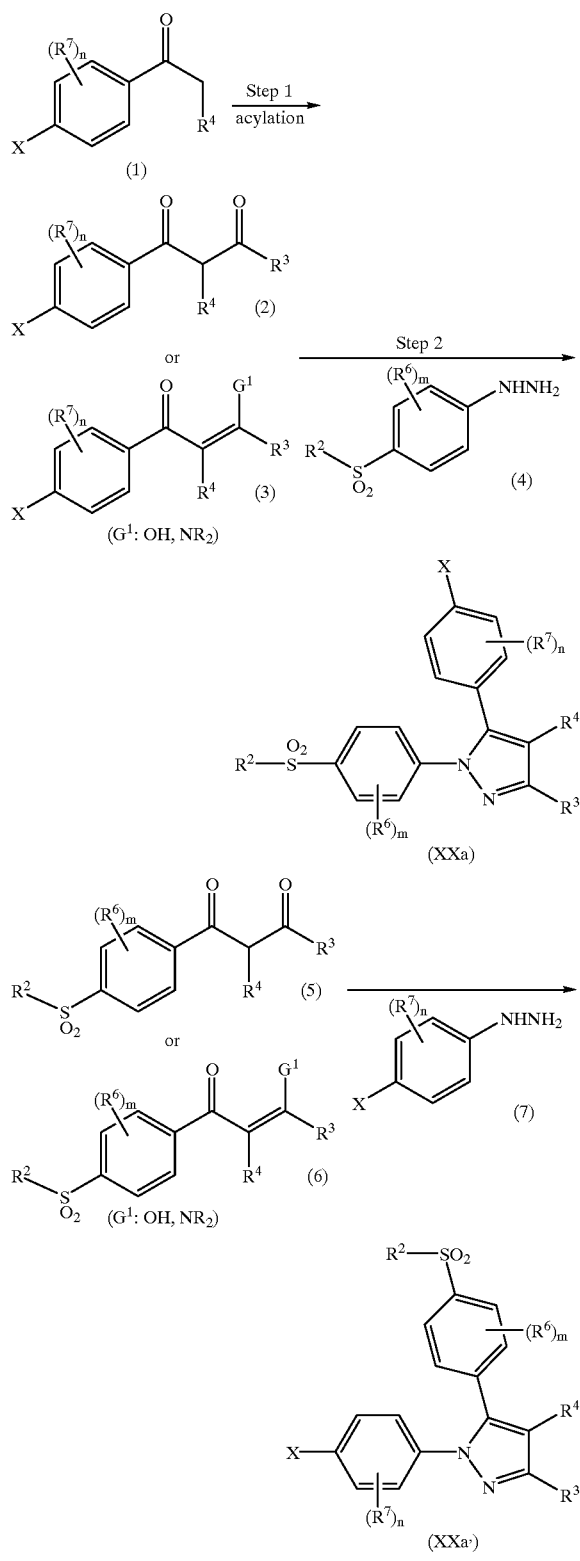

In step 1, ketone (1) is treated with a base (e.g., NaOMe, NaH and Me$_3$Si$_2$NLi preferably NaOMe, wherein Me represents methyl) and an acylating reagent (e.g., ester or ester equivalent such as acylimidazole, dialkylamide and dialkylacetal), in a solvent such as diethylether, tetrahydrofuran, methanol, dichloromethane and methyl tert-butyl ether, to form the 1,3-diketone (2) or 1,3-diketone equivalent (3) ($G^1$ is OH or $NR_2$: R=$C_{1-4}$ alkyl). X in Scheme I is $R^1$, chloro, bromo or OH.

In step 2, the 1,3-diketone (2) or 1,3-diketone equivalent (3) is treated with the salt (such as hydrochloride, hydrobromide, sulfate and oxalate) or the free base of the hydrazine derivative (4) in an anhydrous protic solvent such as ethanol or acetic acid at reflux temperature for from 2 hours to 20 hours to afford the pyrazole compound (XXa).

The starting materials (1) are either commercially available or can be prepared by the method described in *Aust. J. Chem.*, 1977, 30, 229 and *Heterocycles*, 1990, 31, 1951 and which are incorporated by reference. The regio isomeric pyrazole (XXa') can be also prepared from the corresponding 1,3-diketone (5) or 1,3-diketone equivalent (6) and phenyhydrazine (7), which is well known in the art.

Furanone

Furanone (XXb) can be prepared from aryl bromomethyl ketone (8) and aryl acetic acid (9).

SCHEME 10

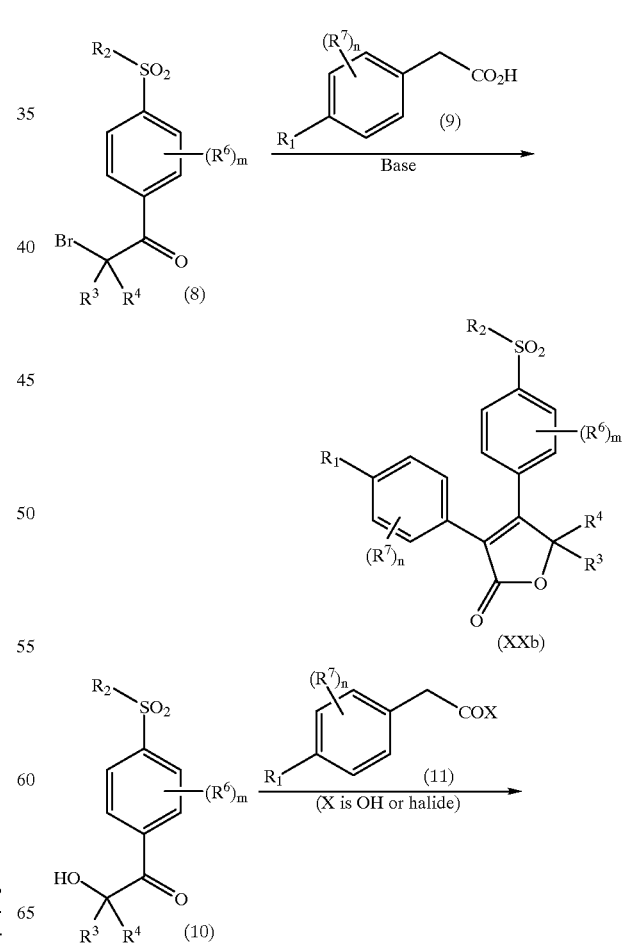

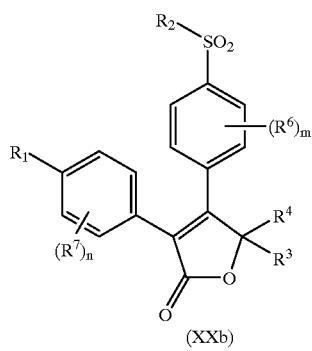

(XXb)

As shown in Scheme 10, an appropriately substituted aryl bromomethyl ketone (8) is reacted with an appropriately substituted arylacetic acid (9) in a solvent such as acetonitrile, dimethylsulfoxide, dimethoxyethane and diethylether in the presence of a base such as triethylamine and diisopropylethylamine and then treated with 1,8-diazabicyclo[5.4.0]undec-7-ene (DBU) to afford the furanone (XXb). The α-bromomethylketone (8) can be easily obtained by halogenation of the corresponding acetophenone, which is well known in the art.

Furanone (XXb) can be also prepared by the reaction of α-hydroxy ketone (10) with (11) (X=OH) in the presence of coupling reagent such as 1-cyclohexyl-3-(2-morpholinoethyl)carbodiimide and metho-p-toluenesulfonate, and further treatment with a base such as DBU.Imidazole:

Imidazole (XXc) can be prepared by the reaction of amidine (14) and α-haloketone (15) followed by the dehydration as shown in Scheme 11.

SCHEME 11

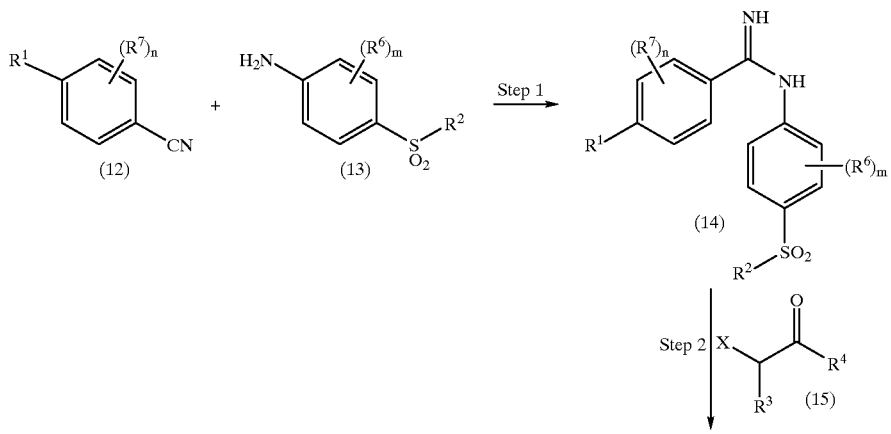

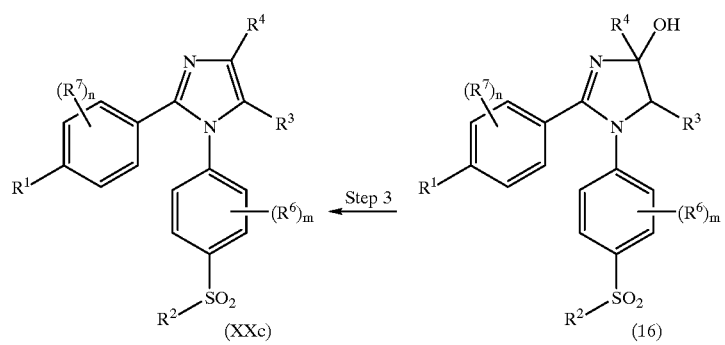

In step 1, the reaction of substituted nitrile (12) with primary phenylamine (13) in the presence of alkylaluminium reagents such as trimethylaluminium, triethylaluminium, diethylaluminium chloride, diethylaluminium chloride in the presence of inert solvents such as toluene, benzene and xylene, gives amidine (14).

In step 2 the reaction of amidine (14) with α-haloketone (15) (where X is bromo or chloro) in the presence of base, such as sodium bicarbonate, potassium carbonate, sodium carbonate and potassium bicarbonate, or hindered tertiary amines such as N,N'-diisopropylethylamine in the presence of inert solvents such as isopropanol, acetone, and dimethylformamide at a temperature of about 0° C. to about 120° C. for 30 min. to 2 days, preferably at a temperature of about 20° C. to about 100° C. for 30 min. to 8 hours, gives the 4,5-dihydrolmidazole (16).

The obtained 4,5-dihydrolmidazole (16) may be dehydrated in the presence of an acid catalyst such as 4-toluenesulfonic acid, trifluoroacetic acid and mineral acids (such as hydrochloric acid) to form the 1,2-disubstituted Imidazole (XXc) of this invention (step 3). A suitable solvent for this dehydration step are e.g., toluene, xylene or benzene. A compound of (XXc) wherein $R^2$ is amino can be prepared by using a compound of (XXc) wherein $R^2$ is methyl, for example by the Huang method (*Tetrahedron Lett.*, 1994, 35, 7201.).

In some cases the intermediate (16) may not be readily isolated. The reaction, under the conditions described above, proceeds to give the Imidazole (XXc) directly.

Pyrrole

Pyrrole can be prepared by the Paal-Knorr's method, which is well known in the art (scheme 12).

SCHEME 12

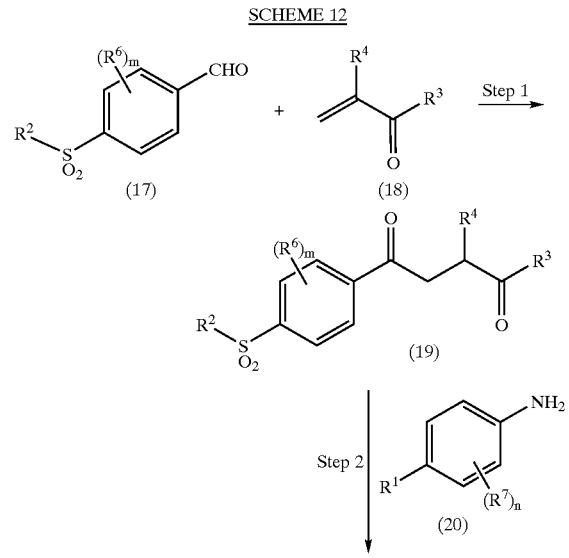

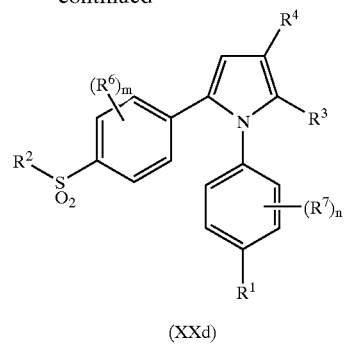

(XXd)

The preparation of suitable 1,4-diketone (19) by the Stetter reaction (for a review on Stetter reaction, *Angew. Chem., Int Ed. Engl.* 1976, 15, 639.) followed by heating with appropriate amines (20) in the Paal-Knorr condensation gives the pyrrole (XXd). The Stetter reaction of substituted benzaldehyde (17) with α,β-unsaturated ketone (18) using the thiazolium salt catalyst in the presence of bases such as triethylamine, diisopropylethylamine and pyridine, gives the 1,4-diketone (19). Suitable solvents for this reaction are methanol, ethanol or isopropanol. The reaction may be carried out at temperatures of about 0° C. to about 120° C. for 15 minutes to 2 days, preferably at temperatures of about 20° C. to about 90° C. for 30 minutes to 1 days. The condensation of 1,4-diketone (19) with arylamine (20) in the presence of an acid catalyst such as 4-toluenesulfonic acid gives the pyrrole (Id). Suitable solvents for this condensation step are e.g., toluene, xylene or benzene. A compound of (XXd) wherein $R^2$ is amino can be prepared by using a compound of (XXd) wherein $R^2$ is methyl, for example by the Huang method (*Tetrahedron Lett.*, 1994, 35, 7201.).

Alternatively, the pyrrole (XXd) can be prepared as shown in Scheme V.

SCHEME 13

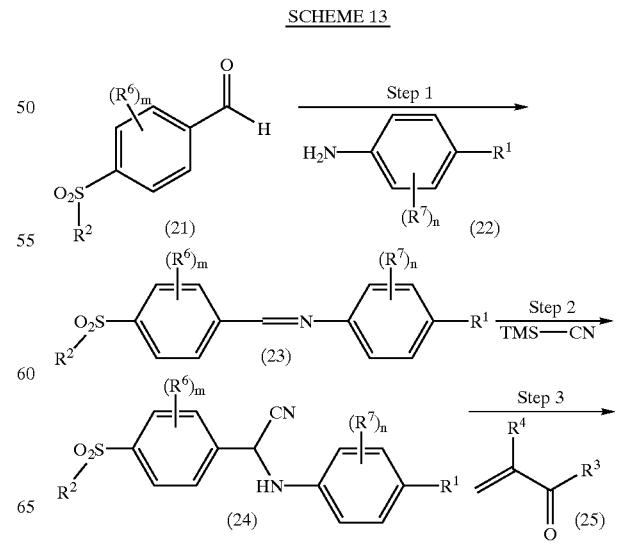

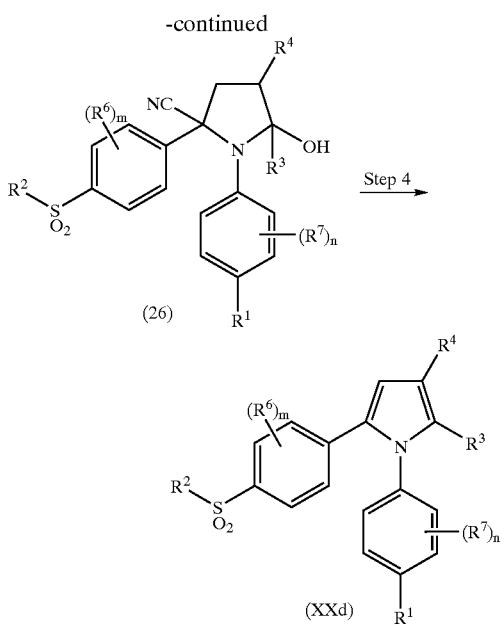

In step 1, an aldimine (23) can be prepared by the dehydration condensation of a benzaldehyde (21) with an aniline (22) in an inert solvent. The reaction is normally and preferably effected in the presence of a solvent. Examples of suitable solvents include aliphatic hydrocarbons such as hexane and heptane; aromatic hydrocarbons such as benzene and toluene; halogenated hydrocarbons such as methylene chloride and chloroform; ether such as diethyl ether, tetrahydrofuran and dioxane; alcohol such as methanol, ethanol and isopropanol. Among these solvents, the alcohol would be preferable. This reaction can be carried out at a temperature of from 5° C. to 200° C., preferably from room temperature to 150° C. for from 10 minutes to 20 hours, more preferably from 1 hour to 15 hours.

In step 2, an anilinonitrile (24) can be prepared by an addition of hydrogen cyanide to the aldimine (23), prepared as described in step 1. The reaction may be carried out by reacting the aldimine (23) with trimethylsilyl cyanide (TMS-CN) in the presence of a Lewis acid, for example, aluminium chloride, tin chloride and zinc chloride in an inert solvent such as diethyl ether, tetrahydrofuran, dioxane, benzene, and methylene chloride, preferably diethyl ether and tetrahydrofuran. This reaction can be carried out at a temperature of from 5° C. to 200° C., preferably from room temperature to 150° C. for from 10 minutes to 50 hours, more preferably from 1 hour to 20 hours.

In step 3 and 4, the pyrrole (XXd) can be prepared by reacting the anilinonitrile (24), prepared as described in step 2, with an α,β-unsaturated aldehyde or ketone (25) to obtain a pyrrolidine compound (26), which can be then dehydrated and dehydrogencyanated.

In step 3, the reaction may be carried out by reacting the anilinonitrile (24) with an α,β-unsaturated aldehyde or ketone (25) in the presence of a base, such as lithium amide, sodium amide, potassium amide, lithium bis(trimethylsilyl) amide, and sodium methoxide, preferably lithium bis(trimethylsilyl)amide in an inert solvent such as diethyl ether, tetrahydrofuran, dioxane, benzene, and methylene chloride, preferably diethyl ether and tetrahydrofuran. This reaction can be carried out at a temperature of from −78° C. to 100° C., preferably from −78° C. to room temperature for from 10 minutes to 30 hours, preferably from 1 hour to 15 hours.

In step 4, the pyrroles (XXd) can be prepared by the dehydration and dehydrogencyanation of the pyrrolidine compound (26). This may be achieved by heating the crude product obtained by evaporation of the solvent from the product of step 3, or by heating the crude material obtained by the extraction, at a temperature of from 80° C. to 250° C., in the presence or absence of a solvent after completion of the reaction of step 3. Suitable solvent would be toluene, xylene, diglyme, diphenyl ether, dimethylformamide or the like.

Oxazole

Oxazole (XXe) can be prepared according to the following procedures of Scheme 14.

SCHEME 14

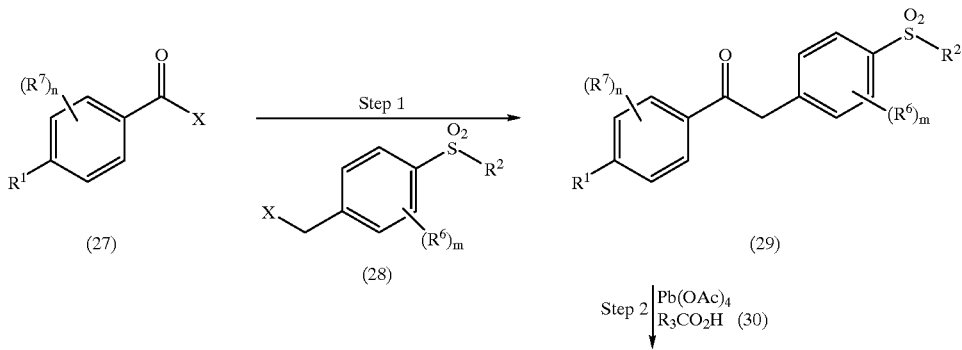

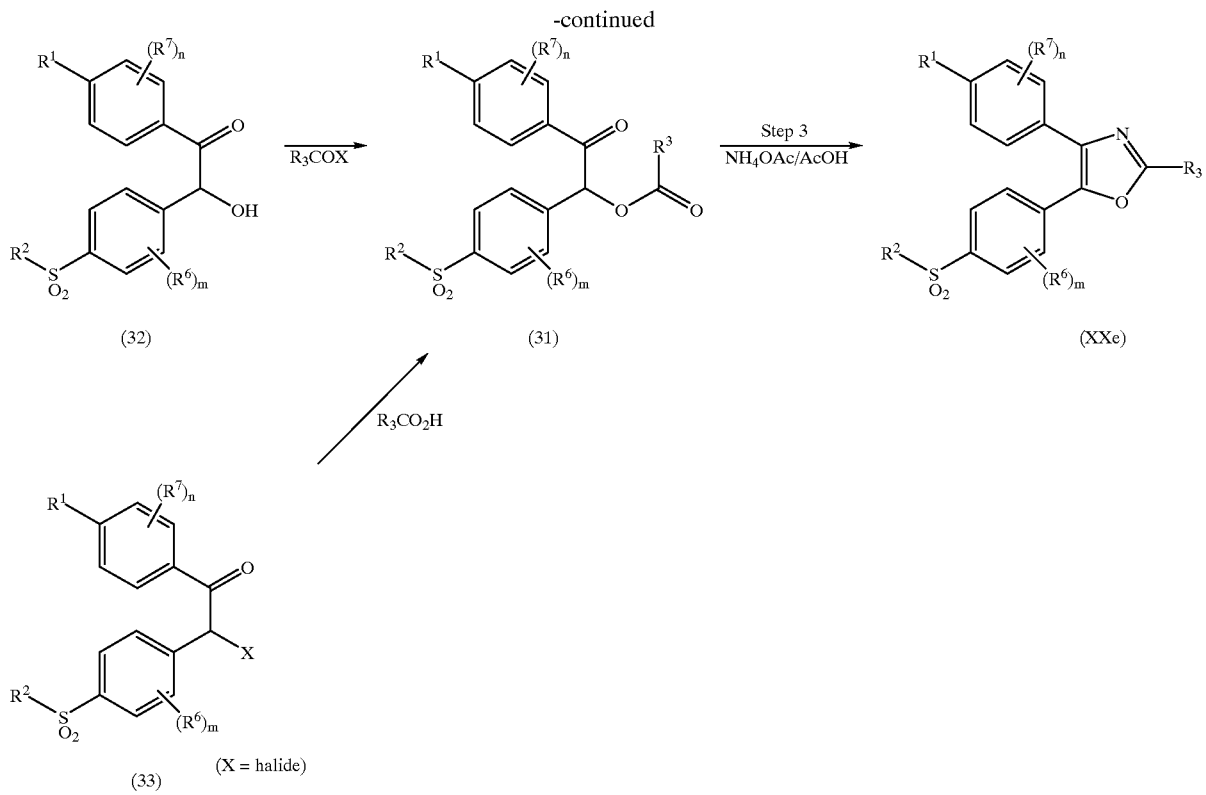

In step 1, the ketone (29) can be prepared by the reaction of acid halide (27) with 4-sulfonylbenzyl halide (preferably X=Cl or Br) (28) in the presence of metal such as zinc and magnesium, preferably zinc, in an inert solvent such as 1,2-dimethoxyethane, dioxane, diethyl ether, tetrahydrofuran, methylene chloride, benzene, and toluene at a temperature of from 0° C. to 150° C., preferably from room temperature to 50° C. for from 10 minutes to 30 hours, preferably from 1 hour to 15 hours. Suitable catalyst e.g., tetrakis(triphenylphosphine)palladium can be used in this reaction. In step 2, the α-carbonyloxy ketone (31) can be prepared by the reaction of ketone (29), prepared as described above, with an appropriate carboxylic acid (30) in the presence of lead (IV) acetate and manganese (III) acetate in the presence or absence of a solvent, but when a solvent is used, suitable solvent would be benzene, toluene and xylene. This reaction can be carried out at a temperature of from room temperature to 150° C., preferably from 50° C. to 120° C. for from 10 minutes to 30 hours, more preferably from 1 hour to 15 hours.

The oxazole (XXe) can be prepared by heating the α-carbonyloxy ketone (31) in a lower alkylcarboxylic acid such as acetic acid, formic acid and propionic acid in the presence of ammonium acetate, ammonium formate and ammonium carbonate, preferably ammonium acetate.

Alternatively, the α-carbonyloxy ketone (31) can be prepared from the corresponding α-hydroxy ketone (32) or α-halo ketone (33) by reacting with an appropriate acid halide or carboxylic acid in the presence of a base such as pyridine and triethylamine in an inert solvent such as methylene chloride and chloroform at a temperature of −10° C. to 100° C. The corresponding α-hydroxy ketone (32) or α-halo ketone (33) can be prepared by oxidation of the ketone (29) by using iodobenzene diacetate, or by halogenation of the ketone by using bromine, chlorine, and N-bromosuccineimide in the presence of an inert solvent such as 1,2-dimethoxyethane, dioxane, diethyl ether, tetrahydrofuran, benzene and toluene. A compound of (XXe) wherein $R^2$ is amino can be prepared by using a compoud of (XXe) wherein $R^2$ is methyl, for example by the Huang method (*Tetrahedron Lett.,* 1994, 35, 7201.).

The regioisomeric oxazole can be prepared from the corresponding sulfonylbenzoic acid halide and benzyl halide.

Thiophene

Thiophene analogs can be prepared as shown in scheme 15.

SCHEME 15

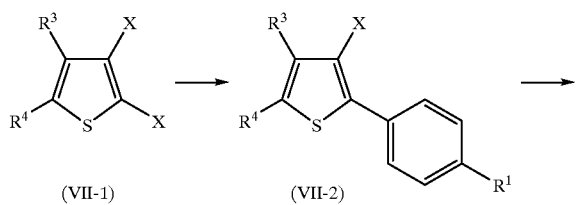

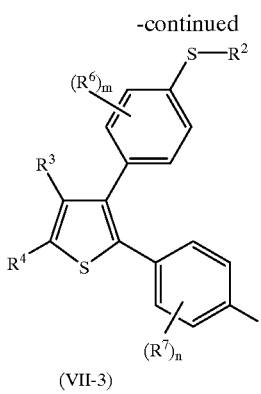

(VII-3)

The Suzuki coupling of 2,3-dihalothiophene (VII-1) with 4-(aryl or heteroaryl)phenylboronic acid, followed by the second coupling with 4-($R^2$-thio)phenylboronic acid pro- vides 2-[4-(aryl or heteroaryl)phenyl]-3-[4-(methylthio)phenyl]thiophene. The obtained thiophene (VII-3) may be oxidized by the methods known in the art to give the methylsulfonyl analogs (VII-4).

Alternatively, the other arylmetal reagents such as aryl Grignard reagent, arylzinc reagent, aryltin reagent, or arylsilyl reagent instead of arylboronic acid can be used in this reaction.

The reaction of arylboronic acid with 2,3-dihalothiophene may be carried out in a solvent such as benzene, toluene, dimethoxyethane, dimethylformamide, preferably dimethoxyethane, typically in the presence of a base such as pottasium hydroxide, thallium hydroxide, triethylamine, sodium bicarbonate, or a combination of water and alone solvent preferably water and dimethoxyethane. The catalyst may be selected from those typically employed for the so-called Suzuki reaction (for example, tetrakis (triphenylphosphine)palladium and dichloro bis (triphenylphosphine)palladium). The reaction is carried out at a temperature in the range from 20 to 160° C., usually 60 to 130° C. for 10 minutes to 5 days, usually 30 minutes to 15 hours.

Isoxazoles

When A is an isoxazole ring, the isoxazole derivatives (XXf), (XXg), and (XXg') can be prepared from appropriate oximes (40) and (47) as shown in schemes 16 and 17.

3,4-Diphenylisoxazoles

Synthesis of 3,4-diphenylisoxazole is Shown in Scheme 16.

SCHEME 16

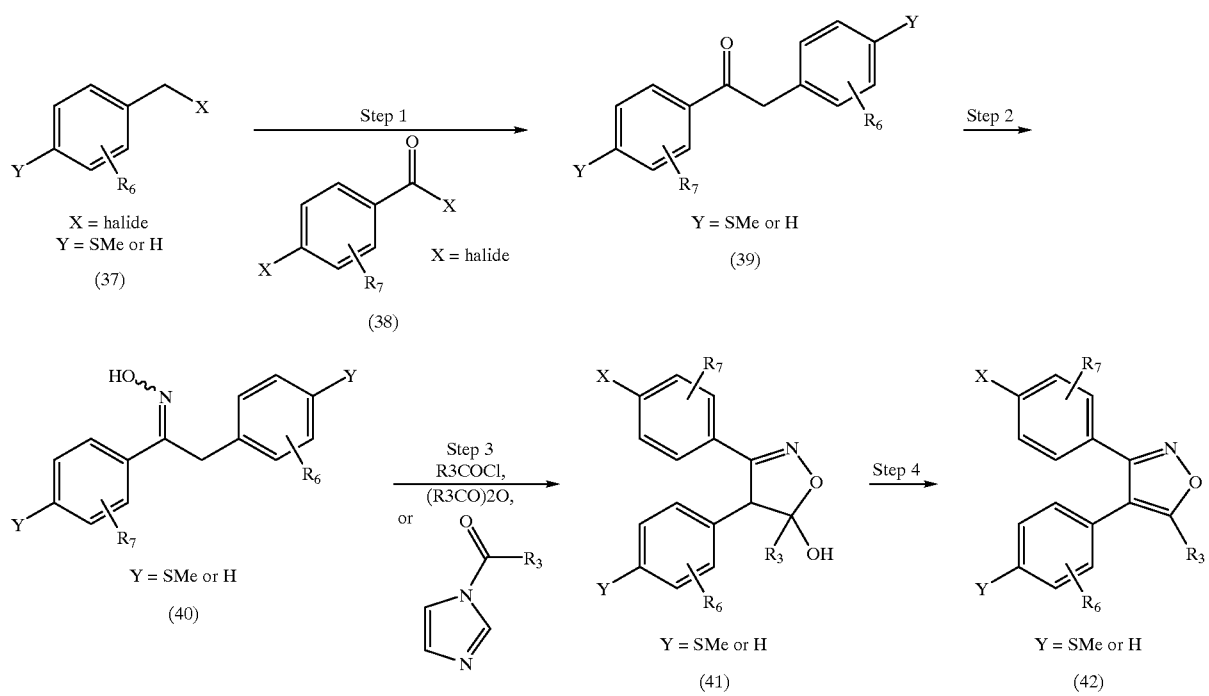

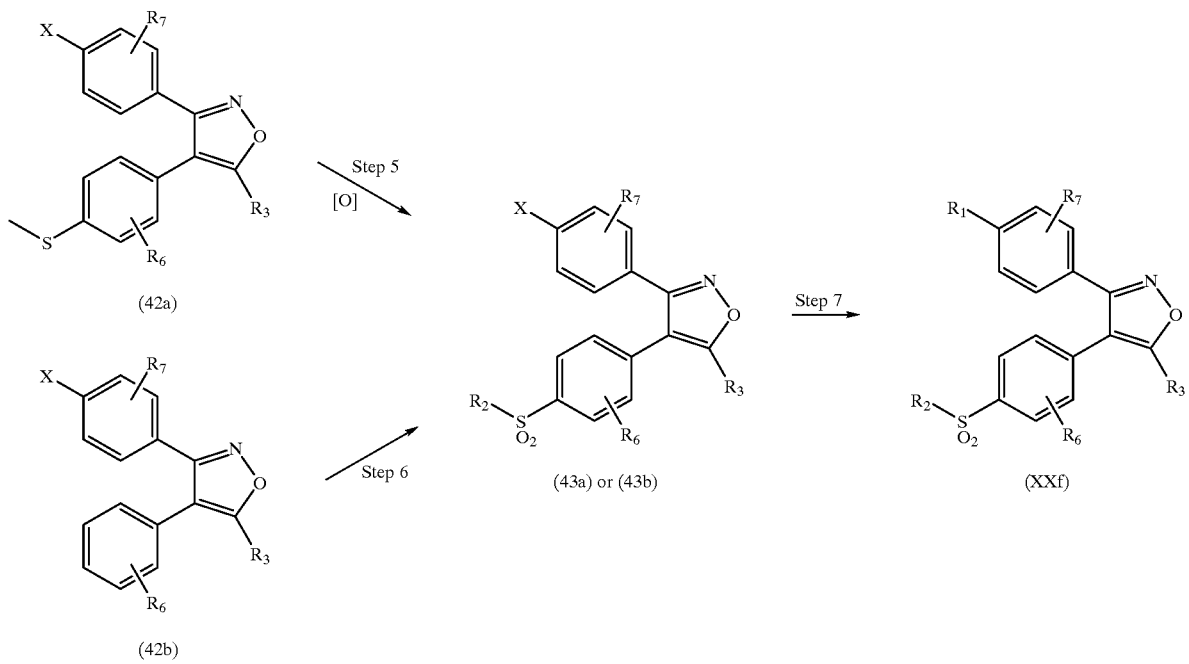

In step 1, the ketone (39) can be prepared from the benzyl halide (37) and the acid halide (38), according to the procedure described in step 1 in oxazole synthesis (Scheme 14).

In step 2, the oxime (40) can be obtained by treatment of the ketone (39) with hydroxylamine hydrochloride in the presence of base such as sodium acetate, in an inert solvent such as water, methanol, ethanol, i-propanol, tetrahydrofuran, 1,4-dioxane, diethyl ether, or a miture of the above described solvents, preferably a mixture of water and ethanol. This reaction can be carried out at a temperature of from 0° C. to reflux temperature, preferably from 50° C. to reflux temperature for from 15 minutes to 24 hours, preferably from 1 hour to 15 hours.

In step 3, the 4,5-dihydroisoxazole (41) can be prepared via C-acylation of the oxime (40), followed by spontaneous cyclization. This reaction may be carried out by reacting the oxime (40) with an acyl halide, acid anhydride, N-acylimidazole, and carboxamide, in the presence of base such as lithium amide, sodium amide, potassium amide, lithium diisopropylamide, lithium bis(trimethylsilyl)amide, sodium bis(trimethylsilyl)amide, and potassium bis(trimethylsilyl)amide, preferably lithium diisopropylamide, in an inert solvent such as tetrahydrofuran, diethyl ether, 1,2-dimethoxyethane, dioxane, benzene, and methylene chloride, preferably diethyl ether and tetrahydrofuran, at a temperature of from −78° C. to 100° C., preferably −78° C. to room temperature for from 10 minutes to 30 hours, preferably from 30 minutes to 15 hours.

In step 4, the isoxazole (42) can be obtained by dehydration of the dihydroisoxazole (41) using acid. This may be achieved by heating the dihydroisoxazole (41) with acid, such as hydrochloric acid, hydrobromic acid, sulfuric acid, methanesulfonic aicd, p-toluenesulfonic acid, and polyphosphoric acid, in an inert solvent such as methanol, ethanol, 2-propanol, tetrahydrofuran, diethyl ether, 1,4-dioxane, benznen, toluene, xylene, diglyme, dimethylforamide, dimethylsulfoxide or the like, at a temperature of from 40° C. to reflux temperature, preferably 50° C. to 100° C., for from 10 minutes to 30 hours, preferably 30 minutes to 15 hours.

In step 5, the sulfone (43a) can be prepared by oxidation of the sulfide (42a). This reaction may be carried out with an oxidant such as mCPBA, peracetic acid, hydrogen peroxide, and oxone®, in an inert solvent such as chloroform, tetrachlorocarbon, dichloromethane, acetic acid, preferably dichloromethane, at a temperature of from −20° C. to reflux temperature, preferably 0° C. to 50° C., for from 15 minutes to 30 hours, preferably 30 minutes to 15 hours.

In step 6, the sulfonamide (43b) can be prepared by after reacting the isoxazole (42b) with chlorosulfonic acid at a temperature of from −78° C. to 100° C., preferably −78° C. to 70° C., for from 15 minutes to 30 hours, preferably 30 minutes to 15 hours, pouring the reaction mixture into a mixture of ice and concentrated ammonia.

In step 7, the isoxazole (XXf) can be obtained via the cross coupling reaction of the isoxazole (43), as described hereinafter.

The regioisomeric isoxazole can be prepared from the corresponding 4-methylthiobenzoyl halide and 4-bromobenzyl halide.

4,5-Diphenylisoxazoles
Synthesis of 4,5-diphenylisoxazole is shown in scheme 17.
SCHEME 17
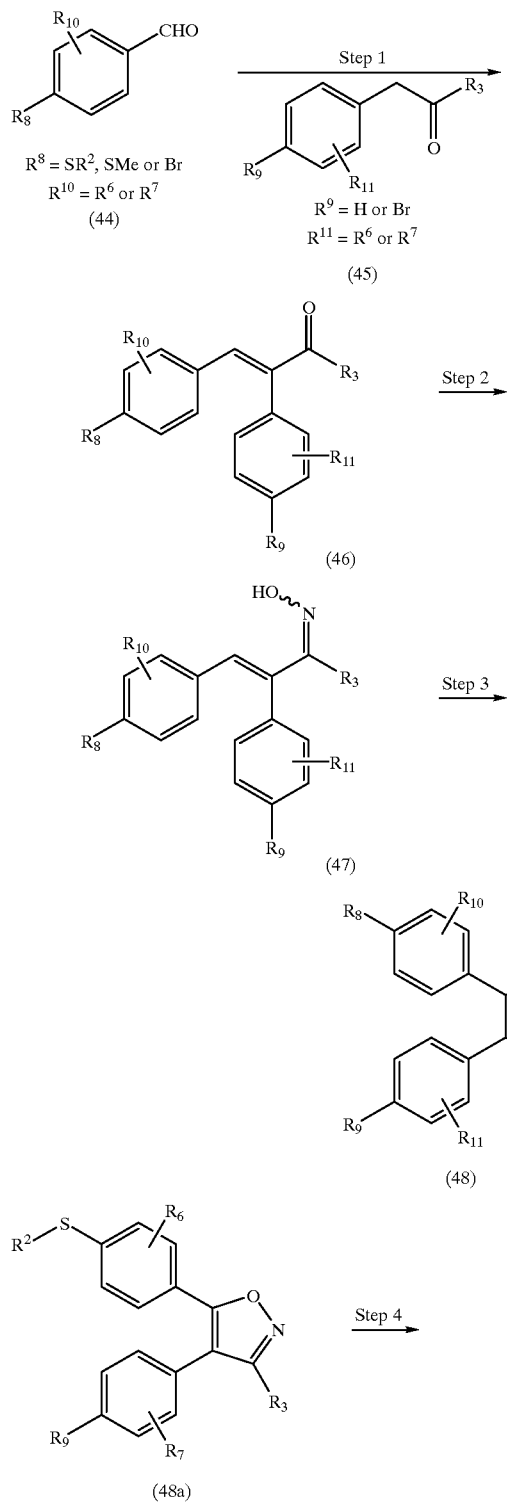
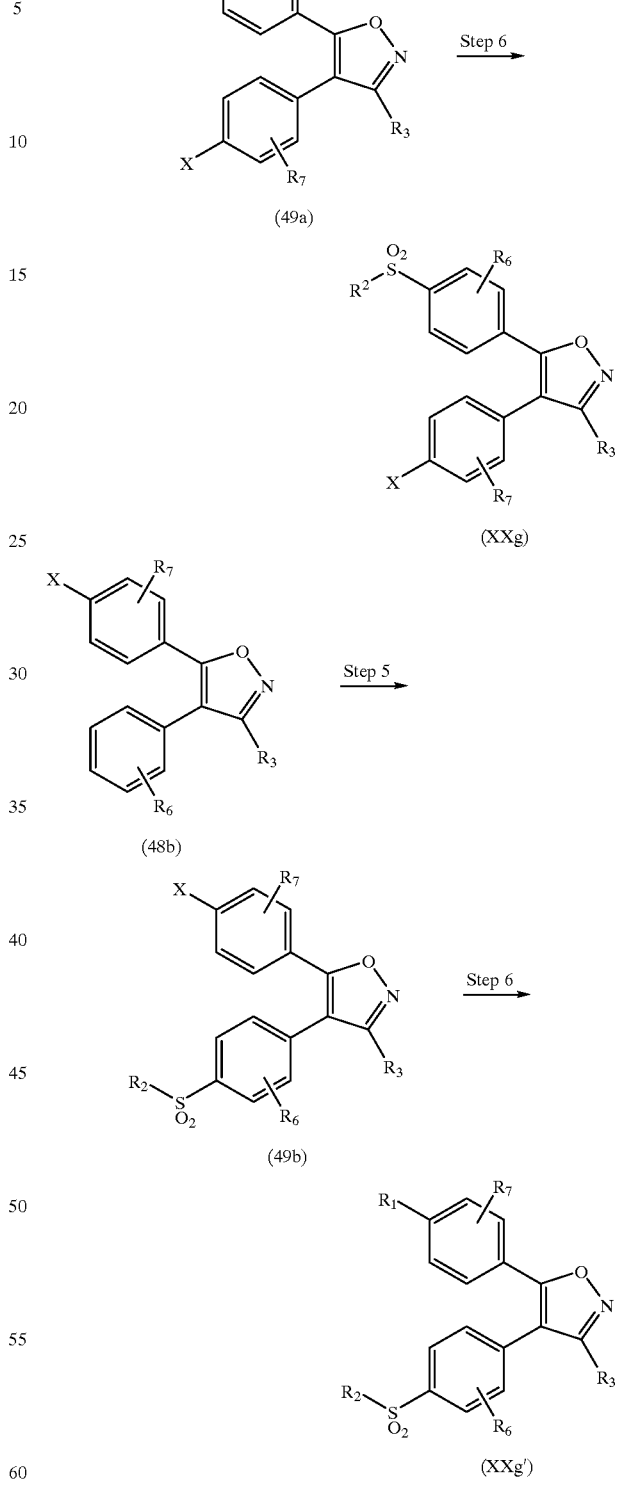
In step 1, the α,β-unsaturated ketone (46) can be prepared by aldol reaction of the benzaldehyde (44) with the ketone (45), followed by β-elimination, in the presence of base, such as potassium carbonate, sodium carbonate, sodium hydride, potassium hydride, lithium amide, sodium amide, potassium amide, litium diisoprppylamide, lithium bis(trimethylsilyl)amide, potassium bis(trimethylsilyl)amide, sodium bis(trimethylsilyl)amide, piperidine, and 1,8-diazabicyclo[5.4.0]undec-7-ene (DBU), preferably piperidine, in an inert solvent such as diethyl ether, tetrahydrofuran, 1,2-dimethoxyethane, 1,4-dioxane, benzene, toluene, xylene, and dimethyl sulfoxide, preferably benzene and toulene. This reaction may be carried out at a temperature of from −78° C. to reflux temperature, preferably room temperature to reflux temperature, for from 15 minutes to 50 hours, preferably 1 hour to 30 hours.

In step 2, the oxime (47) can be obtained from the ketone (46) according to the procedure described in step 2 in 3,4-diphenylisoxazole section.

In step 3, the isoxazole (48) can be prepared by treating the oxime (47) with a mixture of iodine and potassium iodide in the presence of base such as triethylamine, N,N-diisopropylethylamine, DBU, potassium carbonate, sodium carbonate, sodium hydrogen carbonate, potassium hydrogen carbonate, and their aqueous solution, in an appropriate solvent such as diethyl ether, tetrahydrofuran, 1,4-dioxane, 1,2-dimethoxyethane, benzene, toluene, xylene, dimethyl sulfoxide, and N,N-dimethylforamide, preferably tetrahydrofuran. This reaction may be carried out at a temperature of from 0° C. to reflux, preferably room temperature to reflux temperature, for from 15 minutes to 30 hours, preferably 30 minutes to 15 hours.

In step 4, the sulfone (49a) can be obtained from the sulfide (48a), according to the procedure described in step 5 in 3,4-diphenylisoxazole section.

In step 5, the sulfonamide (49b) can be obtained from the isoxazole (48b), according to the procedure described in step 6 in 3,4-diphenylisoxazole section.

In step 6, the isoxazoles (XXg) and (XXg') can be respectively obtained from the isoxazoles (49a) abd (49b) through the cross coupling reaction described hereinafter.

Thiazole

SCHEME 18

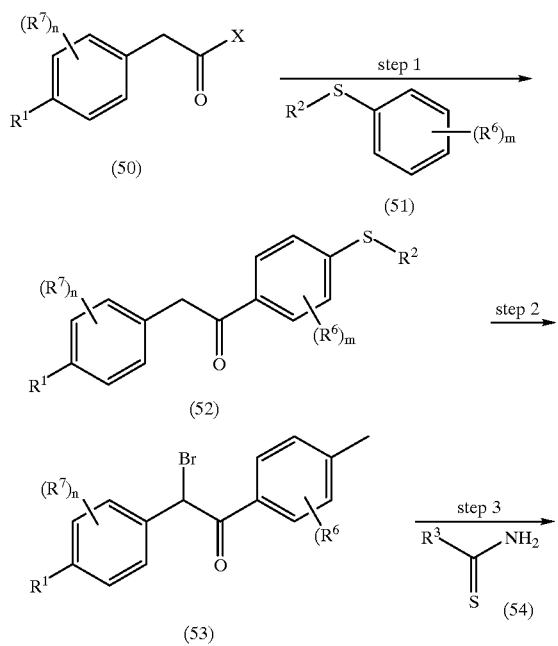

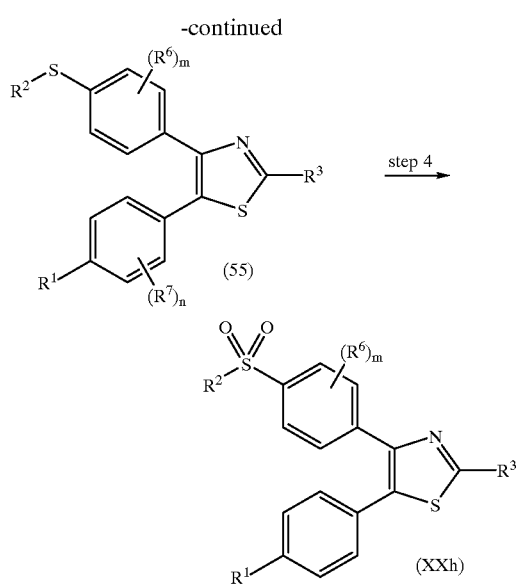

Thiazole can be prepared according to the following procedures of Scheme X. In step 18, the ketone (52) can be prepared by the Friedel Crafts acylation. Acid halide (50) (prferably X=Cl or Br) is treated with and reacted with $R^2$-thiobenzene (51) and lewis acid such as aluminum chloride, titanium(IV) chloride, and tin(IV) chloride in an inert solvent such as methylene chloride, chloroform, nitrobenzene, dichlorobenzene, chlorobenzene and carbon disulfide, at a temperature of from 0° C. to reflux temperature, preferably from room temperature to 50° C. for from 10 minutes to 30 hours, preferebly from 1 hour to 20 hours. In step 2, the α-bromoketone (53) can be prepared by the reaction of ketone (52) with bromine in an inert solvent such as acetic acid, methylene chloride, chloroform, carbontetrachloride, dioxane, diethyl ether. This reaction can be carried out at a temperature of from room temperature to 150° C., preferably from 0° C. to 100° C. for from 10 minutes to 30 hours, preferably from 1 hour to 5 hours. In step 3, the thiazole ring can be prepared by the reaction of α-bromoketone (53) with the thioamide (54) in an inert solvent such as ethanol, methanol, dioxane, toluene, at a temperature of from 0° C. to reflux temperature, preferably from 50° C. to reflux temperature, for from 10 minutes to 30 hours, preferebly 1 hour to 20 hours. In step 4, Sulfonyl-benzene (XXh) can be prepared by the oxidation of sulfide compound (55). This reaction may be carried out with an oxidizing agent such as mCPBA, peracetic acid, hydrogen peroxide and oxone®, preferably mCPBA, in an inert solvent such as tetrachlorocarbon, dichloromethane, chloroform, and acetic acid at a temperature of from −20° C. to reflux temperature, preferably 0° C. to 50° C., for from 10 minutes to 30 hours, preferebly from 1 hour to 20 hours.

The compounds of formula (XX) wherein A is other than the above-mentioned heterocyclic or carbocyclic, can be prepared according to the known methods.

2) Synthesis of Compound (XX) by Cross Coupling Reaction

The compounds of formula (XX) can be synthesized by using the method of Kharash, Negishi, Stille, or Suzuki et. al., which are well known in the art. In general, biaryl compounds are synthesized by a number of catalytic cross-coupling reactions from arylhalides or triflates and arylmetal reagents, [for example, Grignard reagent (the so-called Kharasch reaction), arylzinc reagent (the so-called Negishi reaction), aryltin reagent (the so-called stille reaction), arylboron reagent (the so-called Suzuki reaction), arylsilyl reagent, etc. (review article showed be cited here ; S. P. Stanforth, *Tetrahedron*, 1998, 54 , 263–303]. These methods can be applicable to the preparation of compound (XX). The compound (XX) can be prepared from corresponding aryl halides or triflates (XXI) and aryl metal reagent (34), as shown in scheme 19.

SCHEME XI

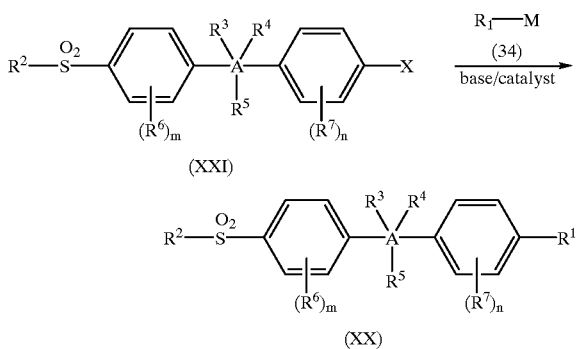

(wherein X is halide or triflate, and M is boronic acid, boronic ester, zinc halide, magnesium halide, or trialkyl tin groups)

The reaction of aryl or heteroarylboronic acid (34) with an arylhalide or triflate (XXI) may be carried out in a solvent such as benzene, toluene, dimethoxyethane, dimethylformamide, preferably dimethoxyethane, typically in the presence of a base such as pottasium hydroxide, thallium hydroxide, triethylamine, sodium bicarbonate, or a combination of water and alone solvent preferably water and dimethoxyethane. The catalyst may be selected from those typically employed for the so-called Suzuki reaction (for example, tetrakis(triphenylphosphine)palladium and dichloro bis(triphenylphosphine)palladium). The reaction is carried out at a temperature in the range from 20 to 160° C., usually 60 to 130° C. for 10 minutes to 5 days, usually 30 minutes to 15 hours.

The reaction of aryl or heteroarylzinchalide (34) with an arylhalide or triflate (II) may be carried out in a solvent such as tetrahydrofuran, diethylether and dimethoxyethane, preferably tetrahydrofuran. The catalyst may be selected from those typically employed for the so-called Negishi reaction (for example, tetrakis(triphenylphosphine)palladium, tetrakis(triphenylphosphine)nickel, dichlorobis (triphenylphosphine)palladium, dichlorobis (triphenylphosphine)palladium, /n-BuLi, dichlorobis(1,1-bis(diphenylphosphino)ferrocene)palladium and dichlorobis (1,4-bis(diphenylphosphino)butane)palladium,). The reaction is carried out at a temperature in the range from 20 to 160° C., usually 20 to 130 ° C for 10 minutes to 5 days, usually 30 minutes to 15 hours.

The reaction of aryl or heteroaryltin reagent (34) with an arylhalide or triflate (II) may be carried out in a solvent such as dimethylformamide, tetrahydrofuran, 1,4-dioxane, benzene, toluene and dimethoxyethane, preferably tetrahydrofuran and 1,4-dioxane, if necessary, a salt such as lithium chloride, ammonium hydroxide, copper(I) bromide, is used. The catalyst may be selected from those typically employed for the so-called Stille reaction (for example, tetrakis (triphenylphosphine)palladium and dichlorobis (triphenylphosphine)palladium). The reaction is carried out at a temperature in the range from 20 to 160° C., usually 20 to 130° C. for 10 minutes to 5 days, usually 30 minutes to 15 hours.

The reaction of aryl or hetero aryl Grignard reagent (34) with an arylhalide or triflate (XXI) may be carried out in a solvent such as tetrahydrofuran, 1,4-dioxane, benzene, toluene and dimethoxyethane, preferably tetrahydrofuran, 1,4-dioxane. The catalyst may be selected from those typically employed for the so-called Kharasch reaction (for example, dichlorobis(triphenylphosphine)nickel, dichlorobis(1,4-bis (diphenylphosphino)butane)nickel and dichlorobis(1,2-bis (diphenylphosphino)ethane)nickel,). The reaction is carried out at a temperature in the range from 20 to 160° C., usually 20 to 130° C. for 10 minutes to 5 days, usually 30 minutes to 15 hours.

As apparent to one skilled in the art, the compound (I) can be obtained from a reaction of the compound (XXII) or (XXIII), and the compound (36) as shown in scheme 20,

SCHEME XII

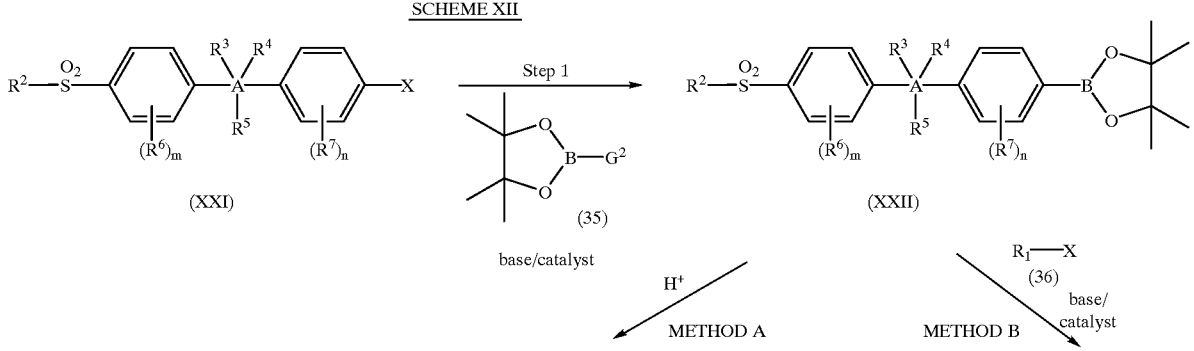

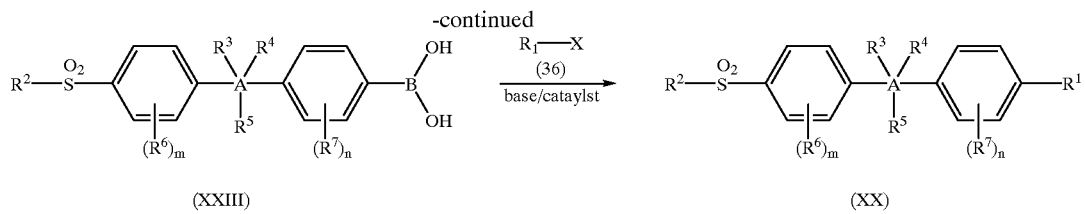

(XXIII) → (XX)

In step 1, the reaction of aryl halide (XXI) and boron reagent (35) ($G^2$ is H or $B(C_{1-4}$ alkyl$)_2$) in an appropriate solvent such as dimethoxyethane and tetrahydrofuran in the presence of a catalyst such as tetrakis(triphenylphosphine) palladium, dichlorobis(triphenylphosphine)palladium and a base such as potassium acetate, triethylamine, at heating condition (ex., 80° C. to 100° C.) for 2 hours to 20 hours, gives boronic acid ester product (III).

The boronic acid ester (XXII) can be hydrolyzed by an acid catalyst such as 4-toluenesulfonic acid, trifluoroacetic acid, or mineral acids (such as hydrochloric acid) in a solvent such as tetrahydrofuranetoluene, diethylether, benzene, or a combination of water and alone solvent to form the boronic acid (XXIII).

The biaryl compound (XX) can be prepared from boronic acid ester (XXII) or boronic acid (XXIII) and arylhalides or triflates (36) in the presence of a catalyst such as tetrakis(triphenylphosphine)palladium, dichlorobis(triphenylphosphine)palladium and a base such as pottasium phosphate, triethylamine, sodium bicarbonate and sodium carbonate, at heating condition (ex., 60° C. to 150° C.) for 2 hours to 20 hours. Suitable solvents for this coupling reaction are for example benzene, toluene, dimethoxyethane, dimethylformamide, tetrahydrofuran, 1,4-dioxane, or a combination of water and alone solvent, preferably water and dimethoxyethane. The starting material (XXI), wherein X is halide or triflate can be prepared according to the methods as described in general synthesis 1), as apparent to one skilled in the art.

The starting materials in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

A compound of formula (XXX) may be prepared by any synthetic procedure applicable to structure-related compounds known to those skilled in the art. The following representative examples as described in Schemes A–F are illustrative of the invention in which, unless otherwise stated, Ar, $R^1$, $R^2$, $R^3$,$X^1$,$X^2$, m and n are as defined herein before. For the synthesis of compounds of related-structure to compounds of the present invention, see "Benzimidazoles and Congeneric Tricyclic Compounds" in *Heterocyclic Compounds*, Vol. 40, Preson, P. N. Ed., John Wiley & Sons, NY, 1981.

SCHEME A

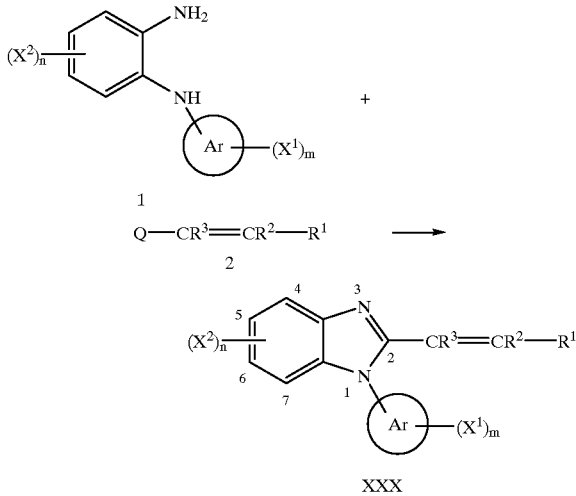

For example, the compound of formula XXX may be prepared according to the reaction outlined in Scheme A. In the instant example, a phenylenediamine compound of formula 1 is reacted with a compound of formula 2 wherein the group Q is defined such that the compound of formula 2 is, but not limited to, a carboxylic acid, a carboxylic acid ester, a carboxamide, a carboxylic acid anhydride, a carboxylic acid chloride, an orthoester, an imino ether or a carboxaldehyde. The reaction may be conducted in the presence or absence of a reaction inert solvent. Preferred reaction inert solvents include, but are not limited to, benzene, toluene, xylene, pyridine, 1,2-dichloroethane, o-dichlorobenzene, nitrobenzene, dichloromethane and the like. Preferably, the reaction is conducted in the presence of a promoter such as hydrochloric acid, polyphosphoric acid, phosphorous pentoxide, phosphorous oxychloride, polyphosphoric acid ethyl ether, polyphosphoric acid trimethylsilyl ether, p-toluenesulfonic acid, zinc (II) chloride and the like. When a compound of formula 2 is carboxaldehyde, the reaction may be conducted in the presence of an oxidant such as cupric acetate, chloranil, and the like. Reaction temperatures are preferably in the range of $-40\infty$ C. to $250\infty$ C., more preferably $10\infty$ C. to $200\infty$ C., usually in the range of room temperature (e.g., $25\infty$ C.) to $200\infty$ C., but if necessary, lower or higher temperature can be employed. Reaction times are, in general, from 1 minute to several days, preferably from 20 minutes to 1 day. Alternatively, the reaction may be conducted in a sealed tube or an autoclave at medium to high pressure to accelerate it, preferably in the range of 2 to 150 kg/cm$^2$.

SCHEME B

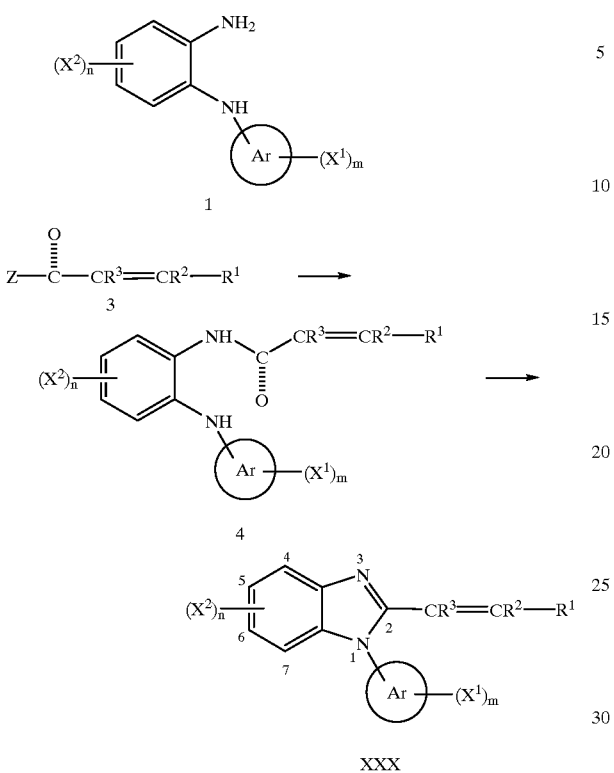

Alternatively, the compounds of formula XXX may be prepared by a two step procedure from phenylenediamine compounds of formula 1 via the (N-acylamino)phenylamine compounds of formula 4 as shown in Scheme B. In the first step, a phenylenediamine compound of formula 1 is reacted with a compound of formula 3, wherein Z is selected from halo, —OH, —OR(R is $C_1$–$C_4$ alkyl), —$NH_2$ or —OC(O)$CR^2$=$CR^3$—$R^1$, by conventional methods known to those skilled in the art to form amides of formula 4. For example, when a compound of formula 3 is carboxylic acid (i.e., Z is OH), the reaction is preferably conducted in the presence of a coupling reagent such as 1-(dimethylaminopropyl)-3-ethylcarbodiimide (WSC), N,N'-dicyclohexylcarbodiimide (DCC), carbonyldiimidazole, cyanophosphonic acid diethyl ester or the like. Preferred reaction-inert solvents include, but are not limited to, acetone, acetonitrile, dichloromethane, N,N-dimethylformamide, N,N-dimethylacetamide, dimethylsulfoxide, dioxane, tetrahydrofuran and pyridine. Reaction temperatures are preferably in the range of −40∞ C. to 250∞ C., more preferably 10∞ C. to 200∞ C., usually in the range of room temperature (e.g., 25∞ C.) to 200∞ C., but if necessary, lower or higher temperature can be employed.

In the next step, the compounds of formula XXX are provided by cyclization of the compounds of formula 4. The reaction may be conducted in the presence or absence of a reaction inert solvent. Preferred reaction inert solvents include, but are not limited to, benzene, toluene, xylene, pyridine, 1,2-dichloroethane, o-dichlorobenzene, nitrobenzene, dichloromethane and ethanol. Preferably, the reaction is conducted in the presence of a promoter such as of hydrochloric acid, polyphosphoric acid, phosphorous pentoxide, phosphorous oxychloride, polyphosphoric acid ethyl ether, polyphosphoric acid trimethylsilyl ether, thionyl chloride and p-toluenesulfonic acid. Alternatively, the cyclization reaction may be performed under Mitsunobu-type reaction conditions, for example, in the presence of triphenylphosphine and diethyl azodicarboxylate (DEAD). Reaction temperatures are preferably in the range of −40∞ C. to 250∞ C., more preferably 10∞ C. to 200∞ C., usually in the range of room temperature (e.g., 25∞ C.) to 200∞ C., but if necessary, lower or higher temperature can be employed. Reaction times are, in general, from 1 minute to several days, preferably from 20 minutes to 1 day.

SCHEME C

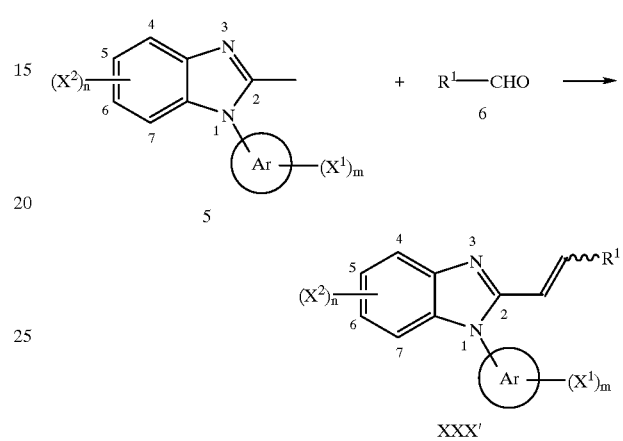

In another embodiment, the compounds of formula XXX' may be prepared as shown in Scheme C. Thus, 2-methylbenzimidazole compounds of formula 5 are reacted with aldehydes of formula 6 in the presence or absence of base (Sanfilippo, P. J.; Urbanski, M.; Press, J. B.; Hajos, Z. G.; Shriver, D. A.; Scott, C. K. *J. Med. Chem.*, 1988, 31, 1778). When the said reaction is conducted in the absence of base, the reaction is preferably performed in a sealed tube or an autoclave at medium to high pressure, preferably in the range of 2 to 150 kg/cm$^2$. The reaction may be conducted in the presence or absence of a reaction inert solvent. Preferred reaction inert solvents include, but are not limited to, benzene, toluene, xylene, chlorobenzene, nitrobenzene, acetic acid, acetic anhydride. Reaction temperatures are generally in the range of −100° C. to 250° C., preferably in the range of room temperature (e.g., 25° C.) to 200° C., but if necessary, lower or higher temperature can be employed. Reaction times are, in general, from 1 minute to a day, preferably from 20 minutes to 5 hours, however shorter or longer reaction times if necessary can be employed. When the said reaction is conducted in the presence of base, reaction temperatures are generally in the range of −100° C. to 250° C., preferably in the range of −80° C. to room temperature(e.g., 25° C.), but if necessary, lower or higher temperature can be employed. Preferred reaction inert solvents include, but are not limited to, THF, benzene, toluene, xylene. Reaction times are, in general, from several minutes to a day, preferably from 20 minutes to 5 hours, however shorter or longer reaction times, if necessary, can be employed. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, diisopropylamine, diisopropylethylamine, piperidine or dimethylaminopyridine, or an alkyl lithium such as n-butyl lithium, sec-butyl lithium, tert-butyl lithium, methyl lithium or lithium diisopropylamide.

SCHEME D

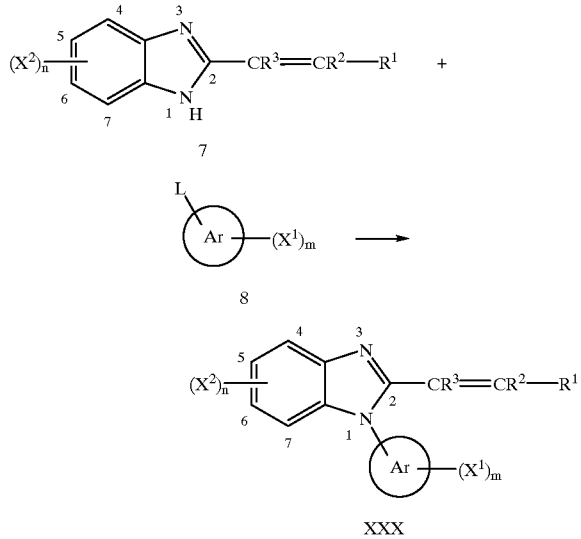

The compounds of formula XXX may also be prepared by reacting a compound of formula 7 with a compound of formula 8 according to the procedure outlined in Scheme D. In Scheme D, the compound of formula 7 may be synthesized by any of the methods described in Schemes A to C herein before. The group L of the compounds of formula 8 is a selected from a suitable displaceable group, for example, a halo or sulfonyloxy group such as fluoro, chloro, bromo, iodo, trifluoromethanesulfonyloxy, methanesulfonyloxy or p-toluenesulfonyloxy group, all readily accessible by conventional methods known to those skilled in the art. Preferably, the instant reaction is conducted in the presence of a suitable base, for example, an alkali or alkaline earth metal hydroxide, alkoxide, carbonate, or hydride, such as, but not limited to, sodium hydroxide, potassium hydroxide, sodium methoxide, sodium ethoxide, potassium tert-butoxide, sodium carbonate, potassium carbonate, sodium hydride or potassium hydride, or in the presence of an organic base an amine such as, but not limited to, triethylamine, diisopropylethylamine diisopropylamine, or dimethylaminopyridine. Preferred reaction-inert solvents include, but are not limited to, acetone, acetonitrile, dichloromethane, N,N-dimethylformamide, N,N-dimethylacetamide, dimethylsulfoxide (DMSO), dioxane, tetrahydrofuran and pyridine. Reaction temperatures are preferably in the range of –40∞ C. to 200∞ C., usually in the range of room temperature (e.g., 25∞ C.)to reflux temperature of solvent, but if necessary, lower or higher temperature can be employed. Reaction time is in general from 1 minute to several days, preferably from 30 minutes to 5 days. Conveniently, the reaction may be conducted in the presence of a suitable catalyst, for example, tetrakis (triphenylphosphine)-palladium(0), dichloro bis (triphenylphosphine)palladium (II), copper (0), cuprous oxide, cuprous iodide, cuprous bromide or cuprous chloride.

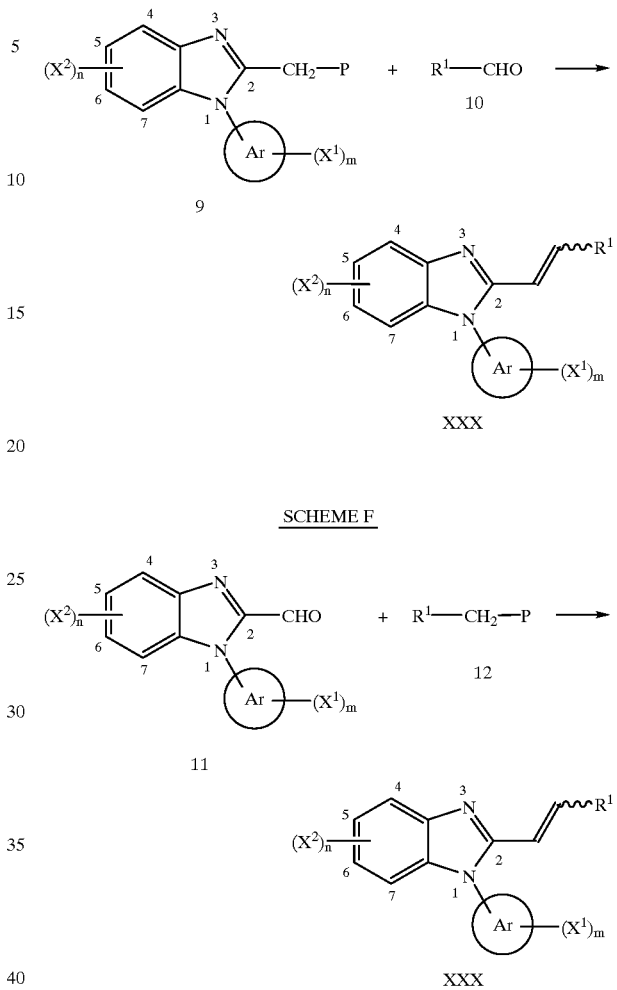

Alternatively, the compounds of formula I may be prepared by the reaction of a suitable aldehyde with a suitable phosphonium (Maryanoff, B. E.; Reitz, A. B. Chem. Rev. 1989, 89, 863) or a dialkyl phosphonate salt (Seguineau, ;Villieras, Tetrahedron Lett. 1988, 29, 477) as shown in Schemes E and F, wherein P is a suitable phoshonium or dialkyl phosphonate salt. For appropriate references see DE939809A.

The starting material of formulae 1, 2, 3, 4, 5, 6, 7, 8, 9, 10, 11 and 12 may be obtained by conventional procedures known to those skilled in the art. The preparation of such starting materials is described within the accompanying non-limiting examples which are provided for the purpose of illustration only. Alternatively, requisite starting materials may be obtained by analogous procedures, or modifications thereof described hereinafter.

A compound of general formula (XL) may be prepared by any synthetic procedure applicable to structure-related compounds known to those skilled in the art. The following representative examples as described hereinafter are illustrative and are not meant to limit the scope of the invention in anyway. Unless otherwise stated, Q, X, Z, R1, and n are as defined above.

SCHEME 21

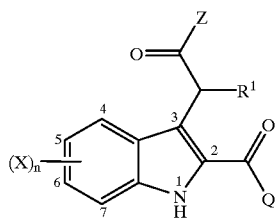

(XL)

In one embodiment, for example, a compound of the formula (XLVI) may be prepared according to the reaction sequences depicted in Scheme 21. (Compound (XLVI) corresponds to a compound (XL) wherein R1 is H, and Z is OH.)

range of room temperature (e.g., 25° C.) to reflux temperature of solvent, preferably 60 to 100° C., but if necessary, lower or higher temperature can be employed. Reaction times are, in general, from one hour to a day, preferably from 4 to 16 hours, however shorter or longer reaction times, if necessary, can be employed. In the immediate instance, the acetoxy compounds of formula (XLIV) is usually obtained as the major product. Compounds of formula (XLIV) can readily be transformed to compounds of formula (XLV) by reduction with a suitable reducing agent, for example, a trialkylsilane, sodium (dimethylamino)naphtalenide, lithium in liquid ammonia, sodium naphtalenide, preferably triethylsilane in a suitable protic solvent, notably, trifluoroacetic acid. Alternatively, the reaction can be conducted in a reaction inert co-solvent such as dichloromethane or 1,2-dichloroethane. Reaction temperatures are generally in the range of room temperature to reflux temperature of solvent, preferably 15 to 100° C., but if necessary, lower or higher temperature can be employed. Reaction times are, in

SCHEME 21

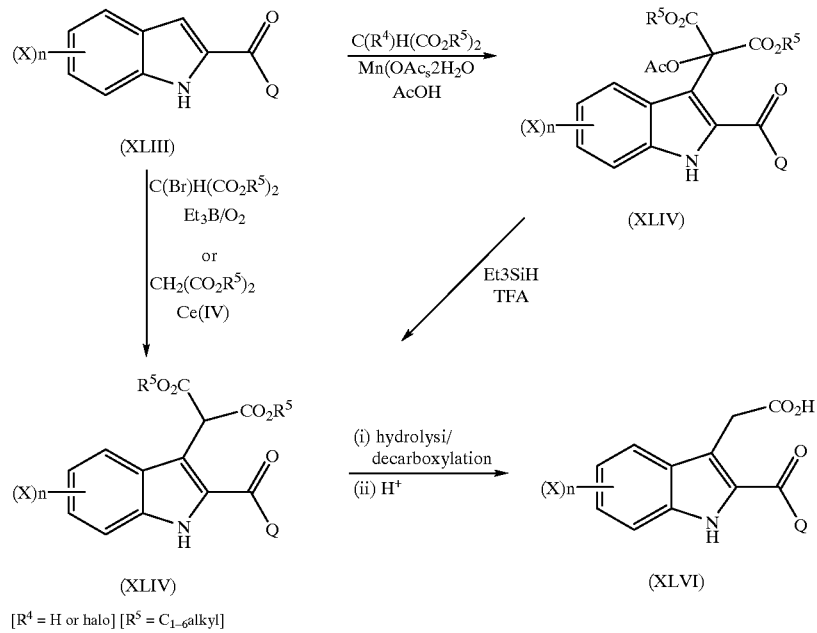

[$R^4$ = H or halo] [$R^5$ = $C_{1-6}$alkyl]

In brief, a compound of formula (XLIII) is subjected to oxidative homolytic malonylation (for leading references see J. M. Muchowski et al; Can. J. Chem., 70, 1838, 1992 and E. Baciocchi et al; J. Org. Chem., 58, 7610, 1993). In one example, a compound of the formula (XLIII) is reacted with a suitable malonyl radical generated from a compound of formula $C(R^4)H(CO_2R^5)_2$, wherein $R^4$ is hydrogen or halogen, preferably chloro, and $R^5$ is C1–6 alkyl, and a manganese(III) agent, preferably manganese (III) triacetate. The manganese(III) agent is usually used in stoichiometric amounts but, alternatively, may be made catalytic by use of a suitable reoxidizing agent such as sodium persulfate, usually in the presence of a co-catalyst such as, a silver(I) salt such as silver nitrate. A preferred reaction solvent is acetic acid; however, acetic acid-acetic anhydride or other protic solvents such as propionic acid can be used. The reaction is preferably conducted in the presence of sodium acetate or potassium acetate, but, may be conducted in solvent alone. Reaction temperatures are generally in the general, from several minutes to a day, preferably from 20 minutes to 5 hours, however shorter or longer reaction times, if necessary, can be employed. Alternatively, a compound of formula (XLV) may be obtained directly from a compound of formula (XLIII) from a malonyl radical generated from (i) a suitable monohalomalonate, preferably, bromomalonate, mediated by aerial oxidation of a trialkylborane such as triethylborane (see B. Giese; In Radicals in organic synthesis: formation of carbon-carbon bonds. Pergamon Press, Oxford. pp. 86–89, 1986, and P. G. Allies and P. B. Brindley; J. Chem. Soc. (B), 1126, 1960) or, (ii) a malonic ester in the presence of a cerium(IV) salt such as cerium (IV) ammonium nitrate (for example, see E. Baciocchi et al; Tetrahedron Lett, 2763, 1986). A compound of formula (XLV) may be readily transformed to a compound of formula (XLVI) by subjection to standard saponification/decarboxylation conditions.

SCHEME 22

Alternatively, as depicted in Scheme 22, a compound of the formula (XLVIII) (a compound (XL) wherein Z is OH), wherein R1 is C1–4 alkyl, may be prepared in an analogous manner to that of a compound of formula (XLVI) employing appropriate reaction conditions as described by illustration herein above from a suitable monoalkylmalonate, wherein R1 is C1–4 alkyl, W is hydrogen or a halogen, preferably bromide, and R5 is C1–6 alkyl, from a compound of formula (XLIII).

SCHEME 22

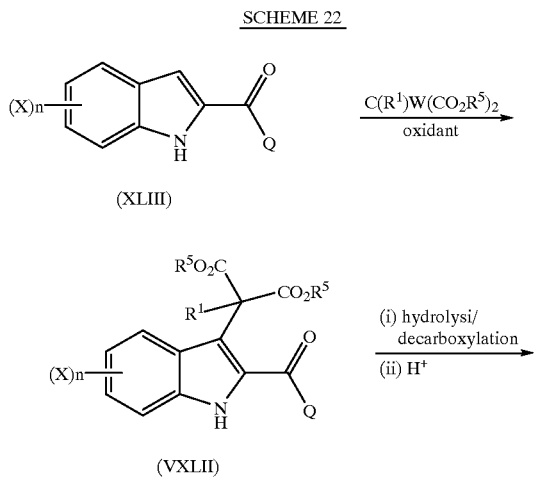

(XLIII)

(VXLII)

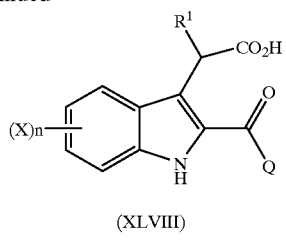

(XLVIII)

[$R^1$ is not hydrogen] [W = H or halo] [$R^5$ = $C_{1-6}$alkyl]

In Scheme 22, for example, the oxidant is manganese (III) agent such as manganese (III) triacetate, or Cerium (IV) agent such as ammonium Cerium (IV) nitrate and Cerium (IV) sulfate.

SCHEME 23

In another embodiment, a compound of formula (XLVIII) is readily accessible from the appropriate 2-aminocinnamic acid ester (XLIX) wherein B is a suitable protecting group, for example, methoxycarbonyl, ethoxycarbonyl, tert-butoxycarbonyl (Boc), benzyloxycarbonyl, phenylsulfonyl, p-toluenesulfonyl, methanesulfonyl, trifluoromethanesulfonyl, methanesulfonyl or trifluoromethanesulfonyl (preferably phenylsulfonyl, p-toluenesulfonyl, methanesulfonyl or trifluoromethanesulfonyl).

SCHEME 23

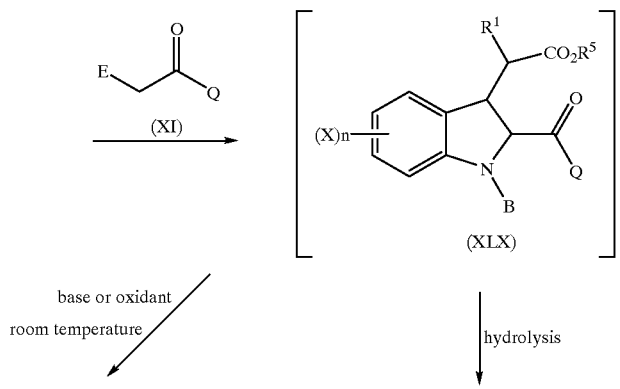

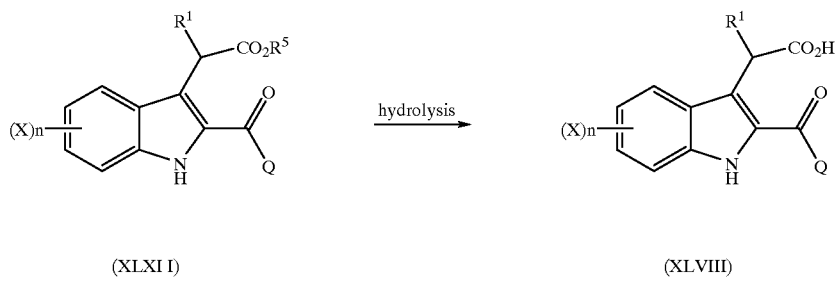

(XLXII)            (XLVIII)

[$R^5$ = $C_{1-6}$alkyl] [B = a suitable protecting group] [E = halogen]

In Scheme 23, the requisite 2-aminocinnamic acid ester (XLIX) is reacted with a compound of formula (XLXI), wherein Q is as defined above and E is halogen, preferably, iodo, bromo or chloro, in the presence of a suitable base. A suitable base is, for example, an alkali or alkaline earth metal alkoxide, carbonate, fluoride or hydride, such as sodium tert-butoxide, potassium tert-butoxide, sodium carbonate, potassium carbonate, cesium carbonate, sodium hydride, potassium fluoride or potassium hydride. Preferred reaction inert solvents include, but are not limited to, acetone, methyl ethyl ketone, acetonitrile, N,N-dimethylformamide (DMF), N,N-dimethylacetamide (DMA), dimethylsulfoxide (DMSO), dioxane or tetrahydrofuran (THF). Reaction temperatures are preferably in the range of −40° C. to reflux temperature of solvent (for example 200° C.), usually in the range of 0° C. to 100° C., but if necessary, lower or higher temperature can be employed. Reaction time is in general from 2 minutes to a day, preferably from 30 minutes to 8 hours, however shorter or longer reaction times, if necessary, can be employed. When the reaction is, for example, conducted at room temperature (e.g., 25° C.) the intermediate indoline (XLX) can be isolated. Reaction at higher temperatures (e.g., 40 to 100° C.) can result in formation of indole (XLXII). Usually the intermediate indoline (XLX) is not isolated but either (i) hydrolyzed with commitant formation of the indole ring directly to a compound of formula (XLVIII) under standard conditions known to those skilled in the art, or (ii) transformed to a compound of formula (XLXII) by using a suitable base, for example, an alkali or alkaline earth metal carbonate such as sodium carbonate, potassium carbonate or cesium carbonate, or an organic base such as 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, pyrrolidine, triethylamine, diisopropylamine, diisopropylethylamine, diethylisopropylamine, Hunig's base, potassium tert-butoxide, sodium tert-butoxide, or the like, or a suitable oxidant such as cerium (IV) ammonium nitrate (CAN), manganese(IV) oxide, manganese(II) triacetate, copper (II) acetate/air, chloranil, 2,3-dichloro-5,6-dicyano-1,4-benzoquinone (DDQ), N-methylmorpholine-N-oxide, or the like (for example, see H. Dumoulin et al; J. Heterocycl. Chem., 32, 1703, 1995; H. Rapoport et al; Tetrahedron Lett., 5053, 1991; P. Martin et al; Helv. Chim. Acta, 77, 111, 1994; Y. Kikugawa et al, J. Chem. Soc. Perkins Trans 1, 7, 1401, 1984; A. Goti et al; Tetrahedron Lett., 6567, 1996; L. S. Liebeskind et al; J. Org. Chem, 61, 2594, 1996). Preferred reaction inert solvents include, but are not limited to, acetone, methyl ethyl ketone, acetonitrile, dioxane or tetrahydrofuran (THF). Reaction temperatures are preferably in the range of 0° C. to reflux temperature of solvent, usually in the range of 15 to 60° C., but if necessary, lower or higher temperature can be employed. Reaction time is in general from several minutes to a day, preferably from 30 minutes to 8 hours, however shorter or longer reaction times, if necessary, can be employed. A compound of formula (XLXII) may be readily hydrolyzed to a compound of formula (XLVIII) under standard conditions.

SCHEME 24

In another embodiment, a compound of formula (XLVIII), wherein Q, X, R1 and n are as defined above, may be prepared as illustrated in Scheme 24.

SCHEME 24

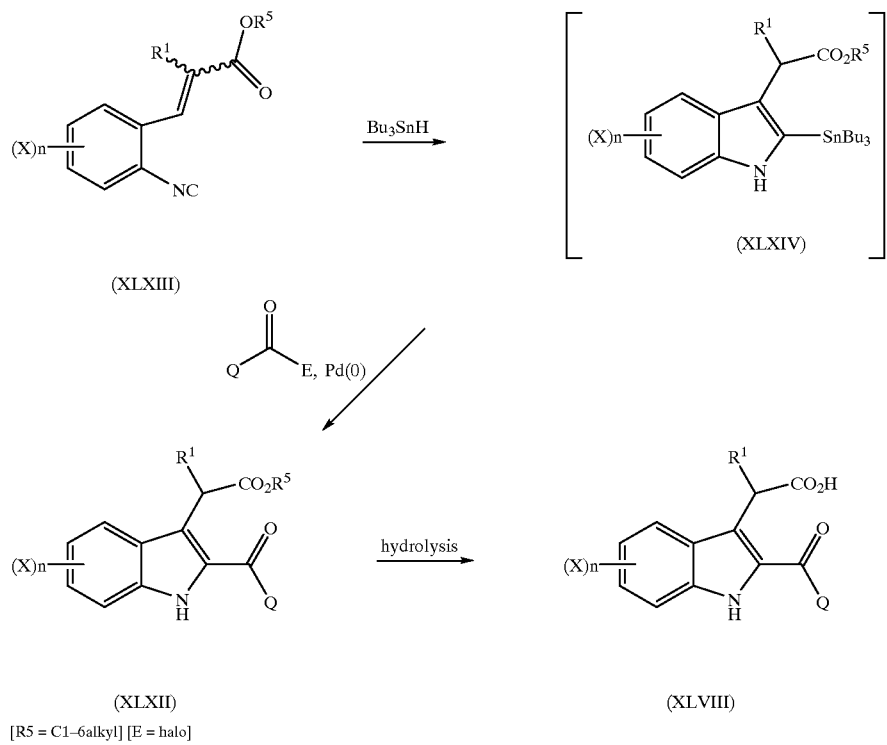

(XLIII)

(XLIV)

(XLII)

(XLVIII)

[R5 = C1–6alkyl] [E = halo]

For example, treatment of a compound of formula (XLIII), wherein R1, R5, X and n are as defined above, with a trialkyltin hydride, e.g., tributyltin hydride usually in the presence of a radical initiator such as, 2,2'-azabisisobutyronitrile (AIBN), affords the intermediate 2-stannylindole (XIV) via an intramolecular radical cyclization as described in J. Am. Chem. Soc., 116, 3127, (1994); T. Fukuyama et al. The intermediate (XLIV) generated in situ is subsequently treated with an acyl halide, wherein Q and E are as defined above, in the presence of a suitable palladium catalyst according to Stille's procedure (for example see. J. K. Stille et al; J. Am. Chem. Soc., 109, 813, 5478, (1987) and J. Am. Chem. Soc., 106, 4833, (1984)) to afford indole (XLII) which may be hydrolyzed to a compound of formula (XLVIII) by conventional procedure.

Examples of the palladium catalyst are tetrakis(triphenylphosphine)palladium(0), dichlorobis(triphenylphosphine)palladium(II), bis (dibenzylideneacetone)palladium(0), benzyl(chloro)bis(triphenylphosphine)palladium(II), bis(acetonitrile)dichloropalladium(II).

SCHEME 25

In another embodiment, a compound of formula (XLVIII), wherein Q, X, R1 and n are as defined above, may be prepared as illustrated in Scheme 25.

SCHEME 25

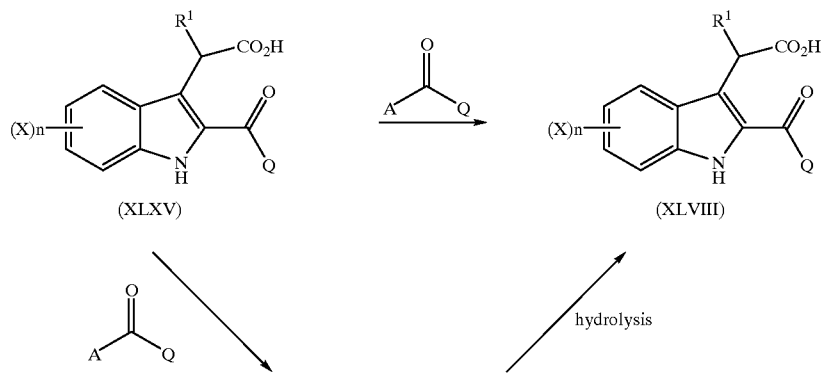

(XLV)

(XLVIII)

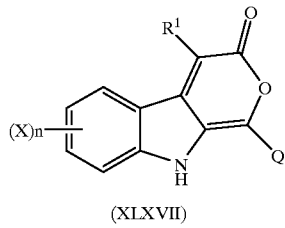

(XLVII)

For example, treatment of a compound (XLXV), wherein R1, X and n are as defined above, is reacted with a compound of formula Q—C(O)—A affords a compound of formula (XLVIII), or a compound of formula (XLXVI) (for example see U.Pindur et al., Liebigs Ann. Chem., 601 (1991) and C. J. Moody et al., J.Chem.Soc.Perkin Trans.I, 3249 (1988)) which may be hydrolyzed to a compound of formula (XLVIII) by conventional procedure (for example see E. B. Fray et al., Tetrahedron, 49, 439 (1993) and U. Pindur et al., J.Heterocycl.Chem., 29, 145 (1992)). In a compound of formula A—C(O)—Q, A is defined such that the compound of A—C(O)—Q is, for example, an acyl halide, carboxylic acid, carboxylic acid anhydride, a mixed carboxylic sulfonic anhydride, or the like. The reaction may be conducted in the presence or absence of catalyst, preferably in the presence of catalyst such as, boron trifluoride-diethyl ether, tin(IV) chloride, aluminum chloride, ferric chloride, zinc chloride, iodine, iron, or the like. Preferred reaction inert solvents include, but are not limited to, diethyl ether, dichloromethane, 1,2-dichloroethane, carbon disulfide, nitrobenzene or nitromethane. Reaction temperatures are preferably in the range of −78 to 210° C., usually in the range of −10° C. to reflux temperature of solvent, but if necessary, lower or higher temperature can be employed. Reaction time is in general from several minutes to a day, preferably from 30 minutes to 8 hours, however shorter or longer reaction times, if necessary, can be employed.

SCHEME 26

Acetic acid compounds of formulae (XLVI) and (XLVIII) as described in the aforementioned schemes may be readily transformed to the corresponding amide, compounds of formulae (XLXVII) and (XLXVIII), or ester, compound of formula (XII), by any conventional method known to those skilled in the art.

SCHEME 26

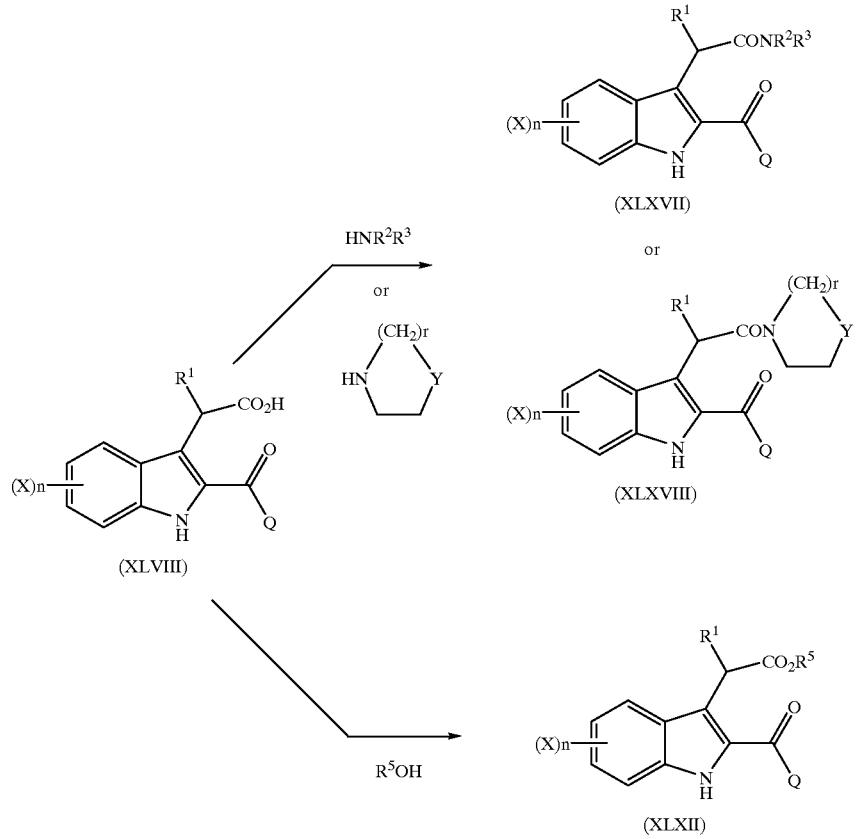

[R⁵ = C₁₋₆alkyl]

As depicted in Scheme 26, compounds of formulae (XLXVII) and (XLXVIII) can be readily prepared by treating the requisite acetic acid compounds of formulae (XLVI) and (XLVIII) with an appropriate amine, wherein R2, R3, Y and r are as described herein before, in the presence of a suitable coupling reagent such as, but not limited to, 1-(dimethylaminopropyl)-3-ethylcarbodiimide (WSC), N,N'-dicyclohexylcarbodiimidazole (DCC), carbonyldiimidazole, diethylphosphorocyanidate (DEPC), or the like. Preferred reaction inert solvents include, but are not limited to, acetone, acetonitrile, dichloromethane, 1,2-dichloroethane, N,N-dimethylformamide (DMF), N,N-dimethylacetamide (DMA), dimethylsulfoxide (DMSO), dioxane, tetrahydrofuran (THF) or pyridine. Reaction temperatures are preferably in the range of −40 to 150° C., usually in the range of 15° C. to reflux temperature of solvent, but if necessary, lower or higher temperature can be employed. Reaction time is in general from several minutes to a day, preferably from 30 minutes to 8 hours, however shorter or longer reaction times, if necessary, can be employed. The compounds of formulae (XLXV) and (XLVIII) can also be readily transformed to the corresponding ester by conventional methods.

optionally substituted by 1 to 3 (C1–C4)alkyl groups, preferably pyridine. Suitable electrophiles include methanesulfonyl chloride or anhydride, or phenylsulfonyl chloride wherein the phenyl moiety of said phenylsulfonyl optionally includes 1 or 2 substituents selected from halo, nitro, and (C1–C4)alkyl. Suitable solvents include dichloromethane, dichloroethane, methyl t-butyl ether, diisopropyl ether or toluene, preferably dichloromethane. The temperature of the aforesaid reaction may range from about 0° C. to about 50° C., preferably about room temperature (20–25° C.) for a period of about 1 to 30 hours, preferably about 18 hours.

The compound of formula 7-IV is prepared from a compound of formula 7-II by treatment with a first base and an alkylating agent of the formula 7-III in the presence of a solvent followed by reaction with a second base followed by reaction with an acid. Suitable first bases include potassium carbonate, potassium bicarbonate, sodium bicarbonate, sodium carbonate or cesium carbonate, preferably potassium carbonate. Suitable solvents include N,N-dimethylacetamide, N,N-dimethylformamide, methyl ethyl ketone, acetone or tetrahydrofuran, preferably N,N-dimethylaetamide. The aforesaid reaction is performed at a temperature ranging from about 0° C. to about 100° C.,

SCHEME 27

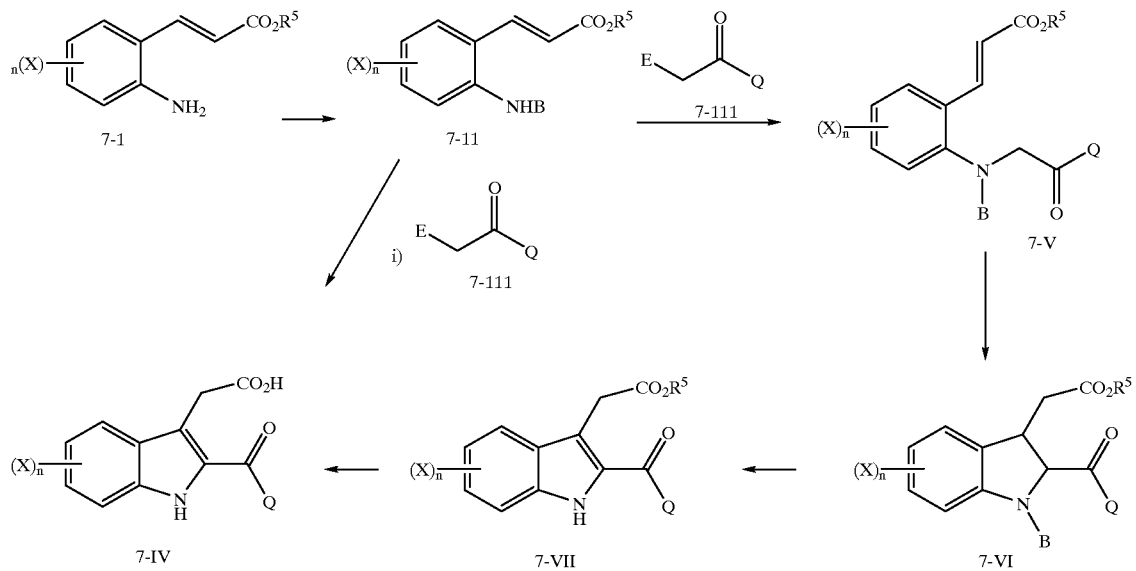

(wherein B is a suitable protecting group, R5 is C1–6 alkyl, E is halo, Q, X and n is as defined above.)

In Scheme 7, the starting material of formula 7-I may be prepared according to methods familiar to those of ordinary skill in the art, including one or more synthetic procedures described in R. W. Carling, P. D. Leeson, K. Moore, J. D. Smith, C. R. Moyes, J. Med. Chem., 1993, pages 3397–3408.

The compound of formula 7-II is prepared from a compound of formula 7-I by treatment with a base and an electrophile in a suitable solvent. Suitable bases include such as triethylamine, diisopropylethylamine, or pyridine preferably room temperature (20–25° C.), for a period of time of about 10 minutes to 5 hours, typically 15 minutes. Suitable second bases include an aqueous solution of a base such as sodium hydroxide, potassium hydroxide, sodium carbonate, potassium carbonate, sodium t-pentoxide (followed by water), sodium methoxide (followed by water) or potassium t-butoxide (followed by water), preferably sodium hydroxide. The reaction with the second base is performed at a temperature ranging from about 20° C. to about 120° C., preferably 100° C., for a period of time of about 1 hour to 24 hours, typically 8 hours. Suitable acids include aqueous hydrochloric acid, hydrobromic acid, sulfuric acid or ammonium chloride, preferably hydrochloric acid. The reaction with the acid is performed at a temperature ranging from about 0° C. to about 50° C., preferably about 20° C. to about 25° C., for a period of time of about ½ hour to about 6 hours, typically about 1 hour.

Alternatively, the conversion of the compound of formula 7-II to a compound of formula 7-IV can be accomplished stepwise. The compound of formula 7-V may be prepared from a compound of formula 7-II by treatment with a base and an alkylating agent of formula 7-III in the presence of a solvent. Suitable bases include potassium carbonate, potassium bicarbonate, sodium bicarbonate, sodium carbonate, or cesium carbonate, preferably potassium carbonate. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to about 50° C., preferably room temperature (20–25° C.), for a period of time of about 10 minutes to 40 minutes, typically 30 minutes.

The compound of formula 7-VI is prepared from a compound of formula 7-V by reaction with a base in the presence of a solvent. Suitable bases include potassium carbonate, potassium bicarbonate, sodium bicarbonate, sodium carbonate or cesium carbonate, preferably potassium carbonate. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to about 50° C., preferably room temperature (20–25° C.), for a period of time of about 1 hour to 6 hours, preferably 4 hours.

The compound of formula 7-VII is prepared from a compound of formula 7-VI by reaction with a base in a suitable solvent. Suitable bases include 1,8-diazabicyclo[5.4.0]undec-7-ene, 1,5-diazabicyclo[4.3.0]non-5-ene, 1,1,3,3-tetramethylguanidine, sodium t-pentoxide, sodium methoxide or potassium t-butoxide, preferably 1,8-diazabicyclo[5.4.0]undec-7-ene methoxide or potassium t-butoxide. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to 100° C., preferably room temperature (20–25° C.), for a period of 30 minutes to 5 hours, preferably 1 hour.

The compound of formula 7-IV is prepared from a compound of formula 7-VII by treatment with a base in a suitable solvent. Suitable bases include sodium hydroxide, potassium hydroxide, sodium carbonate, potassium carbonate, sodium bicarbonate, potassium bicarbonate, sodium t-pentoxide, sodium methoxide, sodium ethoxide or potassium t-butoxide, preferably sodium hydroxide. Suitable solvents include an aqueous mixture of methanol, ethanol, isopropyl alcohol or tetrahydrofuran, preferably methanol, containing water. The temperature of the aforesaid reaction may range from about 10° C. to 100° C., preferably room temperature (20–25° C.), for a period of 12 to 48 hours, preferably 24 hours, to provide the carboxylate salt of compound of formula 7-IV which can then be treated with an acid to provide the compound of formula 7-IV.

The compound of formula 7-VI has asymmetric atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. The use of all such isomers, including diastereoisomer mixtures and pure enantiomers, are considered to be part of the present invention.

A compound of formula (L) may be prepared by any synthetic procedure applicable to structure-related compounds known to those skilled in the art. The following representative examples as described in Schemes 28–34 are illustrative of the invention in which, unless otherwise stated, Ar, X1, X2, 3 and Y are as defined herein before. For the synthesis of compounds of related-structure to compounds of the present invention, see "Benzimidazoles and Congeneric Tricyclic Compounds" in Heterocyclic Compounds, Vol. 40, Preson, P. N. Ed., John Wiley & Sons, NY, 1981.

SCHEME 28

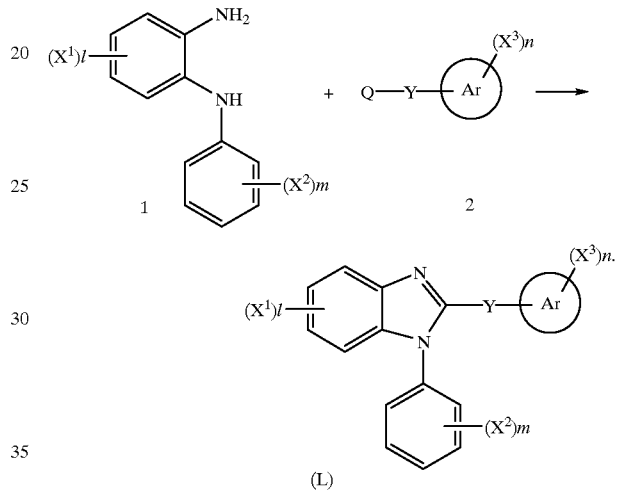

(L)

For example, the compound of formula (L) may be prepared according to the reaction outlined in Scheme I. In the instant example, a phenylenediamine compound of formula 1 is reacted with a compound of formula 2 wherein the group Q is a residue of a carboxylic acid, carboxylic acid ester, carboxamide, carboxylic acid anhydride, carboxylic acid chloride, orthoester, imino ether, a carbaldehyde or the like. The reaction may be conducted in the presence or absence of a reaction inert solvent. Preferred reaction inert solvents include benzene, toluene, xylene, pyridine, 1,2-dichloroethane, o-dichlorobenzene, nitrobenzene and dichloromethane. Preferably, the reaction is conducted in the presence of a promoter such as hydrochloric acid, polyphosphoric acid, phosphorous pentoxide, phosphorous oxychloride, polyphosphoric acid ethyl ether, polyphosphoric acid trimethylsilyl ether, p-toluenesulfonic acid, zinc (II) chloride or the like. When a compound of formula 2 is carboxaldehyde, the reaction may be conducted in the presence of an oxidant such as cupric acetate, chloranil, or the like. Reaction temperatures are preferably in the range of 40° C. to 250° C., usually in the range of 20° C. to 200° C., but if necessary, lower or higher temperature can be employed. Reaction time may vary, in general, from 5 minutes to 6 days, preferably from 20 minutes to 1 day. Alternatively, the reaction may be conducted in a sealed tube or an autoclave at medium (1–10 kg/cm2) to high pressure (20–200 kg/cm2) to accelerate it, preferably in the range of 2 to 150 kg/cm2.

SCHEME 29

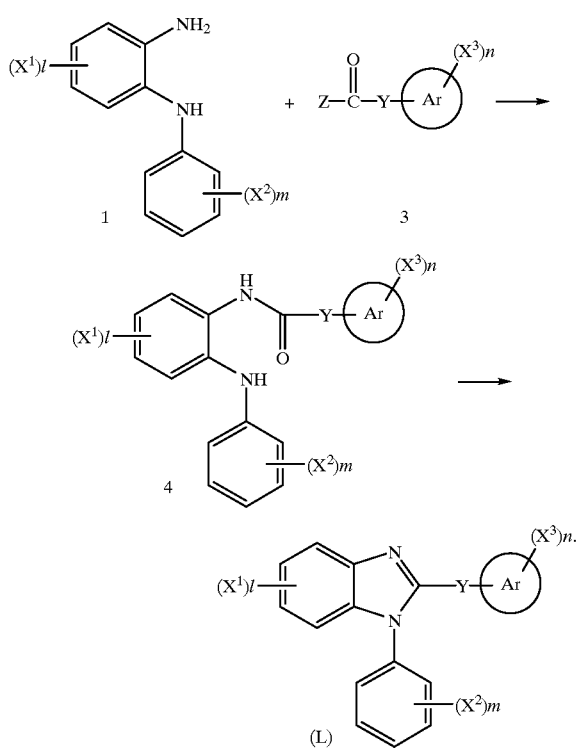

Alternatively, the compounds of formula (L) may be prepared by a two step procedure from phenylenediamine compounds of formula 1 via the (N-acylamino)phenylamine compounds of formula 4 as shown in Scheme 29. In the first step, a phenylenediamine compound of formula 1 is reacted with a compound of formula 3, wherein Z is selected from halo, —OH, —OR(R is C1–4 alkyl), —NH2, and —OC(O)Y—Ar—(X3)n, by conventional methods known to those skilled the art to form amides of formula 4. For example, when a compound of formula 3 is carboxylic acid (i.e, Z is OH), the reaction is preferably conducted in the presence of a coupling reagent such as 1-(dimethylaminopropyl)-3-ethylcarbodiimide (WSC), N,N'-dicyclohexylcarbodiimidazole (DCC), carbonyldiimidazole, cyanophosphonic acid diethyl ester or the like. Preferred reaction-inert solvents include acetone, acetonitrile, dichloromethane, N,N-dimethylformamide, N,N-dimethylacetamide, dimethylsulfoxide, dioxane, tetrahydrofuran and pyridine.

In next step, the compounds of formula (L) are provided by cyclization of the compounds of formula 4. The reaction may be conducted in the presence or absence of a reaction inert solvent. Preferred reaction inert solvents include benzene, toluene, xylene, pyridine, 1,2-dichloroethane, o-dichlorobenzene, nitrobenzene, dichloromethane and ethanol. Preferably, the reaction is conducted in the presence of a promoter such as of hydrochloric acid, polyphosphoric acid, phosphorous pentoxide, phosphorous oxychloride, polyphosphoric acid ethyl ether, polyphosphoric acid trimethylsilyl ether, thionyl chloride, p-toluenesulfonic acid, or the like. Alternatively, the cyclization reaction may be performed under Mitsunobu-type reaction conditions, for example, in the presence of triphenylphosphine and diethyl azodicarboxylate. Reaction temperatures are preferably in the range of −40° C. to 250° C., usually in the range of 20° C. to 200° C., but if necessary, lower or higher temperature can be employed. Reaction time may vary, in general, from 5 minutes to 6 days, preferably from 20 minutes to 1 day.

SCHEME 30

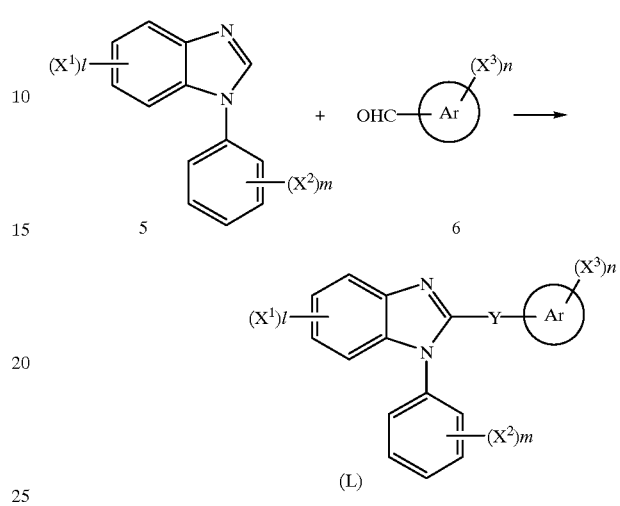

In another embodiment, the compounds of formula (L) wherein Y is C(H)=C(H) may be prepared as shown in Scheme 30. Thus, 2-methylbenzimidazole compounds of formula 5 are reacted with aldehydes of formula 6 in the presence or absence of base. When the said reaction is conducted in the absence of base, the reaction is preferably performed in a sealed tube or an autoclave at medium (1–10 kg/cm2) to high pressure (20–200 kg/cm2), preferably in the range of 2 to 150 kg/cm2. The reaction may be conducted in the presence or absence of a reaction inert solvent. Preferred reaction inert solvents include benzene, toluene, xylene, chlorobenzene, nitrobenzene, acetic acid, acetic anhydride and the like. Reaction temperatures are generally in the range of −100° C. to 250° C., preferably in the range of 20° C. to 200° C., but if necessary, lower or higher temperature can be employed. Reaction time may vary, in general, from 5 minutes to a day, preferably from 20 minutes to 5 hours, however shorter or longer reaction times if necessary can be employed. When the said reaction is conducted in the presence of base, reaction temperatures are generally in the range of −100° C. to 250° C., preferably in the range of −80° C. to 20° C., but if necessary, lower or higher temperature can be employed. Preferred reaction inert solvents include THF, benzene, toluene and xylenes. Reaction time may vary, in general, from 5 minutes to one day, preferably from 20 minutes to 5 hours, however shorter or longer reaction time, if necessary, can be employed. Preferred bases include, for example, an alkali or alkaline earth metal hydroxide, alkoxide, carbonate or hydride, such as sodium hydroxide, potassium hydroxide, sodium methoxide, sodium ethoxide, potassium tert-butoxide, sodium carbonate, potassium carbonate, sodium hydride or potassium hydride; an amine such as triethylamine, diisopropylamine, diisopropylethylamine, piperidine or dimethylaminopyridine; and an alkyl lithium such as n-butyl lithium, sec-butyl lithium, tert-butyl lithium, methyl lithium or lithium diisopropylamide.

SCHEME 31

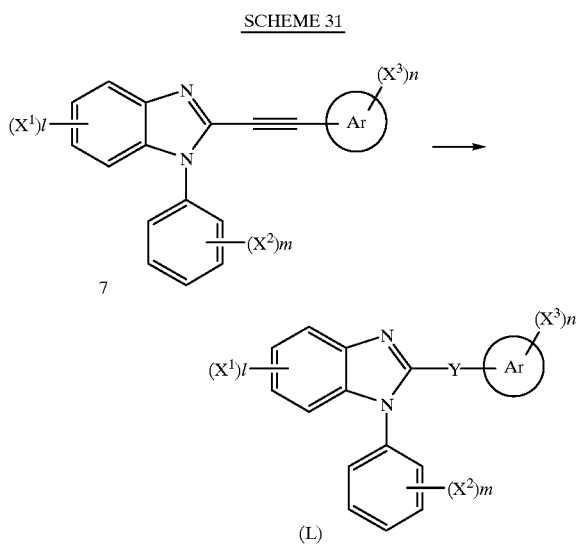

In another embodiment, the compounds of formula (L) wherein Y is C(H)=C(H) may be prepared by partial hydrogenation of a compound of formula (L) wherein Y is C—≡—C as depicted in Scheme 31. Preferred catalysts include, for example, nickel-based catalysts such as P-2 nickel and nickel boride (Choi,J; Yoon, N. M. Tetrahedron Lett., 1996, 37, 1057) and palladium-based catalysts such as Lindlar catalyst and Pd/W. Preferred reaction-inert solvents include, for example, water, methanol, ethanol, acetone, acetonitrile, ethyl acetate, dichloromethane, dioxane, tetrahydrofuran, diethyl ether and diisopropyl ether. Reaction temperatures are preferably in the range of –40° C. to 200° C., usually in the range of 20° C. to reflux temperature of solvent, but if necessary, lower or higher temperature can be employed. Reaction time is in general from 5 minutes to 6 days, preferably from 100 minutes to 5 days.

The compounds of formula (L) may also be prepared by reacting a compound of formula 8 with a compound of formula 9 according to the procedure outlined in Scheme 32. In Scheme 32, the compound of formula 8 may be synthesized by any of the methods described in Schemes 28 to 31 herein before. The group L of the compounds of formula 9 is selected from suitable displaceable groups, for example, halo such as fluoro, chloro, bromo or iodo, and sulfonyloxy such as trifluoromethanesulfonyloxy, methanesulfonyloxy or p-toluenesulfonyloxy, all readily accessible by conventional methods known to those skilled in the art. Preferably, the instant reaction is conducted in the presence of a suitable base, for example, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or in the presence of an organic base an amine such as triethylamine, diisopropylethylamine diisopropylamine, or dimethylaminopyridine. Preferred reaction-inert solvents include acetone, acetonitrile, dichloromethane, N,N-dimethylformamide, N,N-dimethylacetamide, dimethylsulfoxide, dioxane, tetrahydrofuran and pyridine. Reaction temperatures are preferably in the range of –40° C. to 200° C., usually in the range of 20° C. to reflux temperature of solvent, but if necessary, lower or higher temperature can be employed. Reaction time is in general from 5 minutes to 6 days, preferably from 30 minutes to 5 days. Conveniently, the reaction may be conducted in the presence of a suitable catalyst, for example, tetrakis(triphenylphosphine)-palladium, bis(triphenylphosphine)palladium (II) chloride, copper (0), cuprous chloride, cuprous oxide, cuprous iodide, cuprous bromide or cuprous chloride.

SCHEME 32

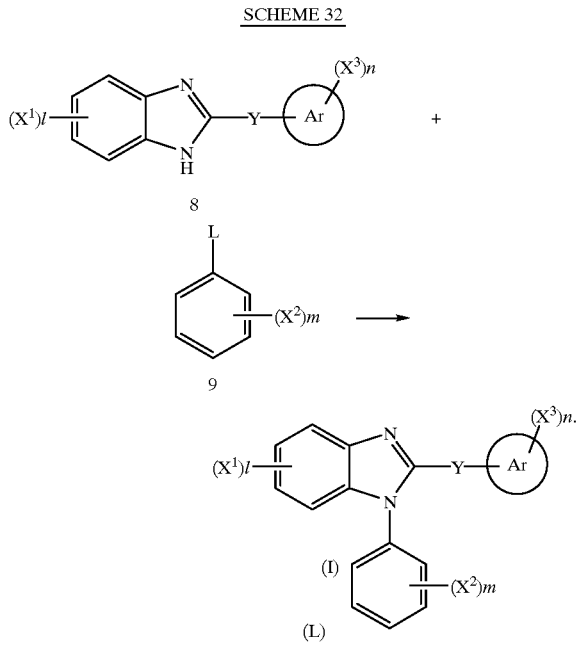

SCHEME 33I

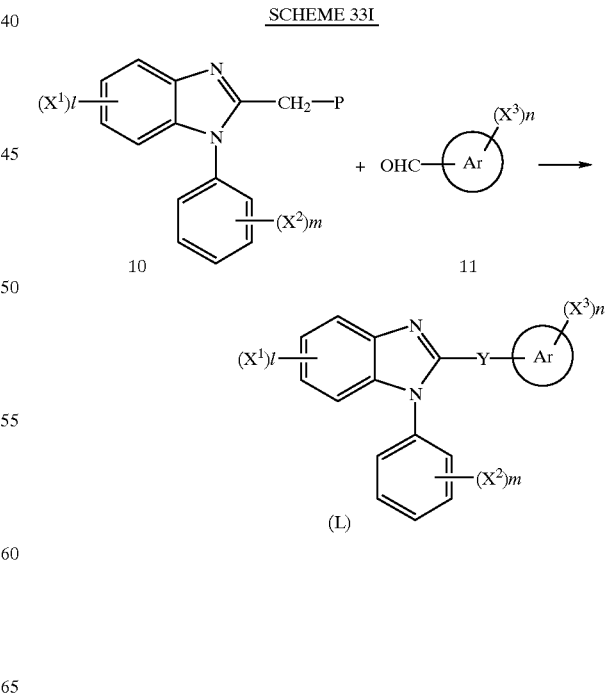

SCHEME VII

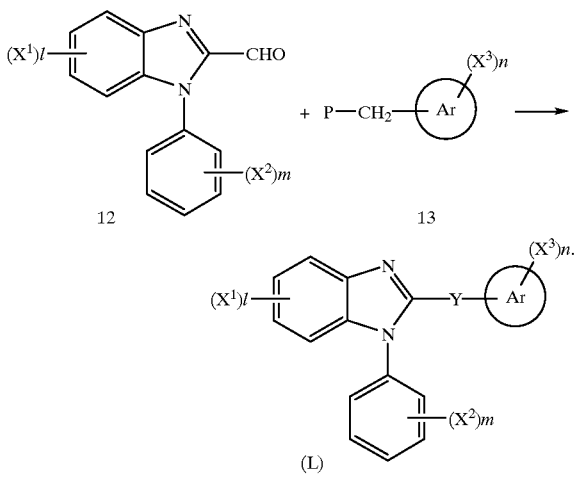

Alternatively, the compounds of formula (L) wherein Y is C(H)=C(H) may be prepared by the reaction of a suitable aldehyde with a suitable phosphonium (Maryanoff, B. E.; Reitz, A. B. Chem. Rev. 1989, 89, 863) or a dialkyl phosphonate salt (Seguineau, Villieras, Tetrahedron Lett. 1988, 29, 477) as shown in Schemes 33 and 34, wherein P is a suitable phoshonium or dialkyl phosphonate salt. For appropriate references, see DE1939809A.

The term "treating", as used herein, refers to retarding or reversing the progress of, or alleviating or preventing either the disorder or condition to which the term "treating" applies, or one or more symptoms of such disorder or condition. The term "treatment", as used herein, refers to the act of treating a disorder or condition, as the term "treating" is defined above.

This invention relates both to methods of treating migraine in which the $5HT_1$ receptor agonist, caffeine with a cyclooxygenase-2 (COX-2) inhibitor are administered together, as part of the same pharmaceutical composition, as well as to methods in which these three active agents are administered separately, as part of an appropriate dose regimen designed to obtain the benefits of the combination therapy. The appropriate dose regimen, the amount of each dose administered, and the intervals between doses of the active agents will depend upon the $5HT_1$ agonist and the COX-2 inhibitor being used, the type of pharmaceutical formulations being used, the characteristics of the subject being treated and the severity of the migraine. Generally, in carrying out the methods of this invention, the $5HT_1$ receptor agonist will be administered orally to an average 70 kg adult human in an amount ranging from about 0.5 to about 100 mg per day, in single or divided doses, and the caffeine and COX-2 inhibitor will be administered in single or divided doses. Caffeine will be administered in amounts ranging from about 15 mg to about 200 mg per day, preferably about 30 mg to about 100 mg per day, depending on the severity of the headache and the route of administration. COX-2 inhibitors will generally be administered in amounts ranging from about 10 to about 300 mg per day, depending on the COX-2 inhibitor, severity of the headache and the route of administration. The COX-2 inhibitors can be administered orally, intranasally, intravenously, as a rectal suppository or using a "flash" formulation (i.e., allowing the medication to dissolve in the mouth without the need to use water.)

The following tables exemplify preferred dosage ranges of certain specific $5HT_1$ agonists when used in combination with cyclooxygenase-2 (COX-2) inhibitors

TABLE 1

| $5HT_1$ AGONIST | DOSAGE RANGE FOR MEDICATION TAKEN | DOSAGE RANGE FOR MEDICATION TAKEN INTRANASALLY (mg) |
|---|---|---|
| Eletriptan | 20 to 80 | — |
| Rizatriptan | 5 to 10 | — |
| Zolmitriptan | 1 to 5 | — |
| Sumatriptan | 25 to 100 | 5 to 20 |
| Naratriptan | 1 to 5 | — |
| Dihydroergotamine | — | 0.5 to 2 |
| Ergotamine | 0.5 to 2 | — |

TABLE 2

| CAFFEINE | DOSAGE RANGE (mg) |
|---|---|
| | 15 to 200 |

TABLE 3

| COX2-Inhibitors | DOSAGE RANGE (mg) P.O. |
|---|---|
| VIOXX ™ | 10 to 100 |

The $5HT_1$ receptor agonists with caffeine and a cyclooxygenase-2 (COX-2) inhibitor that are employed in the pharmaceutical compositions and methods of this invention, and their pharmaceutically acceptable salts, may be administered alone (three active agents administered together or separately) or in combination with pharmaceutically acceptable carriers or diluents. They may be formulated in a conventional manner using one or more pharmaceutically acceptable carriers. Such compounds may be administered orally, buccally, intranasally, parenterally (e.g., intravenously, intramuscularly or subcutaneously) or rectally, or in a form suitable for administration by inhalation or insufflation.

For oral administration (three active agents administered together or separately), the pharmaceutical compositions may take the form of, for example, tablets or capsules prepared by conventional means with pharmaceutically acceptable excipients such as binding agents e.g., pregelatinised maize starch, polyvinylpyrrolidone or hydroxypropyl methylcellulose); fillers (e.g., lactose, microcrystalline cellulose or calcium phosphate), lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition (three active agents administered together or separately) may take the form of tablets or lozenges formulated in a conventional manner.

The 5HT$_1$ agonists of the invention and their salts with a cyclooxygenase-2 (COX-2) inhibitor may be formulated for parenteral administration (three active agents administered together or separately) by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredients (three active agents administered together or separately) may be in powder form for reconstitution with a suitable vehicle, e.g., sterile pyrogen-free water, prior to use.

The 5HT$_1$ agonists of this invention and their salts with caffeine and a cyclooxygenase-2 (COX-2) inhibitor may also be formulated (three active agents administered together or separately) in rectal compositions such as suppositories or retention enemas, e.g., containing conventional suppository bases such as cocoa abutter or other glycerides.

For intranasal administration or administration by inhalation, the active compounds of the invention (three active agents administered together or separately) are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Aerosol formulations (three active agents administered together or separately) for the treatment of migraine in the average adult human are preferably made so that each metered dose or "puff" of aerosol contains 20 μg to 1000 μg of the active compounds of the invention. The overall daily dose with an aerosol will generally be within the range of about 100 μg to 10 mg. Administration may be several times daily, for example, 2, 3, 4 or 8 times, giving, for example, 1, 2 or 3 doses each time.

The 5-HT$_1$ receptor agonist activity of a compound or salt can be measured in in vitro receptor binding assays as described for the 5-HT$_{1A}$ receptor, using rat cortex as the receptor source and [$^3$H]8-OH-DPAT as the radioligand (D. Hoyer et al., *Europ. J. Pharmacol.*, 1985; 118: 13), and as described for the 5-HT$_{1D}$ receptor, using bovine caudate as the receptor source and [$^3$H]5-HT as the radioligand (R. E. Heuring and S. J. Peroutka, *J. Neuroscience*, 1987; 7: 894).

The in vitro activity of a compound at the 5-HT$_{1D}$ binding site may be determined according to the following procedure. Bovine caudate tissue is homogenized and suspended in 20 volumes of a buffer containing 50 mM TRIS.hydrochloride (tris[hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS.hydrochloride containing 0.01 percent ascorbic acid with a final pH of 7.7 and also containing 10 mM pargyline and 4 mM calcium chloride (CaCl$_2$). The suspension is kept on ice at least 30 minutes prior to use.

The inhibitor, control or vehicle is then incubated according to the following procedure. To 50 ml of a 20 percent dimethylsulfoxide (DMSO)/80 percent distilled water solution is added 200 ml of tritiated 5-hydroxytryptamine (2 nM) in a buffer of 50 mM TRIS.hydrochloride containing 0.01 percent ascorbic acid at pH 7.7 and also containing 10 mM pargyline and 4 mM calcium chloride, plus 100 nM of 8-hydroxy-DPAT (dipropylaminotetraline) and 100 nM of mesulergine. To this mixture is added 750 ml of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters). The pellet is then washed three times with 4 ml of a buffer of 50 mM TRIS.hydrochloride at pH 7.7. The pellet is then placed in a scintillation vial with 5 ml of scintillation fluid (aquasol 2) and allowed to sit overnight. The percent inhibition can be calculated for each dose of the compound. An IC$_{50}$ value can then be calculated from the percent inhibition values.

The ability of a compound or salt to bind to 5-HT$_{1A}$ receptors can be determined according to the following procedure. Rat brain cortex tissue is homogenized and divided into samples of 1 gram lots and diluted with 10 volumes of 0.32 M sucrose solution. The suspension is then centrifuged at 900 G for 10 minutes and the supernatant separated and recentrifuged at 70,000 G for 15 minutes. The supernate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 mm pargyline and kept on ice.

The tissue is then incubated according to the following procedure. Fifty microliters of control, inhibitor, or vehicle (1 percent DMSO final concentration) is prepared at various dosages. To this solution is added 200 ml of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 ml of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. IC$_{50}$ values are calculated from the percent inhibition values.

The agonist and antagonist activities compounds at 5-HT$_{1A}$ and 5-HT$_{1D}$ receptors can be determined using a single saturating concentration according to the following procedure. Male Hartley guinea pigs are decapitated and 5-HT$_{1A}$ receptors are dissected out of the hippocampus, while 5-HT$_{1D}$ receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 mM GTP and 0.5–1 microcuries of [32P]-ATP (30 Ci/mmol: NEG-003—New England Nuclear). Incubation is initiated by the addition of tissue to siliconized microfuge tubes (in triplicate) at 30° C. for 15 minutes. Each tube receives 20 mL tissue, 10 mL drug or buffer (at 10× final concentration), 10 mL 32 nM agonist or buffer (at 10× final concentration), 20 mL forskolin (3 mM final concentration) and 40 mL of the preceding reaction mix. Incubation is terminated by the addition of 100 mL 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 mM (R)-8-OH-DPAT for 5-$HT_{1A}$ receptors, and 320 nM 5-HT for 5-$HT_{1D}$ receptors. Percent inhibitions by the test compounds are then calculated in relation to the inhibitory effect of (R)-8-OH-DPAT for 5-$HT_{1A}$ receptors or 5-HT for 5-$HT_{1D}$ receptors. The reversal of agonist induced inhibition of forskolin-stimulated adenylate cyclase activity is calculated in relation to the 32 nM agonist effect.

Compounds can be tested for in vivo activity for antagonism of 5-$HT_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a 5-$HT_{1D}$ agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-$HT_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and 5-$HT_{1D}$ agonists are given concurrently and temperatures are taken at 30, 60, 120 and 240 minutes later.

Data are analyzed with two-way analysis of variants with repeated measures in Newman-Keuls post hoc analysis.

The 5-$HT_1$ agonist activity can be determined by the in vitro receptor binding assays, as described for the 5-$HT_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-$HT_{1D}$ receptor using bovine caudate as the receptor source and [3H] serotonin as the radioligand [R. E. Heuring and S. J. Peroutka, *J. Neuroscience*, 7, 894 (1987)]. Of the active compounds tested, all exhibited an $IC_{50}$ in either assay of 1 mM or less.

Compounds and salts can be evaluated as anti-migraine agents by testing the extent to which they mimic sumatriptan in contracting the dog isolated saphenous vein strip (P. P. A. Humphrey et al., Br. *J. Pharmacol.*, 1988; 94: 1128.). This effect can be blocked by methiothepin, a known serotonin antagonist. Sumatriptan is known to be useful in the treatment of migraine and produces a selective increase in carotid vascular resistance in the anaesthetized dog. It has been suggested that this is the basis of its efficacy by Fenwick et al., *British Journal of Pharmacology.*, 1989; 96: 83.

The activity of the COX-2 inhibitors of the present invention may be demonstrated by the following assays.

Human Cell Based COX-1 Assay

Human peripheral blood is obtained from healthy volunteers and diluted to 1/10 volume with 3.8% sodium citrate solution. The platelet-rich plasma is immediately obtained and washed with 0.14 M sodium chloride containing 12 mM Tris-HCl (pH 7.4) and 1.2 mM EDTA. Platelets are then washed with platelet buffer (Hanks buffer (Ca free) containing 0.2% BSA and 20 mM Hepes). Finally, the human washed platelets (HWP) are suspended in platelet buffer at the concentration of $2.85 \times 10^8$ cells/ml is stored at room temperature until use. The HWP suspension (70 μl aliquots, final $2.0 \times 10^7$ cells/ml) is placed in a 96-well U bottom plate and 10 μl aliquots of 12.6 mM CaCl2 added. Platelets are incubated with A23187 (final 10 μM, Sigma) with test compound (0.1–100 μM) dissolved in DMSO (final concentration; less than 0.01%) at 37° C. for 15 minutes. The reaction is stopped by addition of EDTA (final 7.7 mM) and TxB2 in the supernatant quantitated by using a radioimmunoassay kit (Amersham) according to the manufacturer's procedure.

Human Cell Based COX-2 Assay

Inhibition of COX-2 Activity After Induction of COX-2 by hIL-1β

The human cell based COX-2 assay is carried out as previously described (Moore et al., *Inflam. Res.*, 45, 54, 1996). Confluent human umbilical vein endothelial cells (HUVECs, Morinaga) in a 96-well U bottom plate are washed with 100 μl of RPMI1640 containing 2% FCS and incubated with hIL-1β (final concentration 300 U/ml, R & D Systems) at 37° C. for 24 hr. After washing, the activated HUVECs are stimulated with A23187 (final concentration 30 μM) in Hanks buffer containing 0.2% BSA, 20 mM Hepes and test compound (0.1 nM–100 μM) dissolved in DMSO (final concentration; less than 0.01%) at 37° C. for 15 minutes. 6-Keto-PGF1α, stable metabolite of PGI2, in the supernatant is quantitated after adequate dilution by using a radioimmunoassay kit (Amersham) according to the manufacturer's procedure.

Inhibition of COX-2 During the Induction Phase

Confluent human umbilical vein endothelial cells (HUVECs, Morinaga) in a 96-well U bottom plate are washed with 100 μl of RPMI1640 containing 2% FCS and test compound (0.1 nM–100 μM) dissolved in DMSO (final concentration; less than 0.01 %), and incubated with hIL-1β (final concentration 300 U/ml, R & D Systems) at 37° C. for 24 hr. After washing, the HUVECs are stimulated with A23187 (final concentration 30 μM) in Hanks buffer containing 0.2% BSA and 20 mM Hepes at 37° C. for 15 minutes. 6-Keto-PGF1α, a stable metabolite of PGI2, in the supernatant is quantitated after adequate dilution by using a radioimmunoassay kit (Amersham) according to the manufacturer's procedure.

In Vivo Assays

Carrageenan Induced Foot Edema in Rats

Male Sprague-Dawley rats (5 weeks old, Charles River Japan) are fasted overnight. A line is drawn using a marker above the ankle on the right hind paw and the paw volume (V0) was measured by water displacement using a plethysmometer (Muromachi). Animals are given orally either vehicle (0.1% methyl cellulose or 5% Tween 80) or a test compound (2.5 ml per 100 grams body weight). One hour later, the animals are then injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) is measured and the increase in volume (V3-V0) calculated. Since maximum inhibition attainable with classical NSAIDs is 60–70%, ED30 values are calculated.

Gastric Ulceration in Rats

The gastric ulcerogenicity of test compound is assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, are given orally either vehicle (0.1% methyl cellulose or 5% Tween 80) or a test compound (1 ml per 100 grams body weight). Six hours after, the animals are sacrificed by cervical dislocation. The stomachs are removed and inflated with 1% formalin solution (10 ml). Stomachs are opened by cutting along the greater curvature. From the number of rats that showed at least one gastric ulcer or haemorrhaging erosion (including ecchymosis), the incidence of ulceration is calculated. Animals do not have access to either food or water during the experiment.

Data Analysis

Statistical program packages, SYSTAT (SYSTAT, INC.) and StatView (Abacus Cencepts, Inc.) for Macintosh is used. Differences between test compound treated group and control group are tested for using ANOVA. The IC50 (ED30) values are calculated from the equation for the log-linear regression line of concentration (dose) versus percent inhibition.

COX-2 selectivity can be determined by ratio in terms of $IC_{50}$ value of COX-1 inhibition to COX-2 inhibition. In general, it can be said that a compound showing a COX-1/COX-2 inhibition ratio of more than 2 has good COX-2 selectivity.

What is claimed is:

1. A pharmaceutical composition for the treatment of migraine comprising a $5HT_1$ receptor agonist or a pharmaceutically acceptable salt thereof, and caffeine, with (a) a cyclooxygenase-2 inhibitor of the formula:

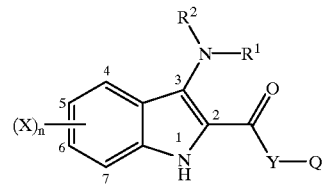

(I)

or the pharmaceutically acceptable salts thereof wherein
$R^1$ is hydrogen or $C_{1-4}$ alkyl; $R^2$ is C(=L')$R^3$ or $SO_2R^4$; Y is a direct bond or $C_{1-4}$ alkylene; L and L' are independently oxygen or sulfur;

Q is selected from the following:
(Q-a) $C_{1-6}$ alkyl,
(Q-b) halo-substituted $C_{1-4}$ alkyl,
(Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo,
(Q-d) phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy, nitro, halo-substituted $C_{1-4}$ alkoxy, $S(O)_mR^5$, $SO_2NH_2$, $SO_2N(C_{1-4}$ alkyl)$_2$, amino, $C_{1-4}$ alkylamino, di-($C_{1-4}$ alkyl)amino, $NR^1C(O)R^5$, CN, $C_{1-4}$ alkyl-OH and $C_{1-4}$ alkyl-$OR^5$,
(Q-e) a 5-membered monocyclic aromatic group containing one heteroatom selected from O, S and N and optionally containing one, two or three nitrogen atom(s) in addition to said heteroatom, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$, and
(Q-f) a 6-membered monocyclic aromatic group containing one nitrogen atom and optionally containing one, two or three additional nitrogen atom(s), and said monocyclic aromatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$;

$R^3$ is $-OR^6$, $-NR^7R^8$, $N(OR^1)R^7$ or a group of formula:

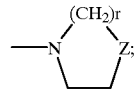

Z is a direct bond, oxygen, sulfur or $NR^5$;
$R^4$ is $C_{1-6}$ alkyl, halo-substituted $C_{1-4}$ alkyl, $C_{1-4}$ alkyl-OH, $-NR^7R^8$, phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy and halo-substituted $C_{1-4}$ alkoxy;

$R^5$ is $C_{1-4}$ alkyl or halo-substituted $C_{1-4}$ alkyl;

$R^6$ is $C_{1-4}$ alkyl, $C_{3-7}$ cycloalkyl, $C_{1-4}$ alkyl-$C_{3-7}$ cycloalkyl, halo-substituted $C_{1-4}$ alkyl, $C_{1-4}$ alkyl-phenyl or phenyl, the phenyl moiety being optionally substituted with one, or two substituents independently selected from halo, $C_{1-4}$ alkyl, halo-substituted $C_{1-4}$ alkyl, hydroxy, $C_{1-4}$ alkoxy, $C_{1-4}$ alkylthio, amino, di-($C_{1-4}$ alkyl)amino and nitro;

$R^7$ and $R^8$ are independently selected from the following:

(a) hydrogen, (b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl) amino, (c) $C_{3-7}$ cycloalkyl optionally substituted with a substituent independently selected from hydroxy, $C_{1-4}$ alkyl and $C_{1-4}$ alkoxy, (d) $C_{1-4}$ alkyl-$C_{3-7}$ cycloalkyl optionally substituted with a substituent independently selected from hydroxy, $C_{1-4}$ alkyl and $C_{1-4}$ alkoxy, and (e) $C_{1-4}$ alkyl-phenyl or phenyl, the phenyl moiety being optionally substituted with one or two substituents independently selected from halo, $C_{1-4}$ alkyl, halo-substituted $C_{1-4}$ alkyl, hydroxy, $C_{1-4}$ alkoxy, $C_{1-4}$ alkylthio, nitro, amino, di-($C_{1-4}$ alkyl) amino and CN;

X is independently selected from halo, $C_{1-4}$ alkyl, halo-substituted $C_{1-4}$ alkyl, hydroxy, $C_{1-4}$ alkoxy, halo-substituted C1-4 alkoxy, $C_{1-4}$ alkylthio, nitro, amino, di-($C_{1-4}$ alkyl)amino and CN;

m is 0, 1 or 2; n is 0, 1, 2 or 3; and r is 1, 2 or 3; or (b) a cyclooxygenase-2 inhibitor of the formula:

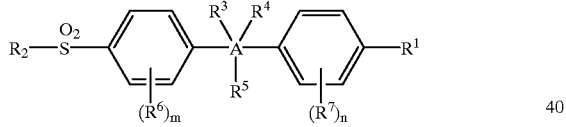

(XX)

or its pharmaceutically acceptable salt thereof, wherein the variables of formula XX are defined as follows;

A is partially unsaturated or unsaturated five membered heterocyclic, or partially unsaturated or unsaturated five membered carbocyclic, wherein the 4-(sulfonyl) phenyl and the 4-substituted phenyl in the formula (I) are attached to ring atoms of Ring A adjacent to each other;

$R^1$ is aryl or heteroaryl, and the aryl or heteroaryl being optionally substituted by one to four substituents selected from halo, $C_{1-4}$ alkyl, halo-substituted $C_{1-4}$ alkyl, $C_{1-4}$ alkoxy, $C_{1-4}$ alkyl carbonyl, hydroxy, nitro, cyano and amino, with the proviso that when A is pyrazole, $R^1$ is heteroaryl;

$R^2$ is $C_{1-4}$ alkyl, halo-substituted $C_{1-4}$ alkyl, $C_{1-4}$ alkylamino, $C_{1-4}$ dialkylamino or amino;

$R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, nitro, cyano $C_{1-4}$ alkyl, carboxy, $C_{1-4}$ alkoxycarbonyl, aminocarbonyl, N-$C_{1-4}$ alkylaminocarbonyl, N,N-di-$C_{1-4}$ alkylaminocarbonyl, N-arylaminocarbonyl, N,N-diarylaminocarbonyl, N-$C_{1-4}$ alkyl-N-arylaminocarbonyl, aryl, aryloxy, aryloxy-$C_{1-4}$ alkyl, heteroaryl, heteroaryloxy, heteroaryloxy-$C_{1-4}$ alkyl, morpholino-carbonyl, $C_{1-4}$ alkoxyaminocarbonyl or $C_{1-4}$ alkyl-carbonylamino; or two of $R^3$, $R^4$ and $R^5$ are taken together with atoms to which they are attached and form a 4–7 membered ring;

$R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamino, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{14}$ alkyl, hydroxy, amino-$C_{1-4}$ alkyl and N,N-di $C_{1-4}$ alkylamino-$C_{1-4}$ alkyl; and m and n are independently 1, 2, 3 or 4, with the proviso that when A contains an oxygen or sulfur heteroatom, one of $R^3$, $R^4$ or $R^5$ is absent; or (c) a cyclooxygenase-2 inhibitor of the formula:

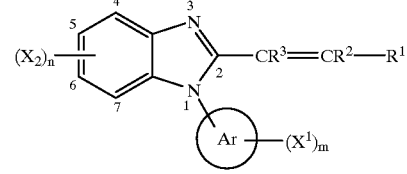

(XXX)

or a pharmaceutically acceptable salt thereof, wherein variables of formula XXX are defined as follows;

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N-[($C_1$–$C_4$ alkyl)sulfonyl] amino, N-[(halo-substituted $C_1$–$C_4$ alkyl)sulfonyl] amino, $C_1$–$C_4$ alkanoyl, carboxy, ($C_1$–$C_4$ alkoxy) carbonyl, carbamoyl, [N—($C_1$–$C_4$ alkyl)amino] carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$X^2$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N—[($C_1$–$C_4$ alkyl) sulfonyl]amino, N-[(halo-substituted $C_1$–$C_4$ alkyl) sulfonyl]amino, $C_1$–$C_4$ alkanoyl, carboxy, ($C_1$–$C_4$ alkoxy)carbonyl, carbamoyl, [N—($C_1$–$C_4$ alkyl) amino]carbonyl, [N,N-di($C_1$–$C_4$ alkyl)amino]

carbonyl, N-carbamoylamino, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$R^1$ is selected from hydrogen;

straight or branched $C_1$–$C_4$ alkyl optionally substituted with one to three substituent(s) wherein said substituents are independently selected from halo, hydroxy, $C_1$–$C_4$ alkoxy, amino, N—($C_1$–$C_4$ alkyl)amino and N,N-di($C_1$–$C_4$ alkyl)amino;

$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

phenyl optionally substituted with one to three substituent(s) wherein said substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—[($C_1$–$C_4$ alkyl)($C_1$–$C_4$ alkanoyl)]amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl; and heteroaryl selected from a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl being optionally substituted with one to three substituent(s) selected from $X^1$;

$R^2$ and $R^3$ are independently selected from:

hydrogen;

halo;

$C_1$–$C_4$ alkyl;

phenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

or $R^1$ and $R^2$ can form, together with the carbon atom to which they are attached, a $C_3$–$C_7$ cycloalkyl ring;

m is 0, 1, 2, 3, 4 or 5; and n is 0, 1, 2, 3 or 4; or (d) a cyclooxygenase-2 inhibitor of the formula:

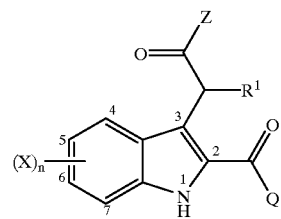

(XL)

or the pharmaceutically acceptable salts thereof wherein the variables of formula XL are as defined as follows;

Z is OH, C1–6 alkoxy, —$NR^2R^3$ or a group of the formula (II) or (III):

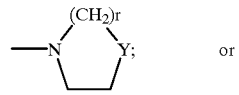

(II)

or

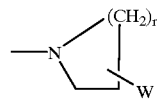

(III)

wherein r is 1, 2, 3 or 4, Y is a direct bond, O, S or NR4, and W is OH or —$NR^2R^3$;

Q is selected from the following:

(a) phenyl optionally substituted with one, two or three substituents independently selected from (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—(CH2)n-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fused heterocycle optionally substituted with one, two or three substituents independently selected from the group (a-1);

R1 is hydrogen, $C_{1-4}$ alkyl or halo;

R2 and R3 are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

R4 is hydrogen or $C_{1-4}$ alkyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4; or (e) a cyclooxygenase-2 inhibitor of the formula:

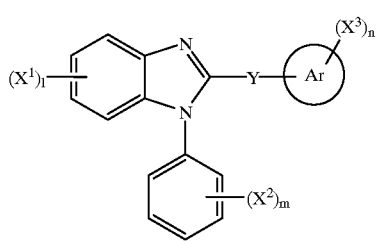

(L)

and the pharmaceutically acceptable salts thereof wherein the compounds of formula L are defined as follows;

Ar is phenyl, $C_{3-8}$ cycloalkyl, $C_{4-8}$ cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

X1 is H, halo, $C_{1-4}$ alkyl, hydroxy, $C_{1-4}$ alkoxy, halo-substituted $C_{1-4}$ alkyl, hydroxy-substituted $C_{1-4}$ alkyl, ($C_{1-4}$)alkoxy($C_{1-4}$)alkyl, amino, $C_{1-4}$ alkylamino, di($C_{1-4}$)alkylamino, amino $C_{1-4}$ alkyl, ($C_{1-4}$)alkylamino($C_{1-4}$)alkyl, di($C_{1-4}$)alkylamino($C_{1-4}$)alkyl, $C_{1-4}$ alkanoylamino, di($C_{1-4}$)alkanoylamino, ($C_{1-4}$)alkyl($C_{1-4}$ alkanoyl)amino, $C_{1-4}$ alkylsulfonylamino, $C_{1-4}$ alkanoyl, carboxyl, ($C_{1-4}$) alkoxycarbonyl, aminocarbonyl, ($C_{1-4}$) alkylaminocarbonyl, di($C_{1-4}$)alkylaminocarbonyl, cyano, nitro, mercapto, $C_{1-4}$ alkylthio, $C_{1-4}$ alkylsulfinyl, $C_{1-4}$ alkylsulfonyl, aminosulfonyl, $C_{1-4}$ alkylaminosulfonyl or di($C_{1-4}$) alkylaminosulfonyl;

X2 and X3 are independently $C_{1-4}$ alkyl, halo, halo-substituted $C_{1-4}$ alkyl, hydroxy, $C_{1-4}$ alkoxy, mercapto, $C_{1-4}$ alkylthio, $C_{1-4}$ alkylsulfinyl, $C_{1-4}$ alkylsulfonyl, $C_{1-4}$ alkanoyl, carboxyl, ($C_{1-4}$)alkoxycarbonyl, aminocarbonyl, $C_{1-4}$ alkylaminocarbonyl, di($C_{1-4}$) alkylaminocarbonyl, cyano, nitro, amino, $C_{1-4}$ alkylamino, di($C_{1-4}$)alkylamino or $C_{1-4}$ alkylsulfonylamino;

Y is —CR1=CR2— or —C≡C—, wherein $R^1$ and $R^2$ are independently H, methyl, ethyl or halo;

l is 0, 1, 2, 3 or 4; and m and n are independently 0, 1, 2 or 3, with the proviso that when Ar is phenyl; and l, m and n are 0, Y is not —CH=CH—; and when Ar is phenyl; l and m are 0; n is 1; and Y is —CH=CH—, X3 is not $C_{1-4}$ alkoxy attached to the 2-position of Ar, nor amino, $C_{1-4}$ alkylamino or di($C_{1-4}$)alkylamino attached at the 4-position of Ar; or (f) a cyclooxygenase-2 inhibitor of the formula

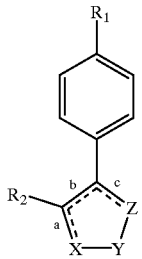

(LX)

or pharmaceutically acceptable salts thereof wherein:

X—Y—Z— is selected from the group consisting of —C(O)—O—CR5(R5)— when side b is a double bond, and sides a and c are single bonds; and R1 is selected from the group consisting of
(c) $S(O)_2CH_3$,
(d) $S(O)_2NH_2$, R2 is selected from the group consisting of
(e) $C_{1-6}$alkyl,
(f) $C_3$, $C_4$, $C_5$, $C_6$ and $C_7$, cycloalkyl,
(g) Heteroaryl
(h) Benzoheteroaryl
(e) Mono- or di-substituted phenyl wherein the substituent is selected from the group consisting of
(14) hydrogen,
(15) halo,
(16) $C_{1-6}$alkoxy,
(17) $C_{1-6}$alkylthio,
(18) CN,
(19) $CF_3$,
(20) $C_{1-6}$alkyl,
(21) $N_3$,
(22) —$CO_2H$,
(23) —$CO_2$—$C_{1-4}$alkyl,
(24) —C(R5)(R6)—OH,
(25) —C(R5)(R6)—O—$C_{1-4}$alkyl, and
(26) —$C_{1-6}$alkyl-$CO_2$R5;

R5, R5 and R6 are each independently selected from the group consisting of
(c) hydrogen,
(d) $C_{1-6}$)alkyl,
or R5 and R6 together with the carbon to which they are attached from a saturated monocyclic carbon ring is 3, 4, 5, 6 or 7 atoms;

and a pharmaceutically acceptable carrier.

2. A pharmaceutical composition according to claim 1, wherein the 5HT$_1$ receptor agonist is selected from eletriptan, rizatriptan, zolmitriptan, sumatriptan and naratriptan.

3. A pharmaceutical composition according to claim 1, wherein the cyclooxygenase-2 inhibitor is Vioxx.

4. A pharmaceutical composition according to claim 1, wherein the cyclooxygenase-2 inhibitor is selected from the group consisting of:
ethyl (2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl [6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
[6-chloro-2-(3,4-dichlorobenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-yl)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl)acetic acid;
[6-chloro-2-(5-methylpyridine-2-carbonyl)-1H-indol-3-yl]acetic acid;
methyl [6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl [5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(1-methylimidazole-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl (2-benzoyl-6-chloro-1H-indol-3-yl)acetate;
(2-benzoyl-6-chloro-1H-indol-3-yl)-N,N-dimethylacetamide;
(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-methylacetamide;
2-(2-benzoyl-6-chloro-1H-indol-3-yl)-1-piperidino-1-ethanone;
2-(2-benzoyl-6-chloro-1H-indol-3-yl)-1-(4-methyl-1-piperazinyl)-1-ethanone;
(2-benzoyl-6-chloro-1H-indol-3-yl)-N-(2-cyanoethyl)acetamide;
(2-benzoyl-6-chloro-1H-indol-3-yl)-N-(2-hydroxyethyl)acetamide;
2-(2-benzoyl-6-chloro-1H-indol-3-yl)-1-morpholino-1-ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic acid;
methyl [6-chloro-2-(4-methoxybenzoyl)-1H-indol-3-yl]acetate;
[6-chloro-2-(4-methoxybenzoyl)-1H-indol-3-yl]acetic acid;
methyl [6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
methyl [5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl [6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl [5-chloro-2-(4-isopropylpyridine-2-carbonyl)-1H-indol-3-yl]acetate;
[5-chloro-2-(4-isopropylpyridine-2-carbonyl)-1H-indol-3-yl]acetic acid;
methyl [6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl [5-chloro-2-(4-propylpyridine-2-carbonyl)-1H-indol-3-yl]acetate;
[5-chloro-2-(4-propylpyridine-2-carbonyl)-1H-indol-3-yl]acetic acid;
methyl [2-(4-tert-butylpyridine-2-carbonyl)-6-chloro-1H-indol-3-yl]acetate;
[2-(4-tert-butylpyridine-2-carbonyl)-6-chloro-1H-indol-3-yl)]acetic acid;
methyl [-(4-tert-butylpyridine-2-carbonyl)-5-chloro-1H-indol-3-yl]acetate;
[2-(4-tert-butylpyridine-2-carbonyl)-5-chloro-1H-indol-3-yl]acetic acid;
methyl [6-chloro-2-(3-methylpyridine-2-carbonyl)-1H-indol-3-yl]acetate;
[6-chloro-2-(3-methylpyridine-2-carbonyl)-1H-indol-3-yl]acetic acid;
methyl [5-chloro-2-(3-methylpyridine-2-carbonyl)-1H-indol-3-yl]acetate;
[5-chloro-2-(3-methylpyridine-2-carbonyl)-1H-indol-3-yl]acetic acid;
methyl [6-chloro-2-(6-methylpyridine-2-carbonyl)-1H-indol-3-yl]acetate;
[6-chloro-2-(6-methylpyridine-2-carbonyl)-1H-indol-3-yl]acetic acid;

methyl [5-chloro-2-(5-methylpyridine-2-carbonyl)-1H-indol-3-yl]acetate;
[5-chloro-2-(5-methylpyridine-2-carbonyl)-1H-indol-3-yl]acetic acid;
methyl [6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl [5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl [5-chloro-2-(5-chloropyridine-2-carbonyl)-1H-indol-3-yl]acetate;
[5-chloro-2-(5-chloropyridine-2-carbonyl)-1H-indol-3-yl]acetic acid;
methyl [6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl [5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl [6-chloro-2-(pyridine-3-carbonyl)-1H-indol-3-yl]acetate;
[6-chloro-2-(pyridine-3-carbonyl)-1H-indol-3-yl]acetic acid;
methyl [6-chloro-2-(pyridine-4-carbonyl)-1H-indol-3-yl]acetate;
[6-chloro-2-(pyridine-4-carbonyl)-1H-indol-3-yl]acetic acid;
methyl [6-chloro-2-[4-(hydroxymethyl)pyridine-2-carbonyl]-1H-indol-3-yl]acetate;
[6-chloro-2-[4-(hydroxymethyl)pyridine-2-carbonyl]-1H-indol-3-yl]acetic acid;
methyl [5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl [5-chloro-2-(3,4-dimethylpyridine-2-carbonyl)-1H-indol-3-yl]acetate;
[5-chloro-2-(3,4-dimethylpyridine-2-carbonyl)-1H-indol-3-yl]acetic acid;
methyl [5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl [6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;
methyl [6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl [5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl [6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl [5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl [6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;
methyl [6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl [5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl [5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;
methyl [6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl [5,6-dichloro-2-(4-methylpyridine-2-carbonyl)-1H-indol3-yl]acetate;
[5,6-dichloro-2-(4-methylpyridine-2-carbonyl)-1H-indol-3-yl]acetic acid;
methyl [5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl [5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl [5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl [6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl [5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl [5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl [6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl [5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl [2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl [5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl [2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;

methyl [2-(4-methylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl [6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl [2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl [2-(4-methylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl (2-benzoyl-1H-indol-3-yl)acetate;
(2-benzoyl-1H-indol-3-yl)acetic acid;
methyl [2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl [6-methoxy-2-(4-chlorobenzoyl)-1H-indol-3-yl]acetate;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
methyl [2-(4-chlorobenzoyl)-5-ethyl-1H-indol-3-yl]acetate;
[2-(4-chlorobenzoyl)-5-ethyl-1H-indol-3-yl]acetic acid;
methyl [2-(4-chlorobenzoyl)-5-methoxy-1H-indol-3-yl]acetate;
[2-(4-chlorobenzoyl)-5-methoxy-1H-indol-3-yl]acetic acid;
methyl [2-(4-chlorobenzoyl)-5-isopropyl-1H-indol-3-yl]acetate;
[2-(4-chlorobenzoyl)-5-isopropyl-1H-indol-3-yl]acetic acid;
methyl [2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl [2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl [6-chloro-2-(2-methoxybenzoyl)-1H-indol-3-yl]acetate;
[6-chloro-2-(2-methoxybenzoyl)-1H-indol-3-yl]acetic acid;
methyl [6-chloro-2-(3-methoxybenzoyl)-1H-indol-3-yl]acetate;
[6-chloro-2-(3-methoxybenzoyl)-1H-indol-3-yl]acetic acid;
methyl [6-chloro-2-(3-benzyloxybenzoyl)-1H-indol-3-yl]acetate;
[6-chloro-2-(3-benzyloxybenzoyl)-1H-indol-3-yl]acetic acid;
methyl [6-chloro-2-(3-hydroxybenzoyl)-1H-indol-3-yl]acetate;
[6-chloro-2-(3-hydroxybenzoyl)-1H-indol-3-yl]acetic acid;
methyl [6-chloro-2-(4-benzoxybenzyloyl)-1H-indol-3-yl]acetate;
[6-chloro-2-(4-benzyloxybenzoyl)-1H-indol-3-yl]acetic acid;
methyl [6-chloro-2-(4-hydroxybenzoyl)-1H-indol-3-yl]acetate;
[6-chloro-2-(4-hydroxybenzoyl)-1H-indol-3-yl]acetic acid;
methyl [6-chloro-2-(4-isopropoxybenzoyl)-1H-indol-3-yl]acetate;
[6-chloro-2-(4-isopropoxybenzoyl)-1H-indol-3-yl]acetic acid;
methyl [6-chloro-2-(4-phenylbenzoyl)-1H-indol-3-yl]acetate;
[6-chloro-2-(4-phenylbenzoyl)-1H-indol-3-yl]acetic acid;
methyl [6-chloro-2-(4-trifluoromethoxybenzoyl)-1H-indol-3-yl]acetate;
[6-chloro-2-(4-trifluoromethoxybenzoyl)-1H-indol-3-yl]acetic acid;
methyl [5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl [5-chloro-2-(4-methoxybenzoyl)-1H-indol-3-yl]acetate;
[5-chloro-2-(4-methoxybenzoyl)-1H-indol-3-yl]acetic acid;
methyl [6-chloro-2-(4-nitrobenzoyl)-1H-indol-3-yl]acetate;
[6-chloro-2-(4-nitrobenzoyl)-1H-indol-3-yl]acetic acid;
methyl [6-chloro-2-[(4-methylsulfonyl)benzoyl]-1H-indol-3-yl]acetate;
[6-chloro-2-[(4-methylsulfonyl)benzoyl]-1H-indol-3-yl]acetic acid;
methyl [6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl [6-chloro-2-(4-chloro-3-fluorobenzoyl)-1H-indol-3-yl]acetate;
[6-chloro-2-(4-chloro-3-fluorobenzoyl)-1H-indol-3-yl]acetic acid;
methyl [6-chloro-2-(4-cyanobenzoyl)-1H-indol-3-yl]acetate;
methyl [6-chloro-2-[4-bromobenzoyl]-1H-indol-3-yl]acetate;
methyl [6-chloro-2-[4-(2-thienyl)benzoyl]-1H-indol-3-yl]acetate;
[6-chloro-2-[4-(2-thienyl)benzoyl]-1H-indol-3-yl]acetic acid;
methyl [6-chloro-2-[4-(2-furyl)benzoyl]-1H-indol-3-yl]acetate;
[6-chloro-2-[4-(2-furyl)benzoyl]-1H-indol-3-yl]acetic acid;
methyl [6-chloro-2-[4-(3-pyridyl)benzoyl]-1H-indol-3-yl]acetate;
[6-chloro-2-[4-(3-pyridyl)benzoyl]-1H-indol-3-yl]acetic acid;
methyl [6-chloro-2-[4-(2-thiazolyl)benzoyl]-1H-indol-3-yl]acetate;
[6-chloro-2-[4-(2-thiazolyl)benzoyl]-1H-indol-3-yl]acetic acid;
methyl [6-chloro-2-(3-bromobenzoyl)-1H-indol-3-yl]acetate;
methyl [6-chloro-2-[3-(2-furyl)benzoyl]-1H-indol-3-yl]acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl]propionate;
dl-2-[2-(4-chlorobenzoyl)-6-chloro-1H-indol-3-yl]propionic acid;
methyl [5-chloro-2-(isoquinoline-3-carbonyl)-1H-indol-3-yl]acetate;
[5-chloro-2-(isoquinoline-3-carbonyl)-1H-indol-3-yl]acetic acid;
methyl [6-chloro-2-(isoquinoline-3-carbonyl)-1H-indol-3-yl]acetate;
[6-chloro-2-(isoquinoline-3-carbonyl)-1H-indol-3-yl]acetic acid;

methyl [5-chloro-2-(5-methylisoxazole-3-carbonyl)-1H-indol-3-yl]acetate;
[5-chloro-2-(5-methylisoxazole-3-carbonyl)-1H-indol-3-yl]acetic acid;
methyl [6-chloro-2-(5-methylisoxazole-3-carbonyl)-1H-indol-3-yl]acetate;
[6-chloro-2-(5-methylisoxazole-3-carbonyl)-1H-indol-3-yl]acetic acid;
methyl [5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl [6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl [5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl [6-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-(2-thienyl)carbonylindol-3-yl]acetic acid;
methyl [6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl [6-chloro-2-[3-methoxymethyl-2-furoyl]-1H-indol-3-yl]acetate;
[6-chloro-2-[3-methoxymethyl-2-furoyl]-1H-indol-3-yl]acetic acid;
[6-chloro-2-(1-methylimidazole-2-carbonyl)-1H-indol-3-yl]acetic acid;
methyl [6-chloro-2-(1-methylimidazole-2-carbonyl)-1H-indol-3-yl]acetate;
methyl [5-chloro-2-(methylimidazole-2-carbonyl)-1H-indol-3-yl]acetate;
[5-chloro-2(1-methylimidazole-2-carbonyl)-1H-indol-3-yl]acetic acid;
methyl [5-chloro-2-(imidazole-2-carbonyl)-1H-indol-3-yl]acetate;
[5-chloro-2-(imidazole-2-carbonyl)-1H-indol-3-yl]acetic acid;
methyl [6-chloro-2-(imidazole-2-carbonyl)-1H-indol-3-yl]acetate;
[6-cloro-2-(imidazole-2-carbonyl)-1H-indol-3-yl]acetic acid;
methyl [5-chloro-2-(4-methylthiazole-2-carbonyl)1H-indol-3-yl]acetate;
[5-chloro-2-(4-methylthiazole-2-carbonyl)-1H-indol-3-yl]acetic acid;
methyl [5-chloro-2-(1-methylpyrrole-2-carbonyl)-1H-indol-3-yl]acetate;
[5-chloro-2-(1-methylpyrrole-2-carbonyl)-1H-indol-3-yl]acetic acid;
methyl [5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl [5-chloro-2-(thiazole-5-carbonyl)-1H-indol-3-yl]acetate;
[5-chloro-2-(thiazole-5-carbonyl)-1H-indol-3-yl]acetic acid;
methyl [6-chloro-2-(4-methylthiazole-2-carbonyl)-1H-indol-3-yl]acetate;
[6-chloro-2-(4-methylthiazole-2-carbonyl)-1H-indol-3-yl]acetic acid;
methyl [5-chloro-2-[3-(ethoxycaronyl)isoxazole-5-carbonyl)-1H-indol-3-yl]acetate;
[5-chloro-2-[3-(carboxy)isoxazole-5-carbonyl)-1H-indol-3-yl]acetic acid;
methyl [6-chloro-2-cyclopropanecarbonyl-1H-indol-3-yl]acetate;
[6-chloro-2-cyclopropanecarbonyl-1H-indol-3-yl]acetic acid;
methyl [6-chloro-2-cyclobutanecarbonyl-1H-indol-3-yl]acetate;
[6-chloro-2-cyclobutanecarbonyl-1H-indol-3-yl]acetic acid;
methyl [5-(tert-butyl)-2-(4-chlorobenzoyl)-1H-indol-3-yl]acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanone;
[5-chloro-2-(4-methylpyridine-2-carbonyl)1H-indol-3-yl]-N-(2aminoethyl)acetamide;
2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl]acetic acid;
methyl [6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;
methyl [6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl [5-acetyl-2-(4-chlorobenzoyl)-1H-indol-3-yl]acetate;
[5-acetyl-2-(4-chlorobenzoyl)-1H-indol-3-yl]acetic acid;
methyl [6-chloro-2-(4-chlorobenzoyl)-5-fluoro-1H-indol-3-yl]acetate;
methyl [6-fluoro-2-(4-methylpridine-2-carbonyl]-1H-indol-3-yl]acetate;
[6-fluoro-2-(4-methylpridine-2-carbonyl)-1H-indol-3-yl]acetic acid;
methyl [6-fluoro-2-(4-chlorobenzoyl)-1H-indol-3-yl]acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
[2-(4-methylpyridine-2-carbonyl)-5-methylthio-1H-indol-3-yl]acetic acid, and a salt thereof.

5. A method of treating migraine in a mammal, comprising administering to said mammal an antimigraine effective amount of a pharmaceutical composition according to claim 1.

6. A method of treating migraine in a mammal, comprising administering to said mammal a 5HT$_1$ receptor agonist or a pharmaceutically acceptable salt thereof, and caffeine, with (a) a compound of the formula:

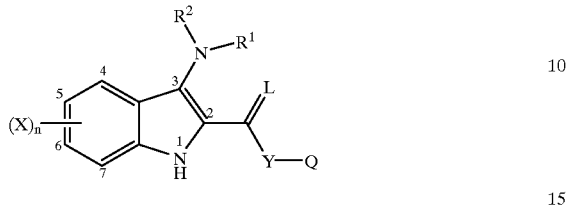

(I)

or the pharmaceutically acceptable salts thereof wherein
$R^1$ is hydrogen or $C_{1-4}$ alkyl; $R^2$ is $C(=L')R^3$ or $SO_2R^4$; Y is a direct bond or $C_{1-4}$ alkylene; L and L' are independently oxygen or sulfur;
Q is selected from the following:
(Q-a) $C_{1-6}$ alkyl,
(Q-b) halo-substituted $C_{1-4}$ alkyl,
(Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo,
(Q-d) phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy, nitro, halo-substituted $C_{1-4}$ alkoxy, $S(O)_mR^5$, $SO_2NH_2$, $SO_2N(C_{1-4}$ alkyl$)_2$, amino, $C_{1-4}$ alkylamino, di-($C_{1-4}$ alkyl)amino, $NR^1C(O)R^5$, CN, $C_{1-4}$ alkyl-OH and $C_{1-4}$ alkyl-$OR^5$,
(Q-e) a 5-membered monocyclic aromatic group containing one heteroatom selected from O, S and N and optionally containing one, two or three nitrogen atom(s) in addition to said heteroatom, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$, and
(Q-f) a 6-membered monocyclic aromatic group containing one nitrogen atom and optionally containing one, two or three additional nitrogen atom(s), and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$;
$R^3$ is $-OR^6$, $-NR^7R^8$, $N(OR^1)R^7$ or a group of formula:

Z is a direct bond, oxygen, sulfur or $NR^5$;
$R^4$ is $C_{1-6}$ alkyl, halo-substituted $C_{1-4}$ alkyl, $C_{1-4}$ alkyl-OH, $-NR^7R^8$, phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy and halo-substituted $C_{1-4}$ alkoxy;
$R^5$ is $C_{1-4}$ alkyl or halo-substituted $C_{1-4}$ alkyl;
$R^6$ is $C_{1-4}$ alkyl, $C_{3-7}$ cycloalkyl, $C_{1-4}$ alkyl-$C_{3-7}$ cycloalkyl, halo-substituted $C_{1-4}$ alkyl, $C_{1-4}$ alkyl-phenyl or phenyl, the phenyl moiety being optionally substituted with one, or two substituents independently selected from halo, $C_{1-4}$ alkyl, halo-substituted $C_{1-4}$ alkyl, hydroxy, $C_{1-4}$ alkoxy, $C_{1-4}$ alkylthio, amino, di-($C_{1-4}$ alkyl)amino and nitro;
$R^7$ and $R^8$ are independently selected from the following:
(a) hydrogen,
(b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl) amino,
(c) $C_{3-7}$ cycloalkyl optionally substituted with a substituent independently selected from hydroxy, $C_{1-4}$ alkyl and $C_{1-4}$ alkoxy,
(d) $C_{1-4}$ alkyl-$C_{3-7}$ cycloalkyl optionally substituted with a substituent independently selected from hydroxy, $C_{1-4}$ alkyl and $C_{1-4}$ alkoxy, and
(f) $C_{1-4}$ alkyl-phenyl or phenyl, the phenyl moiety being optionally substituted with one or two substituents independently selected from halo, $C_{1-4}$ alkyl, halo-substituted $C_{1-4}$ alkyl, hydroxy, $C_{1-4}$ alkoxy, $C_{1-4}$ alkylthio, nitro, amino, di-($C_{1-4}$ alkyl) amino and CN;
X is independently selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, di-($C_{1-4}$ alkyl)amino and CN;
m is 0, 1 or 2; n is 0, 1, 2or 3; and r is 1,2 or 3; or (b) a compound of the formula:

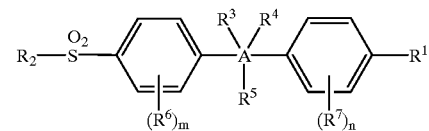

(XX)

or its pharmaceutically acceptable salt thereof, wherein the variables of formula XX are defined as follows;
A is partially unsaturated or unsaturated five membered heterocyclic, or partially unsaturated or unsaturated five membered carbocyclic, wherein the 4-(sulfonyl) phenyl and the 4-substituted phenyl in the formula (I) are attached to ring atoms of Ring A adjacent to each other;
$R^1$ is aryl or heteroaryl, and the aryl or heteroaryl being optionally substituted by one to four substituents selected from halo, $C_{1-4}$ alkyl, halo-substituted $C_{1-4}$ alkyl, $C_{1-4}$ alkoxy, $C_{1-4}$ alkyl carbonyl, hydroxy, nitro, cyano and amino, with the proviso that when A is pyrazole, $R^1$ is heteroaryl;
$R^2$ is $C_{1-4}$ alkyl, halo-substituted $C_{1-4}$ alkyl, $C_{1-4}$ alkylamino, $C_{1-4}$ dialkylamino or amino;
$R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxy, $C_{1-4}$ alkoxycarbonyl, aminocarbonyl, N—$C_{1-4}$ alkylaminocarbonyl, N,N-di-$C_{1-4}$ alkylaminocarbonyl, N-arylaminocarbonyl, N,N-diarylaminocarbonyl, N—$C_{1-4}$ alkyl-N-arylamiocarbonyl, aryl, aryloxy, aryloxy-$C_{1-4}$ alkyl, heteroaryl, heteroaryloxy, heteroaryloxy-$C_{1-4}$ alkyl, morpholino-carbonyl, $C_{1-4}$ alkoxyaminocarbonyl or $C_{1-4}$ alkyl-carbonylamino; or two of $R^3$, $R^4$ and $R^5$ are taken together with atoms to which they are attached and form a 4–7 membered ring;

$R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamino, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl, hydroxy, amino-$C_{1-4}$ alkyl and N,N-di $C_{1-4}$ alkylamino-$C_{1-4}$ alkyl; and m and n are independently 1, 2, 3 or 4, with the proviso that when A contains an oxygen or sulfur heteroatom, one of $R^3$, $R^4$ or $R^5$ is absent; or (c) a compound of the formula:

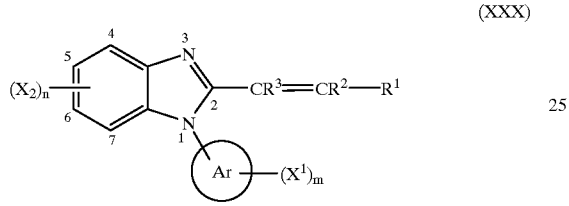

(XXX)

or a pharmaceutically acceptable salt thereof, wherein variables of formula XXX are defined as follows;

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N—[($C_{1-4}$ alkyl)sulfonyl]amino, N—[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$X^2$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N—[($C_1$–$C_4$ alkyl) sulfonyl]amino, N-[(halo-substituted $C_{1-4}$ alkyl) sulfonyl]amino, $C_1$–$C_4$ alkanoyl, carboxy, ($C_1$–$C_4$ alkoxy)carbonyl, carbamoyl, [N—($C_1$–$C_4$ alkyl) amino]carbonyl, [N,N-di($C_1$–$C_4$ alkyl)amino] carbonyl, N-carbamoylamino, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl) amino]sulfonyl;

$R^1$ is selected from hydrogen;

straight or branched $C_1$–$C_4$ alkyl optionally substituted with one to three substituent(s) wherein said substituents are independently selected from halo, hydroxy, $C_1$–$C_4$ alkoxy, amino, N—($C_1$–$C_4$ alkyl)amino and N,N-di($C_1$–$C_4$ alkyl)amino;

$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl) amino and N,N-di($C_1$–$C_4$ alkyl)amino;

$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl) amino and N,N-di($C_1$–$C_4$ alkyl)amino;

phenyl optionally substituted with one to three substituent(s) wherein said substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl) amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—[($C_1$–$C_4$ alkyl)($C_1$–$C_4$ alkanoyl)]amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, (N—($C_1$–$C_4$ alkyl)amino]sulfonyl and [N,N-di($C_1$–$C_4$ alkyl) amino]sulfonyl; and heteroaryl selected from a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl being optionally substituted with one to three substituent(s) selected from $X^1$;

$R^2$ and $R^3$ are independently selected from:

hydrogen;

halo;

$C_1$–$C_4$ alkyl;

phenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

or $R^1$ and $R^2$ can form, together with the carbon atom to which they are attached, a $C_3$–$C_7$ cycloalkyl ring;

m is 0, 1, 2, 3, 4 or 5; and n is 0, 1, 2, 3 or 4; or (d) a compound of the formula:

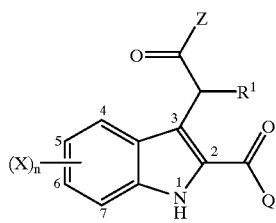

(XL)

or the pharmaceutically acceptable salts thereof wherein the variables of formula XL are as defined as follows;

Z is OH, C1–6 alkoxy, —NR²R³ or a group of the formula (II) or (III):

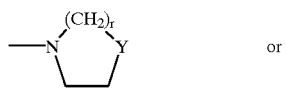

(II)

or

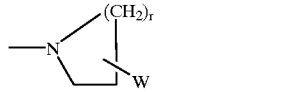

(III)

wherein r is 1, 2, 3 or 4, Y is a direct bond, O, S or NR4, and W is OH or —NR²R³;

Q is selected from the following:

(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
  (a-2) aryl or —O—(CH2)n-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

R1 is hydrogen, $C_{1-4}$ alkyl or halo;

R2 and R3 are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

$R_4$ is hydrogen or $C_{1-4}$ alkyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3, or 4; or (e) a compound of the formula:

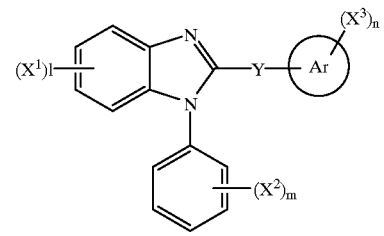

(L)

and the pharmaceutically acceptable salts thereof wherein the compounds of formula L are defined as follows;

Ar is phenyl, $C_{3-8}$ cycloalkyl, $C_{4-8}$ cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

X1 is H, halo, $C_{1-4}$ alkyl, hydroxy, $C_{1-4}$ alkoxy, halo-substituted $C_{1-4}$ alkyl, hydroxy-substituted $C_{1-4}$ alkyl, ($C_{1-4}$)alkoxy($C_{1-4}$)alkyl, amino, $C_{1-4}$ alkylamino, di($C_{1-4}$) alkylamino, amino $C_{1-4}$ alkyl, ($C_{1-4}$)alkylamino($C_{1-4}$)alkyl, di($C_{1-4}$)alkylamino($C_{1-4}$)alkyl, $C_{1-4}$ alkanoylamino, di($C_{1-4}$)alkanoylamino, ($C_{1-4}$)alkyl($C_{1-4}$alkanoyl)amino, $C_{1-4}$ alkylsulfonylamino, $C_{1-4}$ alkanoyl, carboxyl, ($C_{1-4}$) alkoxycarbonyl, aminocarbonyl, ($C_{1-4}$) alkylaminocarbonyl, di($C_{1-4}$)alkylaminocarbonyl, cyano, nitro, mercapto, $C_{1-4}$ alkylthio, $C_{1-4}$ alkylsulfinyl, $C_{1-4}$ alkylsulfonyl, aminosulfonyl, $C_{1-4}$ alkylaminosulfonyl or di($C_{1-4}$) alkylaminosulfonyl;

X2 and X3 are independently $C_{1-4}$ alkyl, halo, halo-substituted $C_{1-4}$ alkyl, hydroxy, $C_{1-4}$ alkoxy, mercapto, $C_{1-4}$ alkylthio, $C_{1-4}$ alkylsulfinyl, $C_{1-4}$ alkylsulfonyl, $C_{1-4}$ alkanoyl, carboxyl, ($C_{1-4}$) alkoxycarbonyl, aminocarbonyl, $C_{1-4}$ alkylaminocarbonyl, di($C_{1-4}$)alkylaminocarbonyl, cyano, nitro, amino, $C_{1-4}$ alkylamino, di($C_{1-4}$) alkylamino or $C_{1-4}$ alkylsulfonylamino;

Y is —CR1═CR2— or —C≡C—, wherein $R^1$ and $R^2$ are independently H, methyl, ethyl or halo;

I is 0, 1, 2, 3 or 4; and m and n are independently 0, 1, 2 or 3, with the proviso that when Ar is phenyl; and I, m and n are α, Y is not —CH═CH—; and when Ar is phenyl; I and m are α; n is 1; and Y is —CH═CH—, X3 is not $C_{1-4}$ alkoxy attached to the 2- position of Ar, nor amino, $C_{1-4}$ alkylamino or di($C_{1-4}$) alkylamino attached at the 4-position of Ar; or (f) a compound of the formula

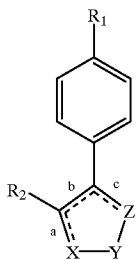

(LX)

or pharmaceutically acceptable salts thereof wherein:

X—Y—Z— is selected from the group consisting of —C(O)—O—CR$^5$(R$^5$)— when side b is a double bond, and sides a and c are single bonds; and $R^1$ is selected from the group consisting of
(g) S(O)$_2$CH$_3$,
(h) S(O)$_2$NH$_2$, $R^2$ is selected from the group consisting of
(m) $C_{1-6}$alkyl,
(n) $C_3$, $C_4$, $C_5$, $C_6$ and $C_7$, cycloalkyl,
(o) Heteroaryl
(p) Benzoheteroaryl
(e) Mono- or di-substituted phenyl wherein the substituent is selected from the group consisting of
(40) hydrogen,
(41) halo,
(42) $C_{1-6}$alkoxy,
(43) $C_{1-6}$alkylthio,
(44) CN,
(45) CF$_3$,
(46) $C_{1-6}$alkyl,
(47) N$_3$,
(48) —CO$_2$H,
(49) —CO$_2$—C$_{1-4}$alkyl,
(50) —C(R$^5$)(R$^6$)—OH,
(51) —C(R$^5$)(R$^6$)—O—C$_{1-4}$alkyl, and
(52) —C$_{1-6}$alkyl-CO$_2$R$^5$;

R$^5$, R$^5$ and R$^6$ are each independently selected from the group consisting of
(g) hydrogen,
(h) $C_{1-6}$)alkyl, or R$^5$ and R$^6$ together with the carbon to which they are attached from a saturated monocyclic carbon ring is 3, 4, 5, 6 or 7 atoms;

in amounts that render the combination of such three active agents effective in the treatment of migraine.

7. A method according to claim 5, wherein the 5HT$_1$ receptor agonist is selected from eletriptan, rizatriptan, zolmitriptan sumatriptan and naratriptan.

8. A method according to claim 5, wherein the cyclooxygenase-2 inhibitor is Vioxx.

9. A method according to claim 5, wherein the cyclooxygenase-2 inhibitor is selected from the group consisting of:

ethyl (2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl [6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
[6-chloro-2-(3,4-dichlorobenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-yl) acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl [6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl [5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(1-methylimidazole-2-carbonyl)-1H-indol-3-yl]acetic acid;

methyl [5-chloro-2-(thiazole-2-carbonyl)-1H-indol-3-yl]
    acetate;
[5-chloro-2-(thiazole-2-carbonyl)-1H-indol-3-yl]acetic
    acid;
methyl (2-benzoyl-6-chloro-1H-indol-3-yl)acetate;
(2-benzoyl-6-chloro-1H-indol-3-yl)-N,N-
    dimethylacetamide;
(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-
    methylacetamide;
2-(2-benzoyl-6-chloro-1H-indol-3-yl)-1-piperidino-1-
    ethanone;
2-(2-benzoyl-6-chloro-1H-indol-3-yl)-1-(4-methyl-1-
    piperazinyl)-1-ethanone;
2-(2-benzoyl-6-chloro-1H-indol-3-yl)-N-(2-cyanoethyl)
    acetamide;
(2-benzoyl-6-chloro-1H-indol-3-yl)-N-(2-hydroxyethyl)
    acetamide;
2-(2-benzoyl-6-chloro-1H-indol-3-yl)-1-morpholino-1-
    ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic
    acid;
methyl [6-chloro-2-(4-methoxybenzoyl)-1H-indol-3-yl]
    acetate;
[6-chloro-2-(4-methoxybenzoyl)-1H-indol-3-yl]acetic acid;
methyl [6-chloro-2-(4-ethylpyridine-2-carbonyl)-1H-indol-
    3-yl]acetate;
[6-chloro-2-(4-ethylpyridine-2-carbonyl)-1H-indol-3-yl]
    acetic acid;
methyl [5-chloro-2-(4-ethylpyridine-2-carbonyl)-1H-indol-
    3-yl]acetate;
[5-chloro-2-(4-ethylpyridine-2-carbonyl)-1H-indol-3-yl]
    acetic acid;
methyl [6-chloro-2-(4-isopropylpyridine-2-carbonyl)-1H-
    indol-3-yl]acetate;
[6-chloro-2-(4-isopropylpyridine-2-carbonyl)-1H-indol-3-
    yl]acetic acid;
methyl [5-chloro-2-(4-isopropylpyridine-2-carbonyl)-1H-
    indol-3-yl]acetate;
[5-chloro-2-(4-isopropylpyridine-2-carbonyl)-1H-indol-3-
    yl]acetic acid;
methyl [6-chloro-2-(4-propylpyridine-2-carbonyl)-1H-
    indol-3-yl]acetate;
[6-chloro-2-(4-propylpyridine-2-carbonyl)-1H-indol-3-yl]
    acetic acid;
methyl [5-chloro-2-(4-propylpyridine-2-carbonyl)-1H-
    indol-3-yl]acetate;
[5-chloro-2-(4-propylpyridine-2-carbonyl)-1H-indol-3-yl]
    acetic acid;
methyl [2-(4-tert-butylpyridine-2-carbonyl)-6-chloro-1H-
    indol-3-yl]acetate;
[2-(4-tert-butylpyridine-2-carbonyl)-6-chloro-1H-indol-3-
    yl]acetic acid;
methyl [2-(4-tert-butylpyridine-2-carbonyl)-5-chloro-1H-
    indol-3-yl]acetate;
[2-(4-tert-butylpyridine-2-carbonyl)-5-chloro-1H-indol-3-
    yl]acetic acid;
methyl [6-chloro-2-(3-methylpyridine-2-carbonyl)-1
    H-indol-3-yl]acetate;
[6-chloro-2-(3-methylpyridine-2-carbonyl)-1H-indol-3-yl]
    acetic acid;
methyl [5-chloro-2-(3-methylpyridine-2-carbonyl)-1H-
    indol-3-yl]acetate;
[5-chloro-2-(3-methylpyridine-2-carbonyl)-1H-indol-3-yl]
    acetic acid;
methyl [6-chloro-2-(6-methylpyridine-2-carbonyl)-1H-
    indol-3-yl [acetate;
[6-chloro-2-(6-methylpyridine-2-carbonyl)-1H-indol-3-yl]
    acetic acid;
methyl [5-chloro-2-(5-methylpyridine-2-carbonyl)-1H-
    indol-3-yl]acetate;
[5-chloro-2-(5-methylpyridine-2-carbonyl)-1H-indol-3-yl]
    acetic acid;
methyl [6-chloro-2-(5-(trifluoromethyl)pyridine-2-
    carbonyl])-H -indol-3-yl]acetate;
[6-chloro-2-[5-(trifluoromethyl)pyridine-2-carbonyl]-1
    H-indol-3-yl]acetic acid;
methyl [5-chloro-2-[5-(trifluoromethyl)pyridine-2-
    carbonyl]-H-indol-3-yl]acetate;
[5-chloro-2-[5-(trifluoromethyl)pyridine-2-carbonyl]-1H-
    indol-3-yl]acetic acid;
methyl [5-chloro-2-(5-chloro pyridine-2-carbonyl)-1
    H-indol-3-yl]acetate;
[5-chloro-2-(5-chloro pyridine-2-carbonyl)-1H-indol-3-yl]
    acetic acid;
methyl [6-chloro-2-(5-chloropyridine-2-carbonyl)-1H-
    indol-3-yl]acetate;
[6-chloro-2-(5-chloropyridine-2-carbonyl)-1H-indol-3-yl]
    acetic acid;
methyl [5-chloro-2-(4-chloropyridine-2-carbonyl)-1H-
    indol-3-yl]acetate;
[5-chloro-2-(4-chloropyridine-2-carbonyl)-1H-indol-3-yl]
    acetic acid;
methyl [6-chloro-2-(pyridine-3-carbonyl)-1H-indol-3-yl]
    acetate;
[6-chloro-2-(pyridine-3-carbonyl)-1H-indol-3-yl]acetic
    acid;
methyl [6-chloro-2-(pyridine-4-carbonyl)-1H-indol-3-yl]
    acetate;
[6-chloro-2-(pyridine-4-carbonyl)-1H-indol-3-yl]acetic
    acid;
methyl [6-chloro-2-[4-(hydroxymethyl)pyridine-2-
    carbonyl]-1H-indol-3-yl]acetate;
[6-chloro-2-[4-(hydroxymethyl)pyridine-2-carbonyl]-1H-
    indol-3-yl]acetic acid;
methyl [5-chloro-2-[4-(hydroxymethyl)pyridine-2-
    carbonyl]-1H-indol-3-yl]acetate;
[5-chloro-2-[4-(hydroxymethyl)pyridine-2-carbonyl]-1H-
    indol-3-yl]acetic acid;
methyl [5-chloro-2-(3,4-dimethylpyridine-2-carbonyl)-1H-
    indol-3-yl]acetate;
[5-chloro-2-(3,4-dimethylpyridine-2-carbonyl)-1H-indol-3-
    yl]acetic acid;
methyl [5-chloro-2-(4,5-dimethylpyridine-2-carbonyl)-1H-
    indol-3-yl]acetate;
[5-chloro-2-(4,5-dimethylpyridine-2-carbonyl)-1H-indol-3-
    yl]acetic acid;
methyl (6-chloro-2-(4,5-dimethylpyridine-2-carbonyl)-1H-
    indol-3-yl]acetate;
[6-chloro-2-(4,5-dimethylpyridine-2-carbonyl)-1H-indol-3-
    yl]acetic acid;
methyl [6-chloro-2-(4-methoxypyridine-2-carbonyl)-1H-
    indol-3-yl]acetate;
[6-chloro-2-(4-methoxypyridine-2-carbonyl)-1H-indol-3-
    yl]acetic acid;
methyl [ -chloro-2-(4-methoxypyridine-2-carbonyl)-1H-
    indol-3-yl]acetate;
[5-chloro-2-(4-methoxypyridine-2-carbonyl)-1H-indol-3-
    yl]acetic acid;
methyl [6-chloro-2-(3,5-dimethylpyridine-2-carbonyl)-1H-
    indol-3-yl]acetate;
[6-chloro2-(3,5-dimethylpyridine-2-carbonyl)-1H-indol-3-
    yl]acetic acid;

methyl [5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl [6-chloro-2-(4-ethyl-3-fluoropyridine-2-carbonyl)-1H-indol-3-yl] acetate;
[6-chloro-2-(3-ethoxy-4-ethylpyridine-2-carbonyl)-1H-indol-3-yl]acetic acid;
methyl [6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl [5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl [5-chloro-2-(4,6-dimethyl pyridine-2-carbonyl)-1H-indol-3-yl]acetate;
[5-chloro-2-(4,6-dimethylpyridine-2-carbonyl)-1H-indol-3-yl]acetic acid;
methyl [6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl [5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl [5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl [5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl [5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl [6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl [5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl [5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl [6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl [5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl [2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl [5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl [2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl [2-(4-ethylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl [6-methyl-2-(4-methylpyridine-2-carbonyl)-1H-indol-3-yl]acetate;
[6-methyl-2-(4-methylpyridine-2-carbonyl)-1H-indol-3-yl] acetic acid;
methyl [2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl [2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl (2-benzoyl-1H-indol-3-yl)acetate;
(2-benzoyl-1H-indol-3-yl)acetic acid;
methyl [2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl [6-methoxy-2-(4-chlorobenzoyl)-1H-indol-3-yl]acetate;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
methyl [2-(4-chlorobenzoyl)-5-ethyl-1H-indol-3-yl]acetate;
[2-(4-chlorobenzoyl)-5-ethyl-1H-indol-3-yl]acetic acid;
methyl [2-(4-chlorobenzoyl)-5-methoxy-1H-indol-3-yl]acetate;
[2-(4-chlorobenzoyl)-5-methoxy-1H-indol-3-yl]acetic acid;
methyl [2-(4-chlorobenzoyl)-5-isopropyl-1H-indol-3-yl]acetate;
[2-(4-chlorobenzoyl)-5-isopropyl-1H-indol-3-yl]acetic acid;
methyl [2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl [2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl [6-chloro-2-(2-methoxybenzoyl)-1H-indol-3-yl]acetate;
[6-chloro-2-(2-methoxybenzoyl)-1H-indol-3-yl]acetic acid;
methyl [6-chloro -2-(3-methoxybenzoyl)-1H-indol -3-yl]acetate;
[6-chloro-2-(3-methoxybenzoyl)-1H-indol-3-yl]acetic acid;
methyl [-chloro-2-(3-benzyloxybenzoyl)-1H-indol-3-yl]acetate;
[6-chloro-2-(3-benzyloxybenzoyl)-1H-indol-3-yl]acetic acid;
methyl [6-chloro-2-(3-hydroxybenzoyl)-1H-indol-3-yl]acetate;
[6-chloro-2-(3-hydroxybenzoyl)-1H-indol-3-yl]acetic acid;
methyl [6-chloro-2-(4-benzoxybenzyloyl)-1H-indol-3-yl]acetate;
[6-chloro-2-(4-benzyloxybenzoyl)-1H-indol-3-yl]acetic acid;
methyl [6-chloro -2-(4-hydroxybenzoyl)-1H-indol-3-yl]acetate;

[6-chloro-2-(4-hydroxybenzoyl)-1H-indol-3-yl]acetic acid;
methyl [6-chloro-2-(4-isopropoxybenzoyl)-1H-indol-3-yl]acetate;
[6-chloro-2-(4-isopropoxybenzoyl)-1H-indol-3-yl]acetic acid;
methyl [6-chloro -2-(4-phenylbenzoyl)-1H-indol-3-yl]acetate;
[6-chloro-2-(4-phenylbenzoyl)-1H-indol-3-yl]acetic acid;
methyl [6-chloro-2-(4-trifluoromethoxybenzoyl)-1H-indol-3-yl]acetate;
[6-chloro 2-(4-trifluoromethoxybenzoyl)-1H-indol-3-yl]acetic acid;
methyl [5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl [5-chloro-2-(4-methoxybenzoyl)-1H-indol-3-yl]acetate;
[5-chloro-2-(4-methoxybenzoyl)-1H-indol-3-yl]acetic acid;
methyl [6-chloro-2-(4-nitrobenzoyl)-1H-indol-3-yl]acetate;
[6-chloro-2-(4-nitrobenzoyl)-1H-indol-3-yl]acetic acid;
methyl [6-chloro-2-[(4-methylsulfonyl)benzoyl]-1H-indol-3-yl]acetate;
[6-chloro-2-[(4-methylsulfonyl)benzoyl]-1H-indol-3-yl]acetic acid;
methyl [6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl [6-chloro-2-(4-chloro-3-fluorobenzoyl)-1H-indol-3-yl]acetate;
[6-chloro-2-(4-chloro-3-fluorobenzoyl)-1H-indol-3-yl]acetic acid;
methyl [6-chloro-2-(4-cyanobenzoyl)-1H-indol-3-yl]acetate;
methyl [6-chloro-2-[4-bromobenzoyl]-1H-indol-3-yl]acetate;
methyl [6-chloro-2-[4-(2-thienyl)benzoyl]-1H-indol-3-yl]acetate;
[6-chloro-2-[4-(2-thienyl)benzoyl]-1H-indol-3-yl]acetic acid;
methyl [6-chloro-2-[4-(2-furyl)benzoyl]-1H-indol-3-yl]acetate;
[6-chloro-2-[4-(2-furyl)benzoyl]-1H-indol-3-yl]acetic acid;
methyl [6-chloro-2-[4-(3-pyridyl)benzoyl]-1H-indol-3-yl]acetate;
[6-chloro-2-[4-(3-pyridyl)benzoyl]-1H-indol-3-yl]acetic acid;
methyl [6-chloro-2-[4-(2-thiazolyl)benzoyl]-1H-indol-3-yl]acetate;
[6-chloro-2-[4-(2-thiazolyl)benzoyl]-1H-indol-3-yl]acetic acid;
methyl [6-chloro-2-(3-bromobenzoyl)-1H-indol-3-yl]acetate;
methyl [6-chloro-2-[3-(2-furyl)benzoyl]-1H-indol-3-yl]acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl]propionate;
dl-2-[2-(4-chlorobenzoyl)-6-chloro-1H-indol-3-yl]propionic acid;
methyl [5-chloro-2-(isoquinoline-3-carbonyl)-1H-indol-3-yl]acetate;
[5-chloro-2-(isoquinoline-3-carbonyl)-1H-indol-3-yl]acetic acid;
methyl [6-chloro-2-(isoquinoline-3-carbonyl)-1H-indol-3-yl]acetate;
[6-chloro-2-(isoquinoline-3-carbonyl)-1H-indol-3-yl]acetic acid;
methyl [5-chloro-2-(5-methylisoxazole-3-carbonyl)-1H-indol-3-yl]acetate;
[5-chloro-2-(5-methylisoxazole-3-carbonyl)-1H-indol-3-yl]acetic acid;
methyl [6-chloro-2-(5-methylisoxazole-3-carbonyl)-1H-indol-3-yl]acetate;
[6-chloro-2-(5-methylisoxazole-3-carbonyl)-1H-indol-3-yl]acetic acid;
methyl [5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl [6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl [5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl[6-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-(2-thienyl)carbonylindol-3-yl]acetic acid;
methyl [6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl [6-chloro-2-[3-methoxymethyl-2furoyl]-1H-indol-3-yl]acetate;
[6-chloro-2-[3-methoxymethyl-2-furoyl]-1 H-indol-3-yl]acetic acid;
[6-chloro-2-(1-methylimidazole-2-carbonyl)-1H-indol-3-yl]acetic acid;
methyl [6-chloro -2-(1-methylimidazole -2-carbonyl)-1H-indol-3-yl]acetate;
methyl [5-chloro-2-(1-methylimidazole-2-carbonyl)-1H-indol-3-yl]acetate;
[5-cloro-2(1-methylimidazole-2-carbonyl)-1H-indol-3-yl]acetic acid;
methyl [5-chloro-2-(imidazole-2-carbonyl)-1H-indol-3-yl]acetate;
[5-chloro-2-(imidazole-2-carbonyl)-1H-indol-3-yl]acetic acid;
methyl [6-chloro-2-(imidazole-2-carbonyl)-1H-indol-3-yl]acetate;
[6-cloro-2-(imidazole-2-carbonyl)-1H-indol-3-yl]acetic acid;
methyl [5-chloro-2-(4-methylthiazole-2-carbonyl)-1H-indol-3-yl]acetate;
[5-chloro-2-(4-methylthiazole-2-carbonyl)-1H-indol-3-yl]acetic acid;
methyl [5-chloro-2-(4-methylpyrrole-2-carbonyl)-1H-indol-3-yl]acetate;
[5-chloro-2-(1-methylpyrrole-2-carbonyl)-1H-indol-3-yl]acetic acid;
methyl [5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl [5-chloro-2-(thiazole-5-carbonyl)-1H-indol-3-yl]acetate;

[5-chloro-2-(thiazole-5-carbonyl)-1H-indol-3-yl]acetic acid;
methyl [6-chloro-2-(4-methylthiazole-2-carbonyl)-1H-indol-3-yl]acetate;
[6-chloro-2-(4-methylthiazole-2-carbonyl)-1H-indol-3-yl]acetic acid;
methyl [5-chloro-2-[3-(ethoxycaronyl)isoxazole-5-carbonyl]-1H-indol-3-yl]acetate;
[5-chloro-2-[3-(carboxy)isoxazole-5-carbonyl]-1H-indol-3-yl]acetic acid;
methyl [6-chloro-2-cyclopropanecarbonyl-1H-indol-3-yl]acetate;
[6-chloro-2-cyclopropanecarbonyl-1H-indol-3-yl]acetic acid;
methyl [6-chloro-2-cyclobutanecarbonyl-1H-indol-3-yl]acetate;
[6-chloro-2-cyclobutanecarbonyl-1H-indol-3-yl]acetic acid;
methyl [5-(tert-butyl)-2-(4-chlorobenzoyl)-1H-indol-3-yl]acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanol;
[5-chloro-2-(4-methylpyridine-2-carbonyl)-1H-indol-3-yl]-N-(2-aminoethyl)acetamide;
2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl]acetic acid;
methyl [6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;
methyl [6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl [5-acetyl-2-(4-chlorobenzoyl)-1H-indol-3-yl]acetate;
[5-acetyl-2-(4-chlorobenzoyl)-1H-indol-3-yl]acetic acid;
methyl [6-chloro-2-(4-chlorobenzoyl)-5-fluoro-1H-indol-3-yl]acetate;
methyl [6-fluoro-2-(4-methylpridine-2-carbonyl]-1H-indol-3-yl]acetate;
[6-fluoro-2-(4-methylpridine-2-carbonyl)-1H-indol-3-yl]acetic acid;
methyl [64-fluoro-2-(4-chlorobenzoyl)-1H-indol-3-yl]acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
[2-(4-methylpyridine-2-carbonyl)-5-methylthio-1H-indol-3-yl]acetic acid, and a salt thereof.

10. A method according to claim 5, wherein the 5HT$_1$ receptor agonist, caffeine, and the cyclooxygenase-2 inhibitor are administered separately according to a dose regimen that renders the combination of the separately administered active agents effective in the treatment of migraine.

11. A method according to claim 5, wherein the 5HT$_1$ receptor agonist, caffeine, and the cyclooxygenase-2 inhibitor are administered together according to a dose regimen that renders the combination of the administered active agents effective in the treatment of migraine.

12. A method according to claim 5, wherein the 5HT$_1$ receptor agonist is administered in an amount from about 0.05 mg to about 100 mg per day, caffeine is administered in an amount from about 15 mg to about 200 mg per day, and the cyclooxygenase-2 inhibitor is administered in an amount from about 10 mg to about 300 mg per day.

* * * * *